(12) United States Patent
Tomimatsu et al.

(10) Patent No.: US 7,999,240 B2
(45) Date of Patent: *Aug. 16, 2011

(54) METHOD AND APPARATUS FOR SPECIMEN FABRICATION

(75) Inventors: Satoshi Tomimatsu, Kokubunji (JP); Kaoru Umemura, Musashino (JP); Yuichi Madokoro, Kokubunji (JP); Yoshimi Kawanami, Kokubunji (JP); Yasunori Doi, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 60 days.

This patent is subject to a terminal disclaimer.

(21) Appl. No.: 12/168,232

(22) Filed: Jul. 7, 2008

(65) Prior Publication Data

US 2008/0296497 A1    Dec. 4, 2008

Related U.S. Application Data

(60) Continuation of application No. 11/701,415, filed on Feb. 2, 2007, now Pat. No. 7,397,052, which is a continuation of application No. 11/452,378, filed on Jun. 14, 2006, now Pat. No. 7,176,458, which is a continuation of application No. 11/390,201, filed on Mar. 28, 2006, now Pat. No. 7,138,628, which is a continuation of application No. 10/941,913, filed on Sep. 16, 2004, now Pat. No. 7,071,475, which is a continuation of application No. 10/395,237, filed on Mar. 25, 2003, now Pat. No. 6,828,566, which is a division of application No. 09/202,540, filed on Dec. 16, 1998, now Pat. No. 6,538,254.

(30) Foreign Application Priority Data

Jul. 22, 1997 (JP) .................................. 9-196213
Sep. 29, 1997 (JP) .................................. 9-263184
Sep. 29, 1997 (JP) .................................. 9-263185

(51) Int. Cl.
 *H01J 37/20* (2006.01)
(52) U.S. Cl. ........................................ 250/492.21
(58) Field of Classification Search ........... 250/492.21, 250/306, 311, 309
See application file for complete search history.

(56) References Cited

U.S. PATENT DOCUMENTS 4,030,615 A    6/1977 Guggi et al.
(Continued)

FOREIGN PATENT DOCUMENTS

DE    218954    9/1982
(Continued)

OTHER PUBLICATIONS

Brady, et al., IBM technical Disclosure Bulletin, Apr. 1991, pp. 280-281.

(Continued)

*Primary Examiner* — Kiet T Nguyen
(74) *Attorney, Agent, or Firm* — Antonelli, Terry, Stout & Kraus, LLP.

(57) ABSTRACT

A system for analyzing a semiconductor device, including: a first ion beam apparatus including: a sample stage to mount a sample substrate; a vacuum chamber in which the sample stage is placed; an ion beam irradiating optical system to irradiate the sample substrate; a specimen holder that accommodates a plurality of specimens separated from the sample substrate by the irradiation of the ion beam; and a probe to extract the separated specimen from the sample substrate, and to transfer the separated specimen to the specimen holder; a second ion beam apparatus that carries out a finishing process to the specimen; and an analyzer to analyze the finished specimen, wherein the first ion beam apparatus separates the specimen and the probe in a vacuum condition.

14 Claims, 29 Drawing Sheets

U.S. PATENT DOCUMENTS

| | | | |
|---|---|---|---|
| 4,128,765 A | 12/1978 | Franks | |
| 5,063,294 A | 11/1991 | Kawata et al. | |
| 5,270,552 A | 12/1993 | Ohnishi et al. | |
| 5,412,503 A | 5/1995 | Nederlof | |
| 5,656,811 A | 8/1997 | Itoh et al. | |
| 5,852,298 A | 12/1998 | Hatakeyama et al. | |
| 5,892,225 A | 4/1999 | Okihara | |
| 6,188,068 B1 | 2/2001 | Shaapur et al. | |
| 6,188,072 B1 | 2/2001 | Chung | |
| 6,194,720 B1 | 2/2001 | Li et al. | |
| 6,538,254 B1 | 3/2003 | Tomimatsu et al. | |
| 6,664,552 B2 | 12/2003 | Shichi et al. | |
| 6,717,156 B2 | 4/2004 | Sugaya et al. | |
| 6,828,566 B2 | 12/2004 | Tomimatsu et al. | |
| 6,858,851 B2 | 2/2005 | Tomimatsu et al. | |
| 6,960,765 B2 | 11/2005 | Tomimatsu et al. | |
| 7,071,475 B2 | 7/2006 | Tomimatsu et al. | |
| 7,326,942 B2 * | 2/2008 | Shichi et al. | 250/492.21 |
| 7,397,052 B2 * | 7/2008 | Tomimatsu et al. | 250/492.21 |

FOREIGN PATENT DOCUMENTS

| | | |
|---|---|---|
| JP | 49-33904 | 9/1974 |
| JP | 4-76437 | 3/1992 |
| JP | 4-248237 | 9/1992 |
| JP | 5-52721 | 3/1993 |
| JP | 5-302876 | 11/1993 |
| JP | 7-333120 | 12/1995 |
| JP | 8-3768 | 1/1996 |
| JP | 8-209340 | 8/1996 |
| JP | 08-304243 | 11/1996 |
| JP | 9-134699 | 5/1997 |
| JP | 9-162098 | 6/1997 |
| JP | 9-189649 | 7/1997 |

OTHER PUBLICATIONS

Guanuzzi, et al., Materials Research Society Symposium, Proceedings 480, Specimen Preparation for Transmission Electron Microscopy of Materials IV, Apr. 2, 1997, pp. 19-27.

Ishitani, et al., Hitachi Review, vol. 45, #1, Feb. 1996, pp. 19-24.

K. Nikawa, New Application of Focused Ion Beam Technique to Failure Analysis and Process Monitoring of VLSI, Proceedings of International Reliability Physics Symposum, (1989), pp. 43-52.

Preparation of TEM Specimens from Whole Wafers Using Focused Ion Beam and In Situ Extraction Techniques, temappl. Pm6 rev., Jul. 1997.

Saapur, et al., Materials Research Society Symposium, Proceedings 480, Specimen Preparation Electron Microscopy of Materials IV, Apr. 2, 1997, pp. 173-180.

Su, et al., Materials Research Society Symposium Proceedings 480, Specimen Preparation for Transmission Electron Microscopy of Materials IV, Apr. 2, 1997, pp. 105-117.

T.T. Sheng, et al., FIB Precision TEM Sample Preparation Using Carbon Replica, Proceedings of 6th IPFA 1997, pp. 92-96.

T.T. Sheng, et al., Precision transmission electron microscopy sample preparation using a focused ion beam by extraction method, J. of Vacuum Science and technology B, vol. 15, #3, May/Jun. 1997, pp. 610-613.

Yih-Yuh Doongs, et al., Proceedings of the '97 6th International Symposium on Jul. 21-25, 1997, pp. 80-85.

E. Kirk et al., Microscopy of Semiconducting Materials 1989, Institute of Physics Serial No. 100, pp. 501-506.

T. Nakamura, editor, Lecture on Experimental Physics Part 13 Preparing and Machining Sample, First Edition, pp. 711-713, 1981.

S. Horiuchi, High Resolution Electron Microscope: Principle and Usage, pp. 182, Kyoritu-Shuppan publication (1989).

M. Overwijk et al., Journal of Vacuum Science & Technology B, vol. 11, No. 6, 1993, pp. 2021-2024.

L. Herlinger et al., "TEM Sample Preparation Using A Focused Ion Beam and A Probe Manipulalor", 1996, pp. 199-205.

A. Yamaguchi et al., Journal of Vacuum Science & Technology B, vol. 11, No. 6, 1993, pp. 2016-2020.

S. Morris et al., "A Technique for Preparing TEM Cross Sections to a Specific Area Using the FIB", ISTFA'91, 1991, pp. 417-427.

J. Szot et al., Journal of Vacuum Science & Technology B, vol. 10, No. 2, 1992, pp. 575-579.

K. Nikawa, "Applications of focused ion beam technique to failure analysis of very large scale integrations: A review", Journal of Vacuum Science & Technology B, vol. 9, No. 5, 1991, pp. 2566-2577.

T. Ishitani et al., Journal of Vacuum Science & Technology B, vol. 9, No. 5, 1991, pp. 2633-2637.

U.S. Appl. No. 60/05.0,019, filed Jun. 16, 1997, Shaapur et al.

* cited by examiner (a)

(b)

(c)

(a)

(b)

(c)

(a)

(b)

METHOD AND APPARATUS FOR SPECIMEN FABRICATION

CROSS REFERENCE TO RELATED APPLICATION

This is a continuation of application Ser. No. 11/701,415, filed Feb. 2, 2007, now U.S. Pat. No. 7,397,052 which is a continuation of application Ser. No. 11/452,378, filed Jun. 14, 2006 (now U.S. Pat. No. 7,176,458), which is a continuation of application Ser. No. 11/390,201, filed Mar. 28, 2006 (now U.S. Pat. No. 7,138,628), which is a continuation of application Ser. No. 10/941,913, filed Sep. 16, 2004 (now U.S. Pat. No. 7,071,475), which is a continuation of application Ser. No. 10/395,237, filed Mar. 25, 2003 (now U.S. Pat. No. 6,828,566), which is a divisional of application Ser. No. 09/202,540, filed Dec. 16, 1998 (now U.S. Pat. No. 6,538,254). This application relates to and claims priority from Japanese Patent Application Nos. 9-196213, filed on Jul. 22, 1997; 9-263185 and 9-262184, both filed on Sep. 29, 1997. The entirety of the contents and subject matter of all of the above is incorporated herein by reference.

BACKGROUND OF THE INVENTION

1. Field of the Invention

The present invention relates to a method and an apparatus for fabrication of a specimen. More particularly, the present invention relates to a method and an apparatus for extracting a micro-specimen including a specific small area of a semiconductor material such as a semiconductor wafer or a semiconductor device chip from the semiconductor material by separation using an ion beam and for fabricating a specimen used for carrying out an observation, an analysis and/or a measurement of the specific small area.

2. Description of the Prior Art

In recent years, efforts made to shrink geometries of semiconductor devices make progress at a very great pace. In a structure analysis of these semiconductor devices, there has been demanded an observation of a nanoscopic structure which is so small that, at a resolution of an ordinary scanning electron microscope referred to hereafter simply as an SEM, the structure can not be observed any longer. As a result, observation by means of a transmission electron microscope which is abbreviated hereafter to a TEM is indispensable in place of an SEM. Traditionally, however, fabrication of a specimen for an observation using a TEM can not help resorting to manual work which must be done by a well trained person and takes a long time. For this reason, in reality, the method for observation of a specimen using a TEM does not come into wide use as the method for observation by means of an SEM, whereby a specimen can be fabricated with ease and results of observations can be thus be obtained immediately, did.

The conventional method for fabrication of a specimen for an observation by using a TEM is explained as follows FIG. 2 is diagrams showing the first conventional method for fabrication of a specimen for observation using a TEM. A specimen for observation using a TEM is also referred to hereafter simply as a TEM specimen. To be more specific, FIG. 2/(a) is a diagram showing a semiconductor wafer 2 on which LSIs were fabricated. The semiconductor wafer 2 is referred to hereafter simply as a wafer or a substrate. As shown in FIG. 2/(b), the wafer 2 comprises an upper-layer portion 2A and a lower-portion 2B or a substrate. Assume that a specimen for TEM observation of a specific area on the wafer 2 is fabricated. First of all, a mark not shown in the figure is put on an area 22 subjected to the observation using a TEM. By exercising care so as not to damage the area 22 to be observed, an injury is deliberately inflicted on the wafer 2 by using a tool such as a diamond pen in order to cleave the wafer 2 or the wafer 2 is cut by means of a dicing saw in order to take out a sliber chip 21 shown in FIG. 2/(b). In order to make the center of a TEM specimen being created the area 22 to be observed, the areas 22 of two chips are stuck to each other by using adhesive 23 to produce 2 specimens 24 stuck together as shown in FIG. 2/(c). Then, the two stuck specimens 24 are sliced by means of a diamond cutter to produce slice specimens 25 shown in FIG. 2/(d). The dimensions of each of the slice specimens 25 are about 3 mm×3 mm×0.5 mm. Then, the slice specimen 25 is put on a grinding plate to be ground by using abrasives into a thin specimen, namely, a ground specimen 25' with a thickness of about 20 microns. Subsequently, the ground specimen 25' is attached to a single-hole holder 28 mounted on a TEM stage, that is, a stage for holding a TEM specimen as shown in FIG. 2/(e). Then, ion beams 27 are irradiated to the surfaces of the ground specimen 25' as shown in FIG. 2/(f). Sputtering fabrication (or ion-milling fabrication) is then carried out on the center of the specimen 25' as shown in FIG. 2/(g). Finally, when a hole has been bored through the center of the specimen 25', the irradiation of the ion beams 27 is halted as shown in FIG. 2/(h). A thinned area 26 with a thickness not exceeding a value of about 100 nm fabricated as described above has been observed by a TEM. This method is described in references such as a book with a title of "High-Resolution Electron Microscope: Principle and Usage", authored by Hisao Horiuchi and published by Kyoritsu Syuppan, Page 182, and used as prior-art reference 1.

FIG. 3 is a diagram showing the second conventional method for fabrication of a TEM specimen. This method is a method for fabrication of a specimen using a focused ion beam which is abbreviated hereafter to an FIB. As shown in the figure, first of all, a mark not shown in the figure is created by using a laser beam or an FIB in the vicinity of an area 22 to be observed on the wafer 2 and then the wafer 2 is diced as shown in FIG. 3/(a). A sliver chip 21 shown in FIG. 3/(b) is then taken out from the wafer 2. The sliver chip 21 is further sliced to produce slice specimens 21' shown in FIG. 3/(c). The dimensions of each of the slice specimens 21' are about 3 mm×0.1 mm×0.5 mm which is the thickness of the wafer 2. Then, the slice chip 21' is ground into a thinned specimen 21". The thinned specimen 21" is then stuck to a TEM-specimen holder 31 which resembles a thin metallic disc plate and has a cut portion 31' as shown in FIG. 3/(d). Subsequently, the area 22 to be observed on the thinned specimen 21" is further thinned by means of an FIB 32 so that only a slice 22' having a thickness of about 100 nm is left as shown in FIG. 3/(e), (f). The slice 22' is used as a specimen for an observation using a TEM. This method is described in documents such as a collection of theses with a title of "Microscopy of Semiconducting Materials 1989", Institute of Physics Series No. 100, Pages 501 to 506, which is used as prior-art reference 2.

FIG. 4 is a diagram showing the third conventional method for fabrication of a TEM specimen. The method is disclosed in Japanese Patent Laid-open No. Hei 5-52721 which is used as prior-art reference 3. As shown in the figure, first of all, a specimen substrate 2 is held in such a posture that an FIB 32 is irradiated to the surface of the specimen substrate 2 perpendicularly. The surface of the specimen substrate 2 is then scanned by the FIB 32 along the circumference of a rectangle to form a rectangular hole 33 with a sufficient thickness on the surface as shown in FIG. 4/(a). Then, the specimen substrate 2 is inclined so that the surface thereof forms a gradient of about 70 degrees with the axis of the FIB 32 and a bottom trench 34 for separation is further created on a side wall of the rectangular hole 33 as shown in FIG. 4/(b). The gradient angle of the specimen substrate 2 is adjusted by using a sample stage which is not shown in the figure. Subsequently, the orientation of the specimen substrate 2 is restored to its original posture so that the FIB 32 is again irradiated to the surface of the specimen substrate 2 perpendicularly and a trench 35 is further created as shown in FIG. 4/(c). Then, by driving a manipulator for holding a probe 36, the tip of the probe 36 is brought into contact with the surface of a portion 40 of the specimen substrate 2 to be separated as shown in FIG. 4/(d). It should be noted that the manipulator itself is not shown in the figure. In this state, the FIB 32 is irradiated to a local area including the tip of the probe 36 while gas 39 for deposition is being supplied from a gas nozzle 37 to create an ion-beam-assisted-deposition film 38 which is abbreviated hereafter to an IBAD film or a deposition film. In this way, the portion 40 of the specimen substrate 2 to be separated and the tip of the probe 36 which have been brought into contact with each other are firmly joined to each other by the deposition film 38 as shown in FIG. 4/(e). Finally, portions left around the portion 40 of the specimen substrate 2 to be separated are separated by the FIB 32 to detach the portion 40 from the specimen substrate 2 as shown in FIG. 4/(f). The detached portion 40 separated from the specimen substrate 2 remains in a state of being firmly joined to the tip of the probe 36 as shown in FIG. 4/(g). An area on the separated portion 40 to be observed is further thinned by using an FIB to a thickness of about 100 nm to produce a specimen for observation using a TEM.

The first and second conventional methods described above can not help resorting to manual work requiring skills of a well trained person fabricating the specimen. The manual work includes grinding, mechanical fabrication and sticking the specimen to the TEM-specimen holder. In addition, with these conventional methods, in order to fabricate a desired specimen, it is necessary to split the wafer or the substrate of the device chips into portions by cleaving or cutting the wafer or the substrate. In order to acquire a specimen of a desired area, portions adjacent to the desired area are inevitably and/or inadvertently cleaved or cut. Assume that it is necessary to observe and/or analyze a portion other than an area which was subjected to an observation and/or an analysis before. Since the substrate of the specimen was once cut in order to fabricate specimens for the prior observation and/or analysis, an injury and/or a damage was inevitably and/or inadvertently inflicted upon the portion subjected to the next observation and/or analysis or a positional relation among portions to be observed and/or analyzed is no longer known. As a result, there is raised a problem that accurate information on observations and/or analyses can not be obtained continuously due to the inflicted injury and/or damage. In addition, while the ion milling and the process to thin a film by using an FIB described above do not directly involve manual work, they have a problem of a long fabrication time which is difficult to solve.

Furthermore, in recent years, there is seen a trend of an increasing wafer diameter to 300 mm. The number of device chips that can be fabricated from such a wafer also increase as well. In addition, the device itself has more added values. As a result, splitting a wafer into portions by cleaving or cutting the wafer in order to observe and/or analyze a particular area leads to a disposal to discard portions other the area to be observed and/or analyzed which is very uneconomical. Moreover, when a small particle or an abnormal shape is detected in a certain area during a scanning operation over the entire wafer by driving a variety of microscopes, a cause of such a small particle or such an abnormal shape has to be clarified by conducting an observation and/or an analysis prior to the splitting a wafer into chips, in particular, before the small particle disappears. Otherwise, a number of defective devices among final products will be resulted in, incurring an even larger loss. If a plurality of specimens can be produced in a short period of time without splitting the wafer into portions, observations and/or analyses can be carried out very economically, giving rise to a great contribution to improvements of a product manufacturing yield.

With the third conventional method, on the other hand, once a specimen is set on the sample stage, it is not necessary for the operator to do manual work directly till separation of micro-specimens and to cut the wafer carelessly. In this method, however, the separated specimen remains in a state of being attached to the tip of a probe so that, when the separated specimen is brought into an observation apparatus and/or an analyzer in such a state to be observed and/or analyzed, the specimen will vibrate, raising a problem that it is impossible to obtain reliable results of observation and/or analysis.

As the conventional TEM-specimen holder, a holder 78 with a single hole 79 shown in FIG. 7/(a), a holder 80 with a notch 108 shown in FIG. 7/(b) and a holder 109 with a mesh shown in FIG. 7/(c) are known. Assume that the single-hole-type holder 78 or the notch-type holder 80 is used in the third conventional method for specimen fabrication described above to hold a micro-specimen 40 with a small size in the range 20 to 30 microns. In this case, it is necessary to adjust the position of the micro-specimen 40 on the inner wall of the notch 108 or the single hole 79 with a high degree of accuracy, making the installation work difficult to carry out. Such a problem is not encountered with the mesh-type holder 109. This is because, by using a mesh-type holder 109 with a gap between mesh nodes adjusted to the size of the micro-specimen 40, the position at which the micro-specimen 40 is to be installed can be selected arbitrarily to a certain degree. With the mesh-type holder 109, however, an electron beam path 82 propagating toward an area 81 to be observed is shielded by a mesh structure member 109' as shown in FIG. 7/(d), making an observation using a TEM impossible in some cases.

SUMMARY OF THE INVENTION

It is thus an object of the present invention to provide an improved method for fabrication of a specimen capable of solving the problems encountered in the conventional methods described above and to provide a good apparatus for fabrication of a specimen used for implementing the improved specimen fabrication method.

To be more specific, it is a first object of the present invention to provide a specimen fabrication method capable of fabricating a specimen of a small area to undergo an observation or a measurement/analysis carried out by an observation apparatus such as a TEM or a measurement/analysis apparatus to which the specimen is to be transferred without the need for a well trained person to do manual work such as grinding and dicing and the need to split a semiconductor wafer or an LSI chip by cleaving or cutting.

It is a second object of the present invention to provide a good specimen fabrication apparatus used for implementing the specimen fabrication method provided as the first object of the invention.

It is a third object of the present invention to provide a TEM-specimen holder which is used in conjunction with a TEM and allows a micro-specimen extracted from a specimen substrate to be positioned with ease.

In order to achieve the first object of the present invention described above, the present invention provides a specimen fabrication method which comprises the steps of:

firmly joining the tip of a probe to the vicinity of an area on a specimen substrate such as an LSI chip and a semiconductor wafer held on a sample stage to be subjected to a desired observation and/or a measurement/analysis; (such an area is also referred to hereafter as an area to be observed)

irradiating an ion beam to regions surrounding the vicinity of the area to be observed;

extracting and separating a micro-specimen including the area to be observed from the specimen substrate by ion-beam sputtering fabrication;

conveying the extracted and separated micro-specimen with the micro-specimen firmly joined to the tip of the probe as it is to a TEM-specimen holder of an apparatus for conducting the desired observation and/or measurement/analysis by moving the probe or the sample stage;

firmly attaching the micro-specimen to the TEM-specimen holder;

separating the tip of the probe from the micro-specimen; and carrying out the desired observation and/or measurement/analysis which is also generically referred to hereafter simply as an observation.

In addition, in order to carry out the observation on a specific area to be observed on the specimen substrate, before firmly joining the tip of the probe to the vicinity of the specific area to be observed, a marking process of putting a mark on the specific area is performed in order to clearly indicate the specific area. After the micro-specimen has been separated from the tip of the probe, an FIB is irradiated to the specific area to be observed as indicated by the mark in order to carry out additional fabrication such as film thinning.

It should be noted that in the process of firmly joining the tip of the probe to the vicinity of the specific area to be observed, the tip can be joined to the vicinity through an ion-beam assist deposition film or a redeposition film created by ion-beam sputtering or joined by a fusion or metallic-junction technique.

In the process of separating the tip of the probe from the micro-specimen, on the other hand, an ion-beam sputtering fabrication method can be adopted. As an alternative, if a method of using adhesive as a technique of firmly joining the tip of the probe to the micro-specimen, in the process of separating the tip of the probe from the micro-specimen, an UV-ray irradiation method or a heating method can be adopted. As another alternative, a method of electrostatic absorption can be adopted as a technique of firmly joining the tip of the probe to the micro-specimen.

In addition, in order to achieve the second object of the present invention described above, the present invention provides a specimen fabrication apparatus which comprises:

a movable sample stage on which a specimen substrate is mounted;

a probe connecting means for joining the tip of a probe to the vicinity of a desired area to be observed on the specimen substrate;

a micro-specimen separating means for separating a micro-specimen including the area to be observed from the specimen substrate with the micro-specimen joined to the tip of the probe as it is by irradiation of an ion beam to regions surrounding the vicinity of the area to be observed;

a micro-specimen fixing means for firmly fixing the micro-specimen separated from the specimen substrate to a TEM-specimen holder; and a probe separating means for separating the tip of the probe from the micro-specimen firmly fixed to the TEM-specimen holder.

The sample stage comprises a sample cassette and a movable sample cassette holder for holding the sample cassette. The sample cassette is used for holding the TEM-specimen holder or a cartridge of the TEM-specimen holder which can be mounted and removed on and from the sample stage of the observation apparatus.

Typically, a probe exhibiting a spring effect can be used as the probe described above.

The probe connecting means typically comprises a probe contact means for bringing the tip of the probe into contact with the surface of the specimen substrate, and a deposition-film forming means for forming an ion-beam assist deposition film (an IBAD film) at the contact portion between the tip of the probe and the surface of the specimen substrate. Typically, the probe contact means has a manipulator mechanism for holding the probe and moving the probe relatively to the surface of the specimen substrate. On the other hand, the deposition-film forming means typically comprises an ion-beam irradiating optical system for irradiating an ion beam to the contact portion between the tip of the probe and the surface of the specimen substrate, and a gas supplying means for supplying gas for assisted deposition to the contact portion to which the ion beam is irradiated. The tip of the probe is firmly joined to the surface of the specimen substrate through the IBAD film formed by the deposition-film forming means.

The micro-specimen separating means has a configuration including an ion-beam irradiating optical system for irradiating an ion beam to the specimen substrate. The ion-beam irradiating optical system is typically a PJIB (projection ion beam) irradiating optical system comprising an ion source and a projection optical system for projecting ions emitted from the ion source on the specimen substrate as a PJIB. As an alternative, the ion-beam irradiating optical system can be an FIB (focused ion beam) irradiating optical system comprising an ion source and a focusing optical system for irradiating ions emitted from the ion source on the specimen substrate as an FIB. As another alternative, the ion-beam irradiating optical system can be a combination of the PJIB irradiating optical system and the FIB irradiating optical system. By irradiation of an ion beam which can be a PJIB or an FIB to the specimen substrate by means of the ion-beam irradiating optical system, the specimen substrate is subjected to sputter fabrication allowing the micro-specimen to be extracted and separated from the specimen surface. In addition, the micro-specimen separating means can also be configured to include a first ion-beam irradiating optical system for irradiating an ion beam to the specimen substrate from a first direction and a second ion-beam irradiating optical system for irradiating an ion beam to the specimen substrate from a second direction different from the first direction. By providing the two ion-beam irradiating optical systems in this way, the process to extract a micro-specimen from the specimen substrate can be carried out more easily. It should be noted that, as the micro-specimen separating means, a laser-beam irradiating optical system or a combination of an ion-beam irradiating optical system and a laser-beam irradiating optical system can also be used as well.

Typically, the micro-specimen fixing means comprises a specimen contact means for bringing a micro-specimen into contact with an area on the TEM-specimen holder to fix the micro-specimen to the area and a deposition-film forming means for forming an ion-beam assist deposition film (an IBAD film) at the contact portion between the micro-specimen and the area on the TEM-specimen holder to fix the micro-specimen to the area. The deposition-film forming means can have the same configuration as the deposition-film forming means employed in the probe contact means described earlier. The micro-specimen, is firmly joined to the area on the TEM-specimen holder to fix the micro-specimen to the area through the IBAD film formed by the deposition-film forming means.

The probe separating means is implemented typically by a means for irradiating an ion beam to the IBAD film through which the micro-specimen is firmly joined to the area on the TEM-specimen holder. By irradiation of an ion beam, the IBAD film fixing the tip of the probe to the micro-specimen is subjected to a sputtering process to remove the IBAD film, hence, allowing the tip of the probe to be pulled out from the micro-specimen.

It should be noted that the probe connecting means and the micro-specimen fixing means can also use a redeposition film formed by ion-beam sputtering in place of an IBAD film or adopt a fusion or metallic-junction method. In this case, the probe separating means adopts the ion-beam sputtering fabrication. In addition, the probe connecting means and the micro-specimen fixing means can also adopt an adhesion method or an electrostatic absorption method instead of the methods described above.

The specimen fabrication apparatus provided by the present invention may include an observation unit for observing the surface of the specimen substrate, the tip of the probe or the vicinity of the TEM-specimen holder. The observation unit typically comprises an electron-beam irradiating optical system for irradiating an electron beam to the aforementioned member to be observed, a secondary-electron detector for detecting secondary electrons emitted by the observed member due irradiation of the electron beam and a display sub-unit for displaying a secondary-electron image of the observed member by using a detection signal output by the secondary-electron detector. As an alternative, the observation unit can also be implemented by an optical observation apparatus such as an optical microscope. By observing the member to be observed using the observation unit, it is possible to obtain information on a contact/connection state between the tip of the probe and the surface of the specimen substrate, a separation state of the micro-specimen from the surface of the specimen substrate and a contact/connection state between the micro-specimen and the TEM-specimen holder.

In addition, the specimen fabrication apparatus provided by the present invention may also be provided with a detector for detecting a contact/connection state as well as a separation state between the tip of the probe and the surface of the specimen substrate, between the micro-specimen and the specimen substrate and between the micro-specimen and the TEM-specimen holder. The detector can make use of variations in contact resistance between the members brought into contact with each other or variations in voltage contrast on the secondary-electron image mentioned above. By virtue of the detector, it is possible to obtain information on the contact/connection state and the separation state between the respective members with a high degree of accuracy.

The TEM-specimen holder typically comprises a metallic wire for holding the micro-specimen and a support unit for firmly supporting both the ends of the metallic wire. In the configuration of the TEM-specimen holder, the micro-specimen is firmly held by the metallic wire, allowing a specimen holding system suitable for observation using a TEM to be realized.

Other objects of the present invention, its configurations and effects provided thereby will become apparent one after another from the following detailed description of embodiments.

BRIEF DESCRIPTION OF THE DRAWINGS

Embodiments of the present invention are described by referring to the following drawings wherein.

DETAILED DESCRIPTION OF THE PREFERRED EMBODIMENTS

The present invention will become more apparent from a careful study of the following detailed description of some preferred embodiments with reference to the accompanying diagrams.

First Embodiment

Figure 1:
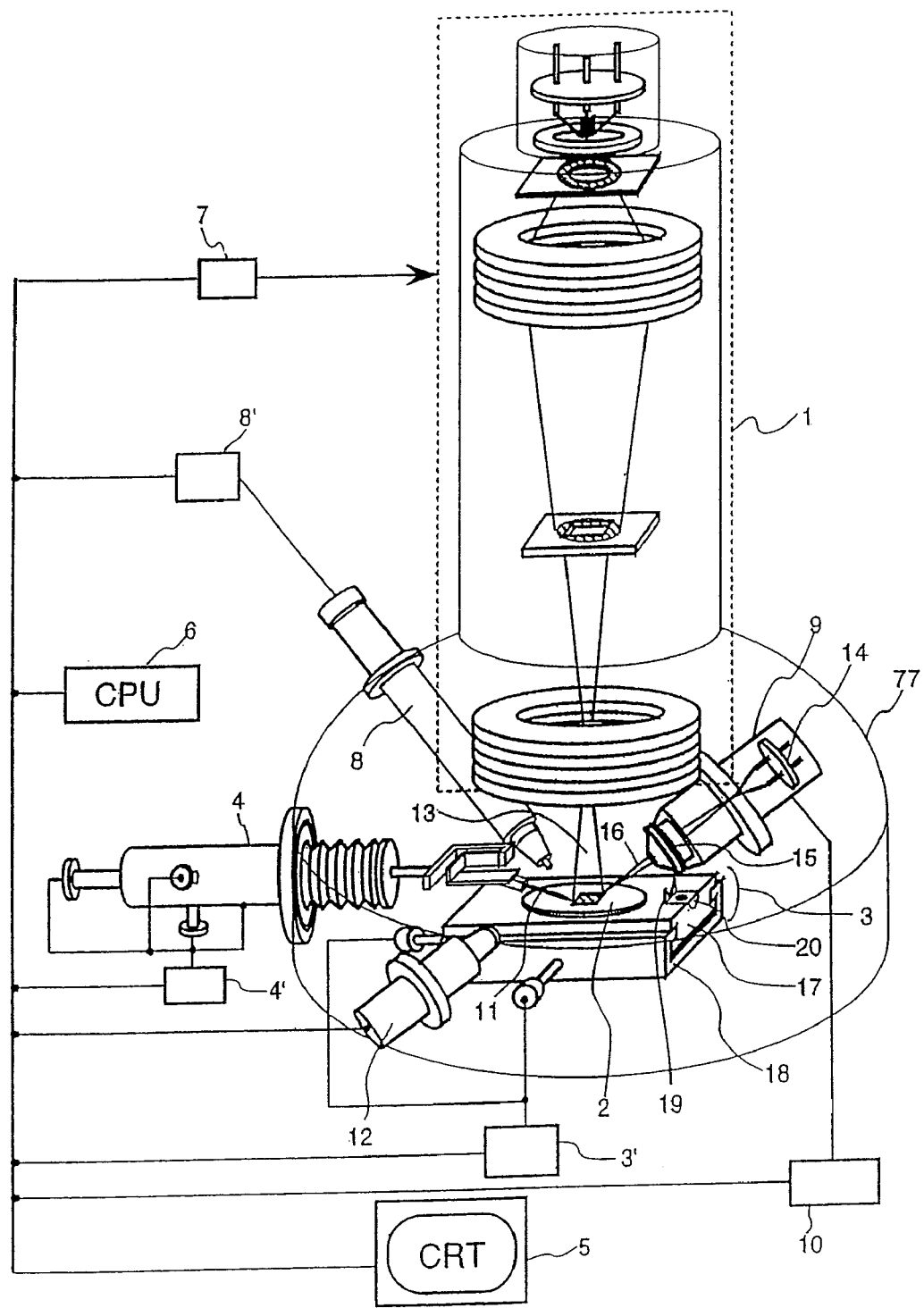
FIG. 1 is a diagram showing the basic configuration of a specimen fabrication apparatus as implemented by an embodiment of the present invention.
Figure 2:
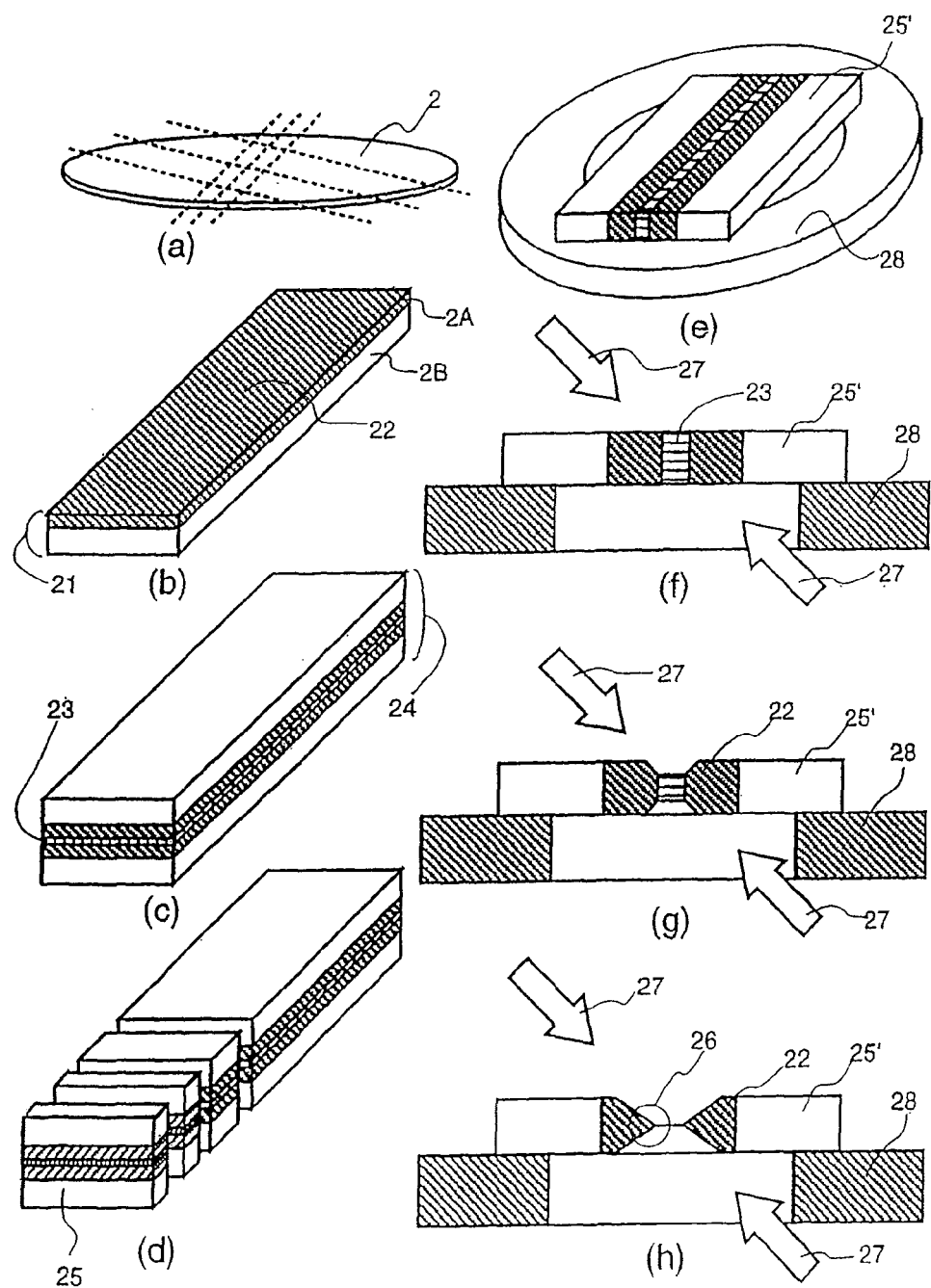
FIG. 2 is process explanatory diagrams showing an example of the conventional method for fabrication of a specimen to be observed by using a TEM.

FIG. 1 is a diagram showing the basic configuration of a specimen fabrication apparatus as implemented by an embodiment of the present invention.

As shown in the figure, the specimen fabrication apparatus implemented by the embodiment of the present invention comprises:

an ion-beam irradiating optical system 1 for irradiating an ion beam 13 to a specimen substrate 2 of a specimen, that is, an object of observation, such as a semiconductor wafer or a semiconductor chip;

a sample stage 3 for moving the specimen substrate 2 mounted thereon;

a sample-stage position controller 3' for controlling the position of the sample stage 3 in order to identify a portion of the specimen substrate 2 to be observed or an area to be observed;

a probe driver 4 for holding and moving a probe 11;

a probe-driver controller 4' for controlling the probe driver 4;

a deposition-gas supplying source 8 for supplying deposition gas, that is, gas used for deposition, to the vicinity of the area on the specimen substrate 2 to be observed;

a deposition-gas supplying source controller 8' for controlling the deposition-gas supplying source 8;

an electron-beam irradiating optical system 9 for irradiating an electron beam 16 to the surface of the specimen substrate 2; and a secondary-electron detector 12 for detecting secondary electrons emitted by the surface of the specimen substrate 2.

Note that it is needless to say that the ion-beam irradiating optical system 1, the sample stage 3, the probe driver 4, the deposition-gas supplying source 3, the electron-beam irradiating optical system 9 and the secondary-electron detector 12 are laid out in a vacuum chamber 77 which is put in a state at a high degree of vacuum.

The sample stage 3 comprises a sample cassette 17 for mounting the specimen substrate 2 and a cassette holder 18 for firmly holding the sample cassette 17. The sample stage 3 is also provided with a TEM-specimen holder clasp 20 for holding a TEM-micro-specimen holder 19 which is also referred to hereafter as a TEM holder. The TEM-specimen holder 19 is used for holding a micro-specimen separated from the specimen substrate 2 mounted on the sample stage 3 and introducing the micro-specimen into an observation/ analysis apparatus such as a TEM which is not shown in the figure. The sample stage 3 is controlled and driven by the sample-stage position controller 3' in order to arbitrarily set the orientation of the specimen substrate 2 in the 3-dimensional directions as well as a tilt angle and a rotation angle of the specimen substrate 2 with respect to the axis of the ion beam 13. In this way, an irradiation position (or a fabrication position) of the ion beam on the surface of the specimen substrate 2 as well as a glancing angle and a rotation angle of the ion beam 13 with respect to the surface of the specimen substrate 2 can be set arbitrarily.

The ion-beam irradiating optical system 1 irradiates an ion beam 13 to regions on the surface of the specimen substrate 2 surrounding the area to be observed in order to separate or to cut out a micro-specimen including the area to be observed from the specimen substrate 2 by adopting the ion-beam sputtering fabrication method. The ion beam 13 is used as an assist ion beam in a ion-beam assist deposition method (abbreviated to as an IBAD method) for firmly joining the tip of the probe 11 to the surface of the specimen substrate 2 in the vicinity of the area to be observed. In addition, the ion beam 13 is also used as an assist ion beam in the IBAD method for firmly joining a micro-specimen separated from the specimen substrate 2 to the TEM-specimen holder 19. Finally, the ion beam 13 is also used in an ion-beam sputtering fabrication for separating or detaching the tip of the probe 11 from the micro-specimen which was firmly joined to the TEM-specimen holder 19. The ion-beam irradiating optical system 1 is driven and controlled by an ion-beam driver 7.

The probe driver 4 is a so-called manipulator used for bringing the tip of the probe 11 into contact with the vicinity of the area to be observed on the surface of the specimen substrate 2 and for conveying a micro-specimen separated from the specimen substrate 2 to the TEM-specimen holder 19 with the micro-specimen firmly joined to the tip of the probe 11. The probe driver 4 is driven and controlled by the probe-driver controller 4'.

The deposition-gas supplying source 8 supplies deposition gas to the vicinity of the area to be observed on the surface of the specimen substrate 2 to form a deposition film by using the IBAD method. The tip of the probe 11 is firmly joined to the surface of the specimen substrate 2 through the deposition film. The deposition gas is also used for firmly joining the micro-specimen separated from the specimen substrate 2 to the TEM-specimen holder 19 by using the IBAD method. As the deposition gas, hexacarbonyl tungsten [W(CO)6] is typically used. To put it in detail, while the gas is being supplied to a space between members to be firmly joined to each other, that is, between the tip of the probe 11 and the surface of the specimen substrate 2 or between the micro-specimen and the TEM-specimen holder 19, an ion beam 13 is irradiated to the space to form a tungsten film (W film) therein. It is the W film that firmly joins the members to be connected to each other. In order to separate the tip of the probe 11 from the micro-specimen which have been firmly joined to each other by the W film, on the other hand, an ion beam 13 is irradiated to the W film. In this way, the W film for joining the tip of the probe 11 to the micro-specimen is removed by an ion-beam sputtering method which is abbreviated to an IBS method to the tip of the probe 11 from the micro-specimen. The deposition-gas supplying source 8 is driven and controlled by the deposition-gas supplying source controller 8'.

The electron-beam irradiating optical system 9 and the secondary-electron detector 12 constitute an observation unit for observing the surface of the specimen substrate 2 by using an SEM (scanning electron microscope) method. The observation unit irradiates an electron beam 16 emitted from the electron-beam source 14 to the surface of the specimen substrate 2 while sweeping the electron beam 16 in a scanning operation over the surface of the specimen substrate 2 by means of a deflector lens 15. Secondary electrons emitted by the surface of the specimen substrate 2 are detected by the secondary-electron detector 12 to be displayed as an SEM (scanning electron microscope) image of the surface of the specimen substrates 2 on a display sub-unit (CRT) 5. It should be noted that this observation unit is also used for observing the vicinity of the tip of the probe 11 and the vicinity of the TEM-specimen holder 19. By such observation, it is possible to verify conditions and states such as the condition of the surface of the area to be observed, the state of separation of the micro-specimen from the specimen substrate 2, the state of joining of the tip of the probe 11 to the surface of the specimen substrate 2, the state of joining of the micro-specimen to the TEM-specimen holder 19 and the state of separation of the TEM-specimen holder 19 from the micro-specimen.

It should be noted that the state of separation of the micro-specimen from the specimen substrate 2 can also be verified by detecting changes in voltage contrast of the SEM image. In addition, the state of joining and the states of separation can also be verified by detecting changes in electrical resistance (or contact resistance) between the probe 11 and the sample stage 3. The electron-beam irradiating optical system 9 is driven and controlled by an electron-beam driver 10.

It is worth noting that, since the size of the micro-specimen extracted from the specimen substrate 2 is in the range 10 to 100 microns square, an optical microscope can be used as a surface observing means.

It should be noted that the sample-stage position controller 3', the probe-driver controller 4', the ion-beam driver 7, the deposition-gas supplying source controller 8', the electron-beam driver 10 and the display sub-unit 5 are controlled by a central processing unit (CPU) 6 which serves as a central controller.

The following is a description of configurations of components composing the specimen fabrication apparatus presented in concrete terms and a description of processes implementing the method for fabrication of a specimen using the apparatus.

1-1 [Ion-Beam Irradiating Optical System]

Figure 5A:
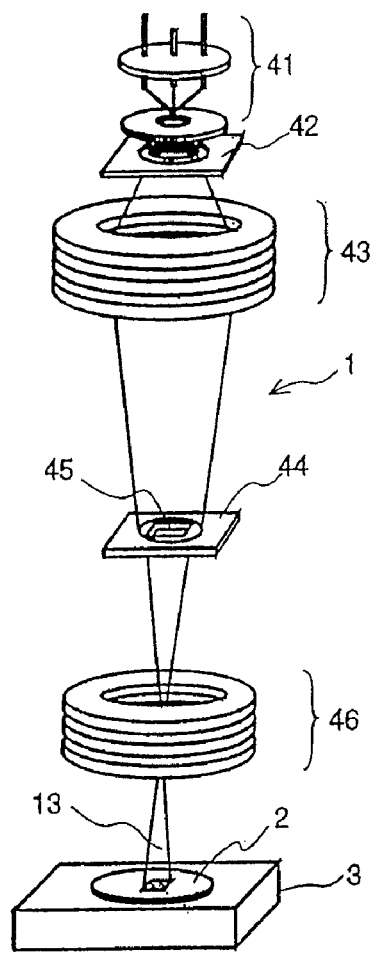
FIGS. 5A, 5B and 5C are diagrams each showing a typical configuration of main elements composing an ion-beam irradiating optical system employed in a specimen fabrication apparatus provided by the present invention.

FIG. 5A is a diagram showing a typical configuration of main elements composing an ion-beam irradiating optical system 1 for irradiating a projection ion beam (PJIB). As shown in the figure, an ion beam emitted by an ion source 41 is irradiated to a stencil mask 44 by a beam limiting aperture 42 and an illumination lens 43. The ion beam passing through an opening 45 of the stencil mask 44 is then irradiated to the surface of the specimen substrate 2 mounted on the sample stage 3 by a projection lens 46. A PJIB 13 formed in this way fabricates a figure similar to the opening 45 on the surface of the specimen substrate 2. In the case of a PJIB, the divergence of the ion beam right after leaving the ion source 41 does not have a direct effect on aberration. Thus, the ion-beam limiting angle provided by the beam limiting aperture 42 can be set at a large value. As a result, the magnitude of the ion-beam current can be increased, giving rise to a characteristic of a high fabrication speed.

Figure 5C:
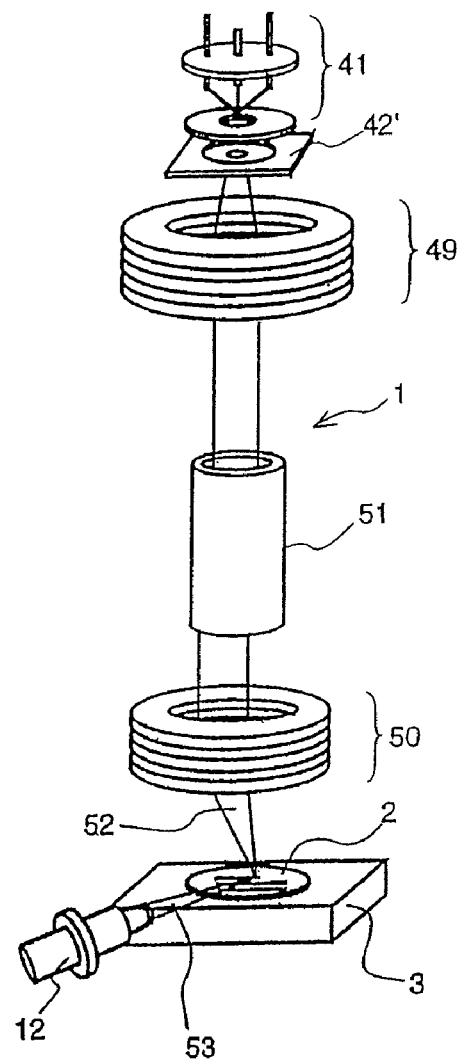
Figure 5B:
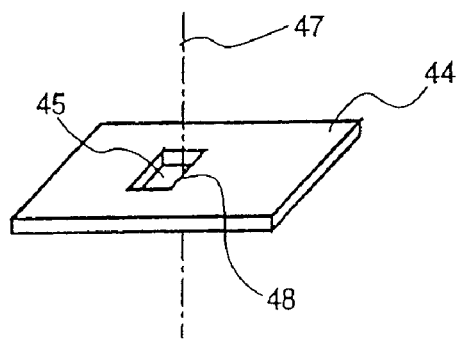

By designing the opening 45 provided on the stencil mask 44 into a rectangular pattern with a side 48 thereof passed through by the optical axis 47 as shown in FIG. 5B, the amount of side blurring of the PJIB 13 corresponding to the side 48 can be made extremely small so that the resolution of a corresponding dent formed on the specimen substrate 2 by continuous projection of the PJIB 13 can be increased. As a result, a fabricated surface corresponding to the side 48 is a cross-sectional surface perpendicular to the surface of the specimen substrate 2. By providing a rectangular opening 45 with a side 48 thereof passing through the optical axis 47 as described above, it is possible to create a structure with its wall surface erectly cut in the perpendicular direction. For more information on this, refer to Japanese Patent Laid-open No. Hei 9-162098 with a title of the invention "Method and Apparatus for Ion-Beam Fabrication".

On the other hand, FIG. 5C is a diagram showing a typical configuration of main elements composing an ion-beam irradiating optical system 1 for irradiating a focused ion beam (FIB). As shown in the figure, an ion beam emitted by an ion source 41 is formed into a focused ion beam (FIB) 52 after passing through a beam limiting aperture 42', a condenser lens 49 for suppressing divergence of the ion beam and focusing the ion beam and an objective lens 50 for focusing the ion beam on the surface of the specimen substrate 2. By sweeping the focused ion beam 52 in a scanning operation over the surface of the specimen substrate 2 using a deflector 51, an area with the scanning shape on the specimen substrate 2 is fabricated. By using such a focused ion beam 52, fabrication can be carried out with a high degree of precision. In addition, the FIB irradiating optical system 1 can also be used as a means for observing the surface of the specimen substrate 2. In order to maintain the high focusing ability of the focused ion beam 52 which is used to implement fabrication with a high degree of precision, however, it is necessary to suppress chromatic aberration and spherical aberration. In order to suppress the chromatic aberration and the spherical aberration, it is necessary to limit the aperture angle of the ion beam by means of the beam limiting aperture 42'. In consequence, the magnitude of the ion-beam current can not be increased to a large value. As a result, the FIB irradiating optical system 1 has a shortcoming that the fabrication speed is not so high. It should be noted that there are some methods to increase the fabrication speed such as an FIB (focused ion beam) assisted etching method whereby sputtering is carried out while reactive gas is being supplied to the surface of the specimen substrate 2. In order to use the focused ion beam 52 as an observation means, it is necessary to execute the steps of scanning the surface of the specimen substrate 2 by the focused ion beam 52, detecting secondary electrons 53 emanating from the surface of the specimen substrate 2 by means of the secondary-ion detector 12 and displaying an image representing the secondary electrons 53.

As described above, if a PJIB is used as an ion beam for fabrication of a specimen, there is offered a merit that high-speed fabrication can be implemented. If an FIB is used as an ion beam for fabrication of a specimen, on the other hand, gained merits are a capability of implementing high-precision fabrication and an ability of the FIB irradiating optical system to also serve as an observation means.

1-2 [Probe Driver]

Figure 6:
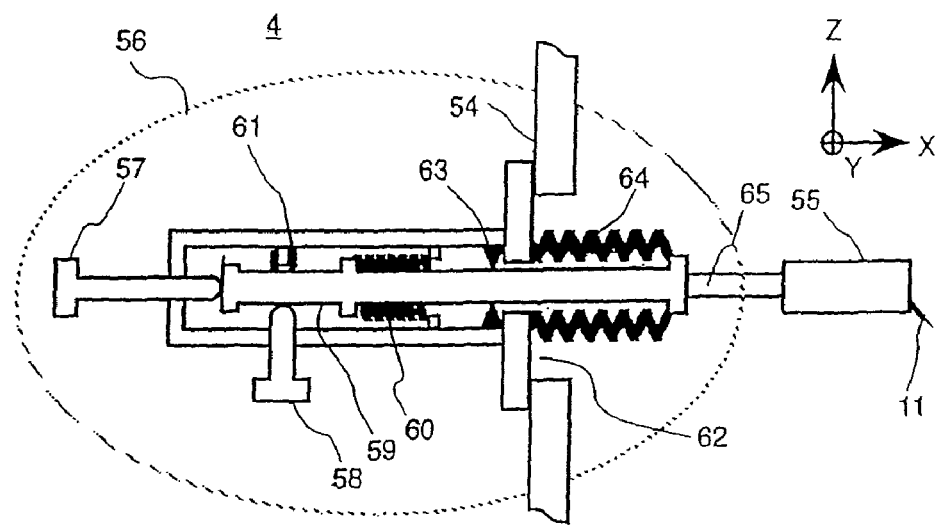
FIGS. 6A, 6B and 6C are diagrams each showing a typical configuration of a probe driver employed in the specimen fabrication apparatus provided by the present invention.
Figure 6:
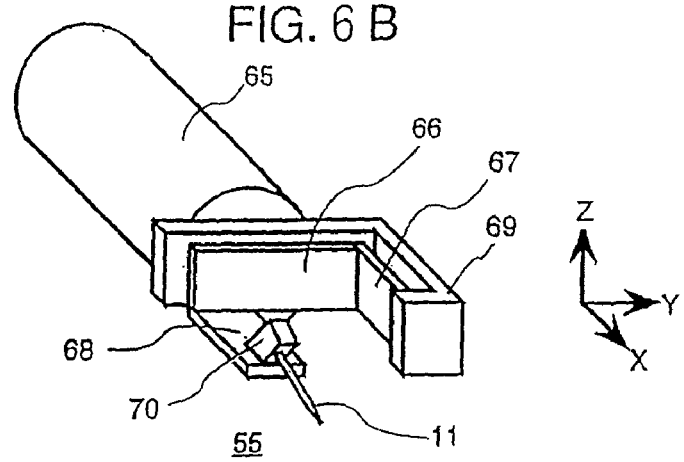
Figure 6:
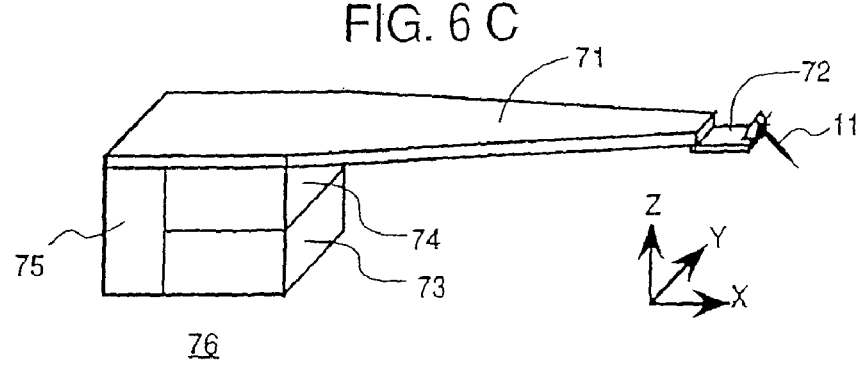

FIGS. 6A, 6B and 6C are diagrams each showing a typical configuration of the probe driver 4. As shown in FIG. 6A, the probe driver 4 is introduced into the inside of the vacuum chamber 77 from the outside thereof through a window 62 on a side wall 54 of the vacuum chamber 77. In this structure, the probe 11 can be moved independently of the sample stage 3 and, in addition, the probe 11 can be moved to the specimen substrate 2 and the TEM-specimen holder 19 with ease.

As shown in FIG. 6A, the probe driver 4 comprises 2 units, namely, a coarse-movement actuator 56 and a fine-movement actuator 55. A coarse movement of the probe 11 driven by the coarse-movement actuator 56 in the X-axial direction of a coarse-movement shaft 65 takes place due to a force which is generated as a result of expanding and shrinking a spring 60 by means of an adjustment screw 57 for sliding a shaft 59. A coarse movement of the probe 11 in the Z-axial direction takes place due to a force which is generated as a result of expanding and shrinking a spring 61 by means of an adjustment screw 58 for swinging the shaft 59 around a supporting point 63. A coarse movement of the probe 11 in the Y-axial direction takes place in accordance with the same principle as the coarse movement in the Z-axial direction except that an adjustment screw for a coarse movement in the Y-axial direction is not shown in the figure. The adjustment screw for a coarse movement in the Y-axial direction is provided at a location in front of this drawing paper. The springs 60 and 61 are used for pressing the shaft 59 against the ends of the adjustment screws 57 and 58 respectively. A spring for a coarse movement in the Y-axial direction which is not shown in the figure is installed in the same way as the spring 61 for a coarse movement in the Z-axial direction. As will be described below, the positional precision of the coarse-movement actuator 56 has a value smaller than the stroke of a fine-movement actuator 55. Required of as compact a design as possible, the fine-movement actuator 55 employs a piezoelectric device. Particularly, in the case of this embodiment, a bimorph-type piezoelectric device is selected. The bimorph-type piezoelectric device offers a merit of a relatively large movement range of at least several hundreds of microns in comparison with piezoelectric devices of other types. On the other hand, since the coarse-movement actuator 56 is not required of a high positional precision, the coarse-movement actuator 56 can be manufactured with ease. In addition, it is sufficient to control the position of the tip of the probe 11 at a micron order. Thus, a bimorph-type piezoelectric device which has a relatively poor resolution in comparison with piezoelectric devices of other types is capable of satisfying this requirement.

FIG. 6B is a diagram showing a typical configuration of the fine-movement actuator 55 employing 3 bimorph-type piezoelectric devices for fine movements in the 3 axial directions respectively in concrete terms. To be more specific, the fine-movement actuator 56 employs bimorph-type piezoelectric devices 66, 67 and 68 for fine movements in the X, Y and Z axial directions respectively as shown in the figure. A probe holder 70 fixes the probe 11 to a 3-axial-direction fine-movement unit, that is, the movement-side end of the bimorph-type piezoelectric device 68. The fixed-side end of the bimorph-type piezoelectric device 67 is firmly joined to a coarse-movement shaft 65 through a fine-movement-unit fixing fixture 69. The bimorph-type piezoelectric devices 66, 67 and 68 can each be driven by applying a simple voltage without requiring a special circuit. By utilizing the bimorph-type piezoelectric devices 66, 67 and 68 in this way, a compact fine-movement actuator 55 offering a large stroke can be realized more economically. A reason why it is necessary to build a compact fine-movement actuator 55 is described as follows.

In the case of a specimen substrate 2 fabricated by using a focused ion beam (FIB) 52 explained earlier by referring to FIG. 5C, the shorter the distance from the objective lens 50 to the specimen substrate 2, the higher the degree to which the fabrication precision can be improved. In addition, in the case of a specimen substrate 2 fabricated by using a projected ion beam (PJIB) 13 explained earlier by referring to FIG. 5A, the shorter the distance from the projection lens 46 to the specimen substrate 2, the greater the value to which the projection magnification of the opening 45 can be increased. That is, in the case of either ion beam in use, it is desirable to have a short distance between the specimen substrate 2 and the lens at the last stage. In consequence, the volumes of the space between the specimen substrate 2 and the lens at the last stage and the surrounding space are limited. In the space surrounding the specimen substrate 2, among other components, the observation means, the secondary-electron detector 12, a deposition-gas supplying nozzle 8 and, in some cases, a nozzle for supplying gas for assist etching are provided. In order to avoid interference with these components, the end of the probe driver 4, that is, the fine-movement actuator 55, has to be made as compact as possible.

Figure 3:
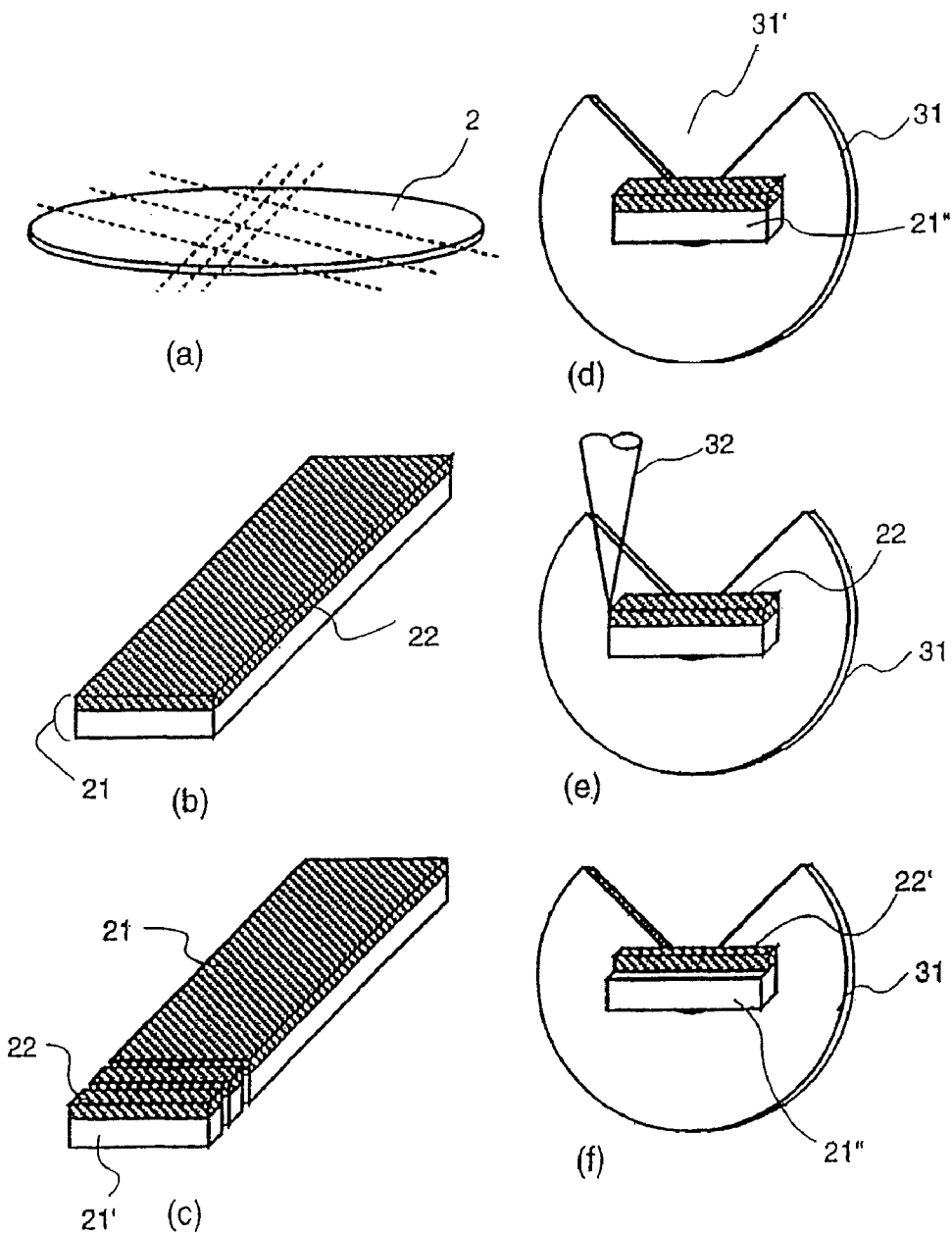
FIG. 3 is process explanatory diagrams showing another example of the conventional method for fabrication of a specimen to be observed by using a TEM.
Figure 4:
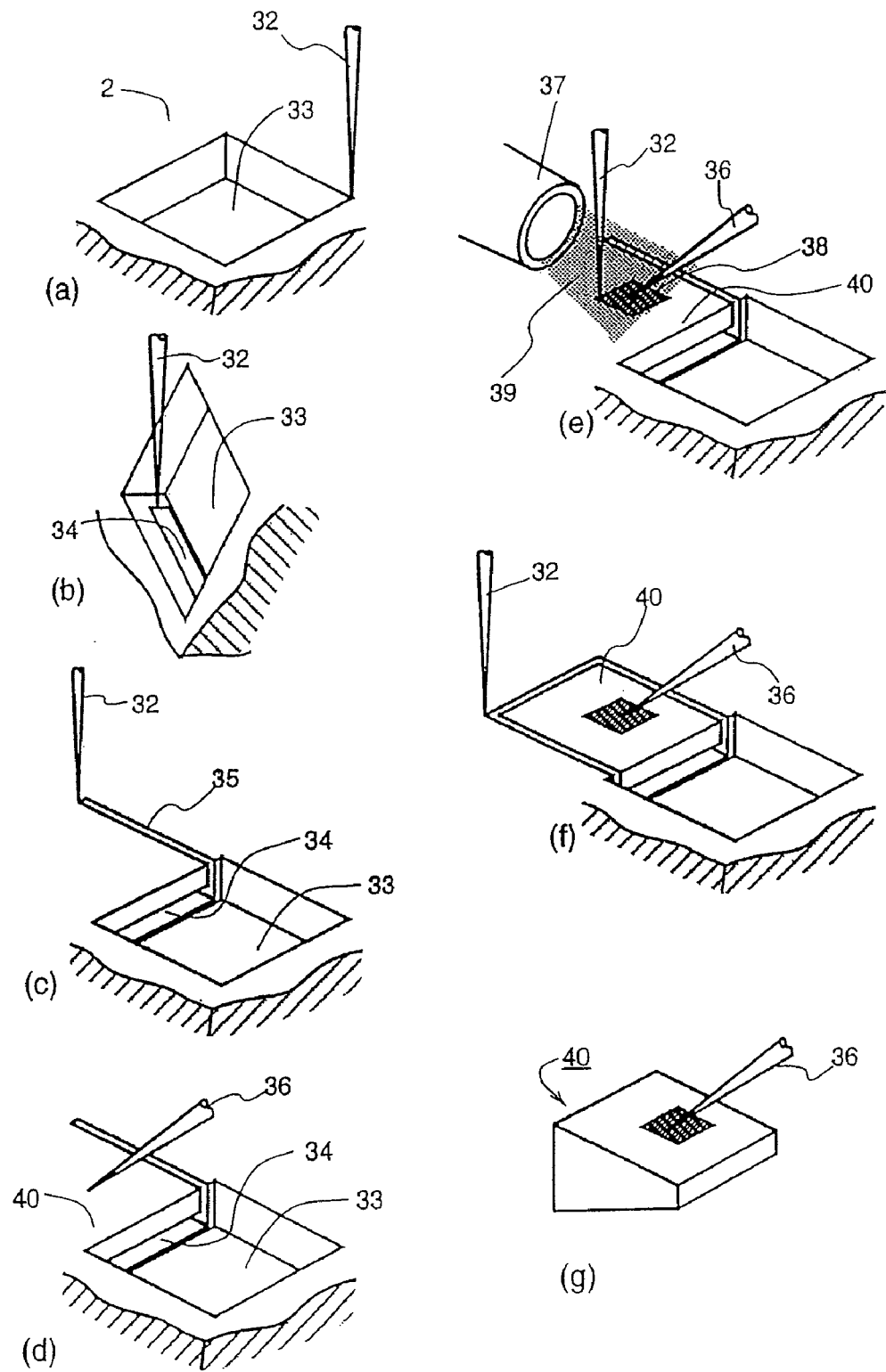
FIG. 4 is process explanatory diagrams showing a further other example of the conventional method for fabrication of a specimen to be observed by using a TEM.

In the conventional technology shown in FIG. 4, the manipulator for conveying a micro-specimen separated from a specimen substrate comprises bimorph-type piezoelectric devices for movements in the 3 axial directions. However, a location at which the manipulator is installed is not clarified. However, the conventional method for fabrication of a specimen of FIG. 3 described in an official report can be interpreted that the manipulator is mounted on the sample stage. With the manipulator mounted on the sample stage, in the case of an area to be observed existing at the center of the wafer, a distance from the installation position of the manipulator to the area to be observed is much longer than the movement stroke of the manipulator. As a result, in the conventional technology whereby the manipulator is mounted on the sample stage, there is raised a fatal problem of an inability to reach such an area to be observed.

On the other hand, the probe driver 4 shown in FIG. 6A is separated away from the sample stage 3 so that, even if an area to be observed exists at the center of a large sample (wafer), the area can be accessed without problems. In addition, when the probe 11 is not in use, the coarse-movement actuator 56 is capable of moving the probe 11 and the fine-movement actuator 55 over a long distance to preserved locations to give no hindrance to other components.

Another typical configuration of the probe driver 4 is shown in FIG. 6C. In this embodiment, a first probe driving mechanism 76 provided with both the coarse-movement and fine-movement functions is sufficiently separated from the sample stage 3. A second probe driving mechanism 72 is attached to the movement-side end of the probe driving mechanism 76 through an extension rod 71. Implemented by a bimorph-type piezoelectric device, the second probe driving mechanism 72 has only the fine-movement function in the Z-axial direction. The probe 11 is firmly fixed to the movement-side end of the second probe driving mechanism 72. In comparison with the configuration shown in FIG. 6B, this configuration offers the following merits. In the case of the configuration shown in FIG. 6B, the probe 11 is driven in the X, Y and Z axial directions by the respective bimorph-type piezoelectric devices. Each of the bimorph-type piezoelectric devices has one end thereof serving as a fixed supporting point and the other end swinging to bend the device. That is, the other end moves along an arc-shaped locus in accordance with an applied voltage. Strictly speaking, in a movement on the XY plane, driven only by 1 bimorph-type piezoelectric device, for example, by the piezoelectric device 66 for movements in the X-axial direction, the tip of the probe 11 does not move in the X-axial direction along a truly straight line, that is, the tip of the probe 11 does not move in the X-axial direction with a high degree of accuracy. Thus, with the fine-movement actuator 55 comprising the 3 bimorph-type piezoelectric devices 66, 67 and 68, in order to move the tip of the probe 11 to a desired location with a high degree accuracy, it is necessary to move each of the 3 bimorph-type piezoelectric devices 66, 67 and 68 by taking the movements of the others into consideration. As a result, there is raised a problem of complex operations to drive the 3 bimorph-type piezoelectric devices 66, 67 and 68 in such a manner that their movements are dependent on each other. In order to solve this problem, it is necessary to employ a probe driving mechanism that is capable of moving the probe 11 along a straight line with a high degree of accuracy. If the probe driving mechanism is also required to have a capability of moving the probe 11 by a long stroke in the range 100 microns to several mm as well as a resolution better than the micron order, the structure of the probe driving mechanism will become complicated and will become big in size in comparison with a bimorph-type piezoelectric device. As a result, a problem of positional interference with other components surrounding the sample stage 3 will remain to be solved.

In the case of the probe driver 4 shown in FIG. 6C, on the other hand, the first probe driving mechanism 76 comprises an X-axial-direction actuator 73, a Y-axial-direction actuator 74 and a Z-axial-direction actuator 75 each having a stroke of about 5 mm and a movement resolution of 0.1 microns to form a structure equipped with both the coarse-movement and fine-movement functions. As described above, a variety of other components coexist in a layout between the lens 46 or 50 provided at the last stage as shown in FIG. 5A or 5C respectively and the substrate. In the configuration of the probe driver 4 shown in FIG. 6C, the probe driver 4 is relieved of contention for space with the other components, allowing a micro-specimen to be extracted and conveyed with ease.

By employing the probe driver 4 described above, the tip of the probe 11 can be positioned on the surface of the specimen substrate 2 at a resolution of the sub-micron order. In addition, since the probe 11 can be moved independently of the sample stage 3 by not mounting the probe driver 4 on the sample stage 3, an access by the tip of the probe 11 to the specimen substrate 2 and the TEM specimen holder 19 can be made with ease.

It is possible to verify the state of joining of the tip of the probe 11 to the surface of the specimen substrate 2, the state of separation of the micro-specimen from the specimen substrate 2, the state of joining of the micro-specimen to the TEM-specimen holder 19 and the state of separation of the TEM-specimen holder 19 from the micro-specimen by detecting changes in voltage contrast of a secondary-electron image obtained from a detection signal generated by the secondary-electron detector 12. These states can also be verified by monitoring a contact resistance between the probe 11 and the sample stage 3 and detecting a change in detected contact resistance.

1-3 [TEM-Specimen Holder]

FIGS. 8A, 8B, 8C and 8D are diagrams each showing a typical configuration of the TEM-specimen holder 19 in concrete terms. The TEM-specimen holder 19 shown in FIG. 8A has a structure wherein a metallic wire 83 is firmly attached to a donut-like fixed unit having a notch 84'. The metallic wire 83 has a diameter in the range 10 to 500 $\mu m\phi$. The fixed unit 84 has dimensions that allow the fixed unit 84 to be mounted on a stage for introducing an ordinary TEM specimen. Such a stage is referred to hereafter as a TEM stage. In this embodiment, the fixed unit 84 has an external diameter of 3 mm$\phi$. Effectiveness of the TEM-specimen holder 19 of the metallic-wire type is explained as follows.

Figure 8:
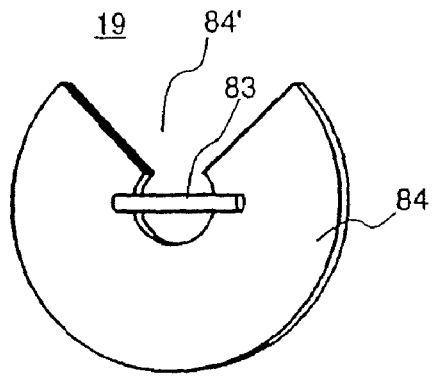
FIGS. 8A, 8B, 8C and 8D are diagrams each showing a typical configuration of a TEM-specimen holder of a metallic-wire type employed in the specimen fabrication apparatus provided by the present invention.
Figure 8:
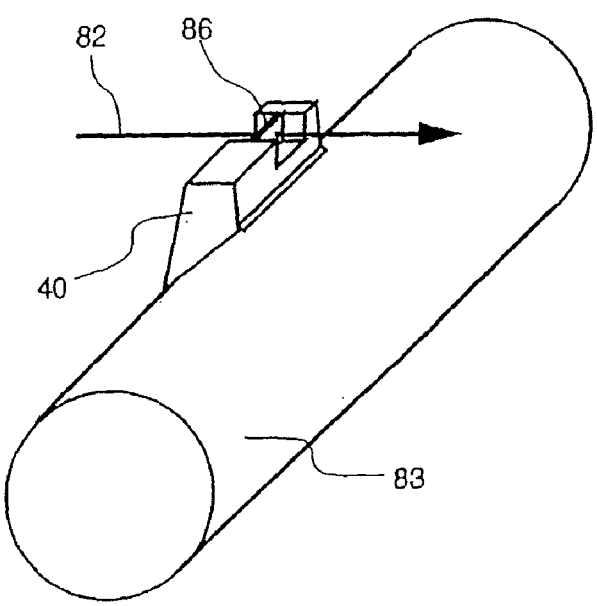
Figure 8:
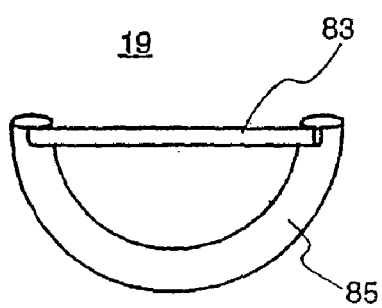
Figure 8:
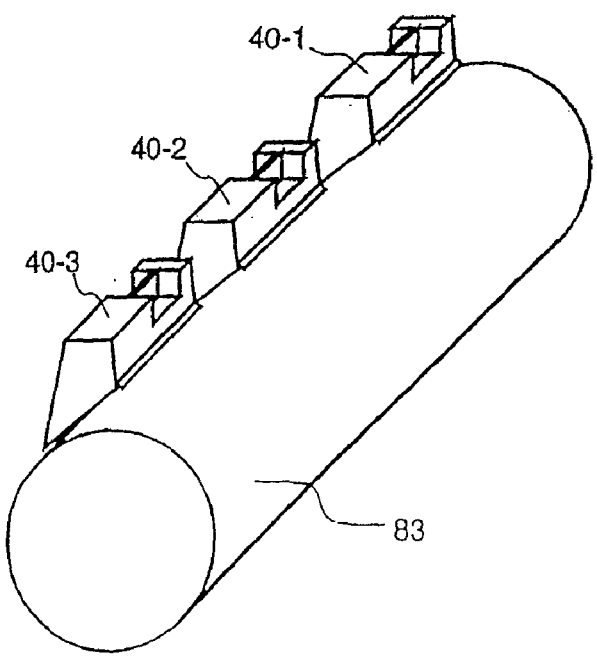

In order to separate a micro-specimen 40 from the specimen substrate 2, it is necessary to separate the bottom surface of the micro-specimen 40 from the specimen substrate 2. Such separation is referred to hereafter as bottom dividing. In the bottom dividing by means of an ion beam, it is necessary to carry out fabrication wherein the ion beam is radiated to the surface of the specimen substrate 2 in slanting direction with respect to the surface. Thus, the bottom surface of the micro-specimen 40 has 2 inclinations, namely, an incident angle of the ion beam radiated during the bottom-dividing and an aspect ratio of fabrication. By using the TEM-specimen holder 19 of the metallic-wire type described above, however, a micro-specimen 40 can be brought into contact with the metallic wire 83 correctly with a cross-sectional surface of a desired observation area 86 oriented perpendicularly as it is even if the micro-specimen 40 has the bottom inclinations. Refer to FIG. 8D. Assume that a micro-specimen 40 with an area of 10 microns×30 microns and a depth of 10 microns is cut out from a specimen substrate 2 by fabrication using an ion beam with the sample stage 3 inclined at an angle of 60 degrees. In this case, the diameter of the metallic wire 83 that does not put a desired observation area 86 under a shadow has a value in the range 40 to 50 $\mu m\phi$. By mounting the micro-specimen 40 on the TEM-specimen holder 19 of the metallic-wire type, a contact portion on the metallic wire 83 between the micro-specimen 40 and the metallic wire 83 can be selected with a high degree of freedom. In addition, an electron beam 82 passing through the desired observation area 86 can be prevented from being shielded by the metallic wire 83 as shown in FIG. 8B.

Also in a TEM-specimen holder 19 of the metallic wire type having a metallic-wire fixing unit 85 as shown in FIG. 8C, the same effects as those described above can be obtained. In addition, by firmly attaching a plurality of micro-specimens 40-1, 40-2 and 40-3 to a metallic wire 83 as shown in FIG. 8D, the same plurality of micro-specimens 40-1, 40-2 and 40-3 can be brought into a TEM at one time to give a merit of an increased efficiency of the observation using a TEM. By using a TEM-specimen holder 19 of the metallic wire type as described above, an infinitesimal micro-specimen can be mounted with ease and the path of an electron beam for observation using a TEM can be prevented from being shielded by the metallic wire 83.

1-4 [Sample Cassette and TEM-Specimen Holder]

Figure 9:
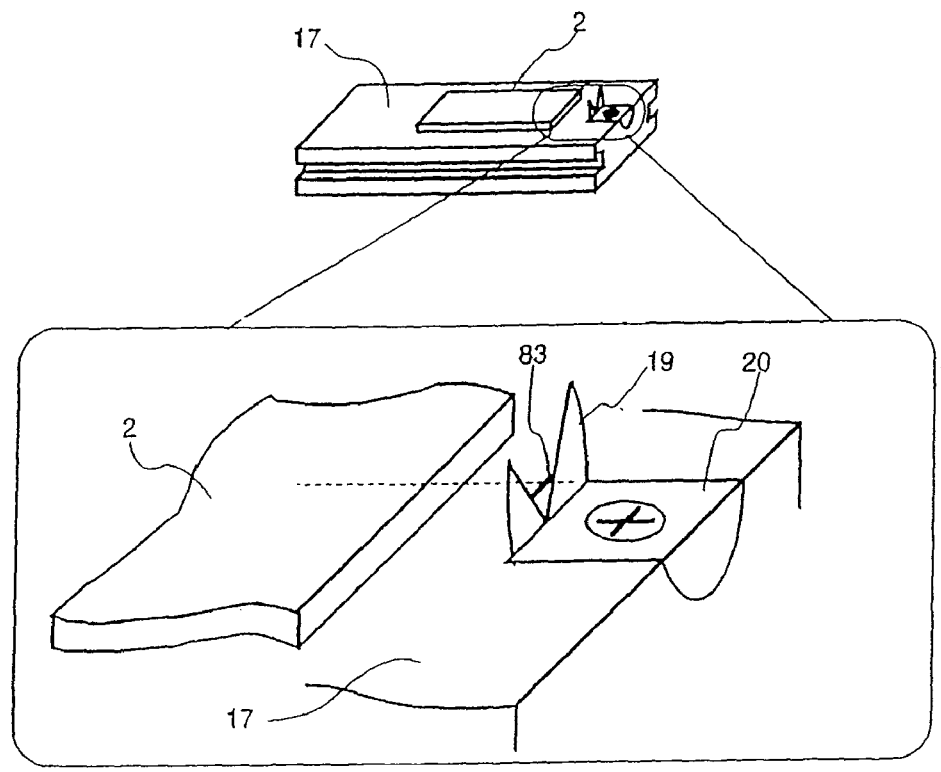
FIGS. 9A and 9B are diagrams showing a typical method of mounting the TEM-specimen holder employed in the specimen fabrication apparatus provided by the present invention on a sample cassette.
Figure 9:
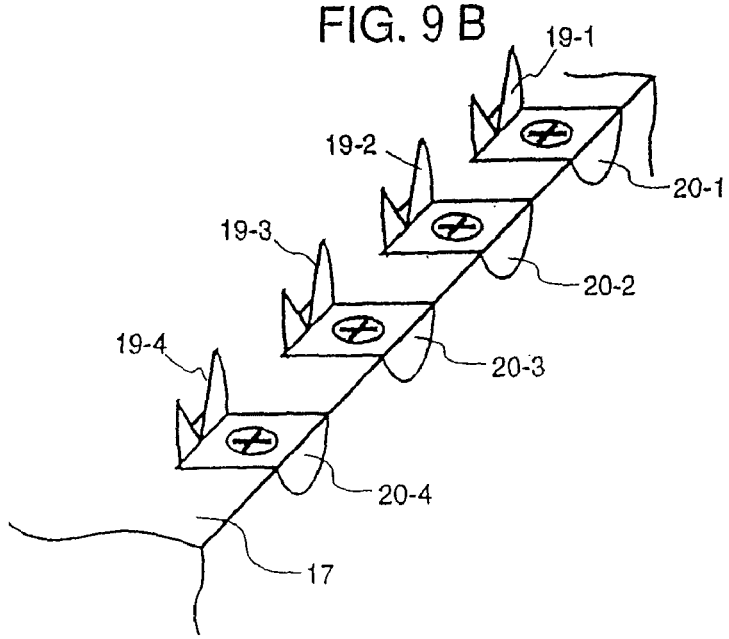

FIGS. 9A and 9B are diagrams each showing a typical configuration for mounting a TEM-specimen holder 19 on a sample cassette 17. In these configurations, the TEM-specimen holder 19 of the metallic-wire type shown in FIG. 8A is used as a TEM-specimen holder 19. FIG. 9A is diagrams showing the entire sample cassette 17 and an enlarged portion of it, that is, a portion enclosed in a dotted-line circle. As shown in the figure, a trench for seating the TEM-specimen holder 19 is created on the sample cassette 17. The TEM-specimen holder 19 is fixed, being sandwiched by the end surface of the trench and the TEM-specimen holder clasp 20. At that time, the TEM-specimen holder 19 is set UP so that the position of the metallic wire 83 employed in the TEM-specimen holder 19 in the perpendicular direction is made close to a position on the surface of the specimen substrate 2 and a position holding a micro-specimen 40 to be extracted is placed at the same level as the surface of the specimen substrate 2. In this posture of the TEM-specimen holder 19, it is not necessary to move the probe 11 much up and down in the Z-axial direction, allowing a high-speed access to a desired location by the probe 11 to be made with ease. In addition, the possibility that an injury is inflicted on the sample can be reduced. In the configuration shown in FIG. 9B, a plurality of trenches 20-1, 20-2, 20-3 and 20-4 for seating TEM-specimen holders 19 are provided on the sample cassette 17. In this configuration, since a plurality of TEM-specimen holders 19-1, 19-2, 19-3 and 19-4 can be mounted on the sample cassette 17 at the same time, a plurality of micro-specimens 40 can be extracted from the same specimen substrate 2 in an operation carried out only once to put the sample chamber 77 in a vacuum state, allowing the efficiency of the specimen fabrication to be further improved.

Figure 10:
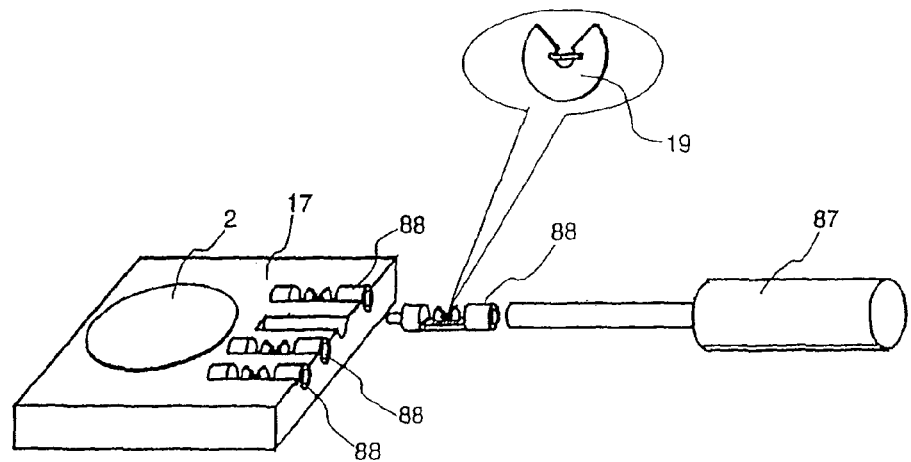
FIG. 10 is a diagram showing a typical method of mounting a TEM-specimen holder cartridge employed in the specimen fabrication apparatus provided by the present invention on a sample cassette.

FIG. 10 is a diagram showing a typical configuration for mounting the TEM-specimen holder 19 on the sample cassette 17. As shown in the figure, on a TEM stage 87, the TEM-specimen holder 19 and peripherals thereof are formed into a holder cartridge 88. A plurality of holder cartridges 88 are mounted on the sample cassette 17. In this configuration, the TEM stage 87 is inserted from the outside of the vacuum chamber 77 through a side entrance and a desired holder cartridge 88 is mounted on the TEM stage 87. The TEM stage 87 can then be introduced into the TEM-specimen chamber with a holder cartridge mounted thereon as it is. In this way, by forming a TEM-specimen holder 19 and peripherals thereof of the TEM stage 87 into a holder cartridge 88, a micro-specimen 40 can now be mounted on a TEM with ease.

1-5 [Probe]

Figure 11:
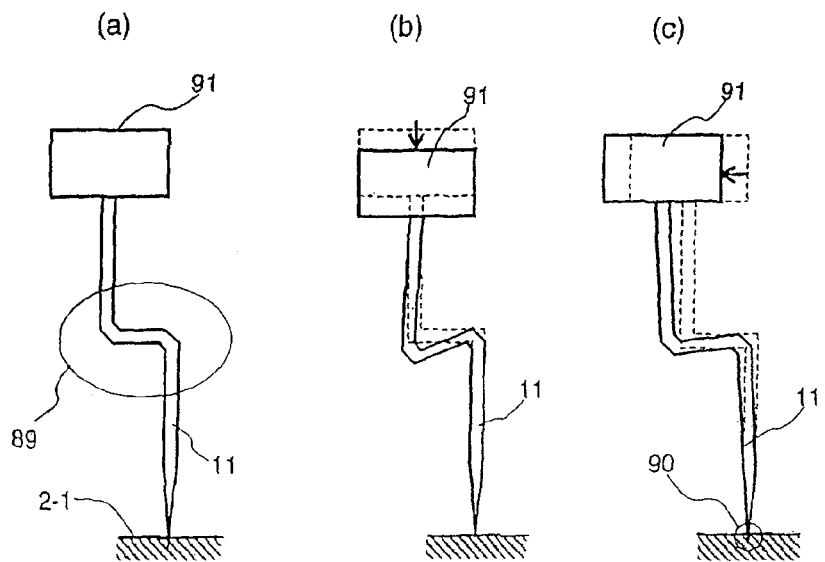
FIG. 11 is explanatory diagrams used for describing a typical configuration and the function of a probe with a spring effect employed in the specimen fabrication apparatus provided by the present invention.

FIG. 11 is explanatory diagrams used for describing a typical configuration of the probe 11. In particular, the figure shows a typical configuration of a probe 11 exhibiting a spring effect. As shown in FIG. 11/(a), at a middle of a long and thin probe 11, a spring-structure portion 89 having a curved shape is provided. In this configuration, when the tip of the probe 11 is brought into contact with a micro-specimen formation area 2-1 on the surface of the specimen substrate 2, an impact force generated between the probe 11 and the micro-specimen formation area 2-1 is absorbed by the spring-structure portion 89, preventing both the tip of the probe 11 and the micro-specimen formation area 2-1 from being injured. In addition, even if the position of a probe holder 91 relative to a contact position 90 changes subtly due to thermal drift or the like after the tip of the probe 11 has been brought into contact with the micro-specimen formation area 2-1, the contact position 90 can be sustained at a stable location by a spring effect of the spring-structure portion 89 as shown for example in FIG. 11/(c).

By using a probe exhibiting a spring effect as described above, an injury can be prevented from being inflicted upon both the probe 11 and the micro-specimen 40. In addition, the posture of the probe 11 can be compensated for a change in position of the probe 11 relative to the micro-specimen 40 caused by thermal drift or the like.

1-6 [Means for Fixing the Tip of the Probe to a Micro-Specimen Formation Area and Separating them from Each Other]

As a method for fixing the tip of the probe 11 to a portion on the specimen substrate 2 to be created as a micro-specimen 40, a technology of creating a deposition film by the IBAD method has been described. On the other hand, a technology of removing the deposition film by the IBS method is adopted as described earlier. Other methods for fixing the tip of the probe 11 to a micro-specimen formation area 2-1 and separating the probe 11 from the micro-specimen 40 are described as follows.

In place of the IBAD method using deposition gas described earlier, the tip of the probe 11 can also be firmly joined to a portion on the specimen substrate 2 to be created as a micro-specimen 40 through a film created by redeposition of ion-beam sputter particles emanating from the specimen substrate 2 on the specimen substrate 2. Such a film is referred to hereafter as a redeposition film. As a method to separate the probe 11 from the micro-specimen 40, a technique of peeling off the redeposition film using the IBS method can be adopted. As an alternative, the probe 11 can also be separated from the micro-specimen 40 by cutting off the probe 11 by using the IBS method.

As another alternative, adhesive is applied to the surface of the tip of the probe 11 in advance and then, by merely bringing the tip of the probe 11 into contact with a micro-specimen formation area 2-1, the tip of the probe 11 can be firmly joined to the micro-specimen formation area 2-1. Unlike the a technique of using a deposition film by adoption of the IBAD method described earlier, this other-alternative method offers a merit that the length of time it takes to carry out the work of joining the tip of the probe 11 to the micro-specimen formation area 2-1 can be reduced. As the adhesive, it is possible to use UV-ray exfoliative adhesive, the sticking power of which can be reduced by irradiation of an ultraviolet ray thereto. If such adhesive is used, the probe 11 can be separated from the micro-specimen 40 by using an ultraviolet-ray radiating means. In this case, however, a capability of radiating an ultraviolet ray to the contact portion is required as a condition. Thus, such adhesive can not be used under a condition wherein an ultraviolet ray is shielded. As an alternative, it is also possible to use heating-exfoliative adhesive, the sticking power of which can be reduced by heat, as adhesive for sticking the tip of the probe 11 to the micro-specimen formation area 2-1. In this case, the probe 11 can be separated from the micro-specimen 40 by using a heating means. In an example shown in FIG. 12, an electricity path 92 is provided in the vicinity of the probe 11 for heating the probe 11 by Joule's heating to a temperature in the range 80 to 100 degrees Celsius. In this way, the heating-exfoliative adhesive can be peeled off with ease.

Figure 13:
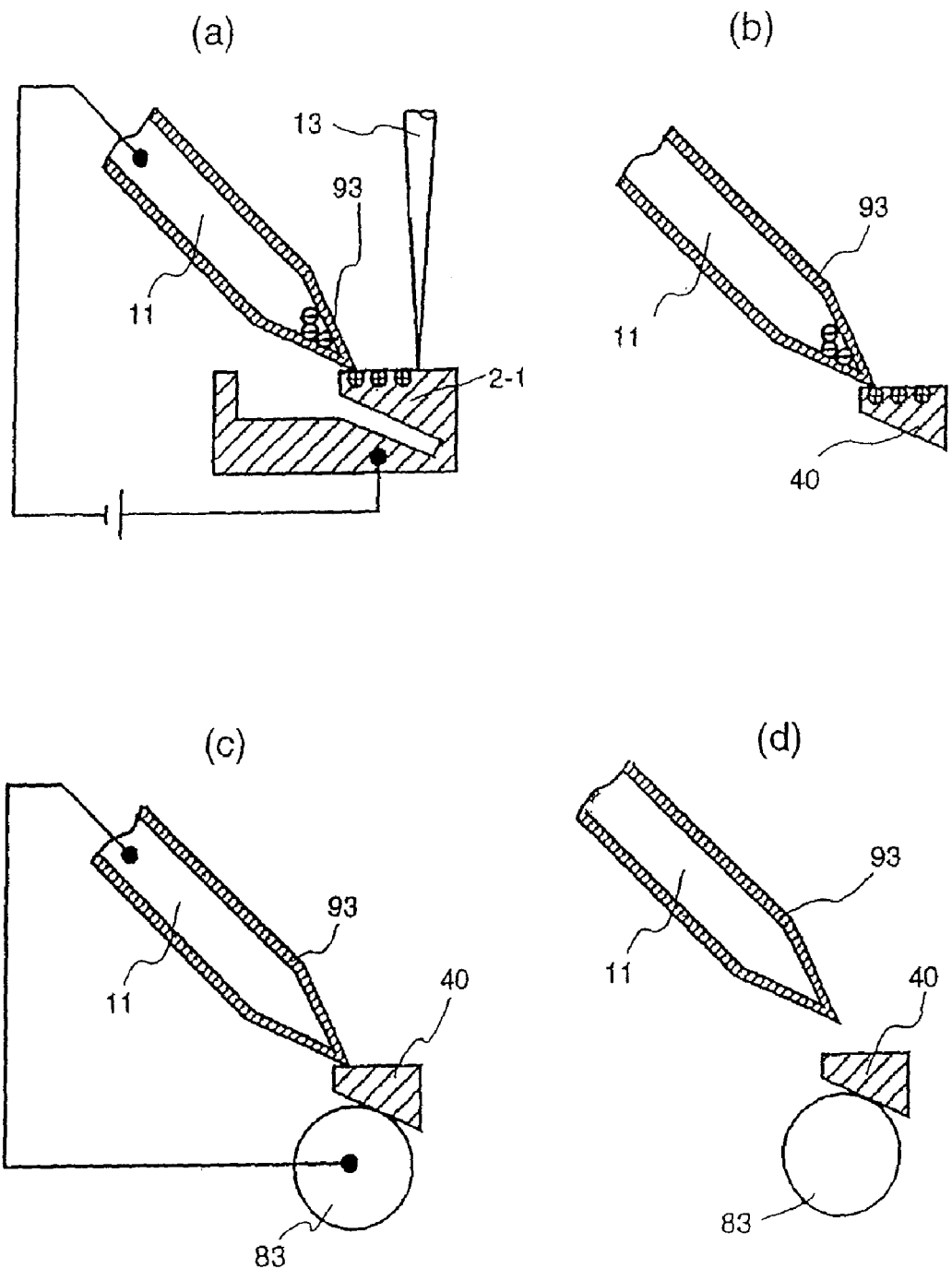
FIG. 13 is diagrams showing an example of a method of junction based on a technique of electrostatic absorption between the probe and a micro-specimen in the specimen fabrication apparatus provided by the present invention.

FIG. 13 is diagrams showing another example of a method of firmly joining the probe 11 to a micro-specimen 40. As a technique of fabricating a specimen, the IBS method of using an ion beam 13, strictly speaking, a positive ion beam 13, is adopted. In this case, according to the method shown in FIG. 13, the probe 11 is fixed to a micro-specimen formation area 2-1 and separated from a micro-specimen 40 by using an electrostatic absorption technique. To put it in detail, first of all, the surface of the probe 11 is covered by an insulating material 93. An electric-potential difference is then applied between the probe 11 and the micro-specimen formation area 2-1 to generate a force of electrostatic absorption for firmly joining the probe 11 to the micro-specimen formation area 2-1. This method has a merit of no accompanying chemical change in quality and no accompanying contamination. Here, the reason why the micro-specimen formation area 2-1 is charged with positive electric charge as shown in FIG. 13/(a) is to prevent the area 2-1 from being neutralized by the positive ion beam 13. If a negative ion beam or an electron beam is irradiated, on the other hand, it is necessary to charge the micro-specimen formation area 2-1 with negative electric charge instead. In this state, the tip of the probe 11 can be firmly joined to the micro-specimen 40 as shown in FIG. 13/(b). The micro-specimen 40 firmly joined to the tip of the probe 11 is then conveyed to the TEM-specimen holder 19 to be fixed to the metallic wire 83 of the TEM-specimen holder 19. A method to fix the micro-specimen 40 to the metallic wire 83 will be described later. After the micro-specimen 40 has been fixed to the metallic wire 83, the probe 11 and the metallic wire 83 are short-circuited as shown in FIG. 13/(c) to neutralize the micro-specimen 40 from the electric charge charged therein. The neutralization of the electric charge allows the tip of the probe 11 to be separated from the micro-specimen 40 as shown in FIG. 13/(d).

Figure 12:
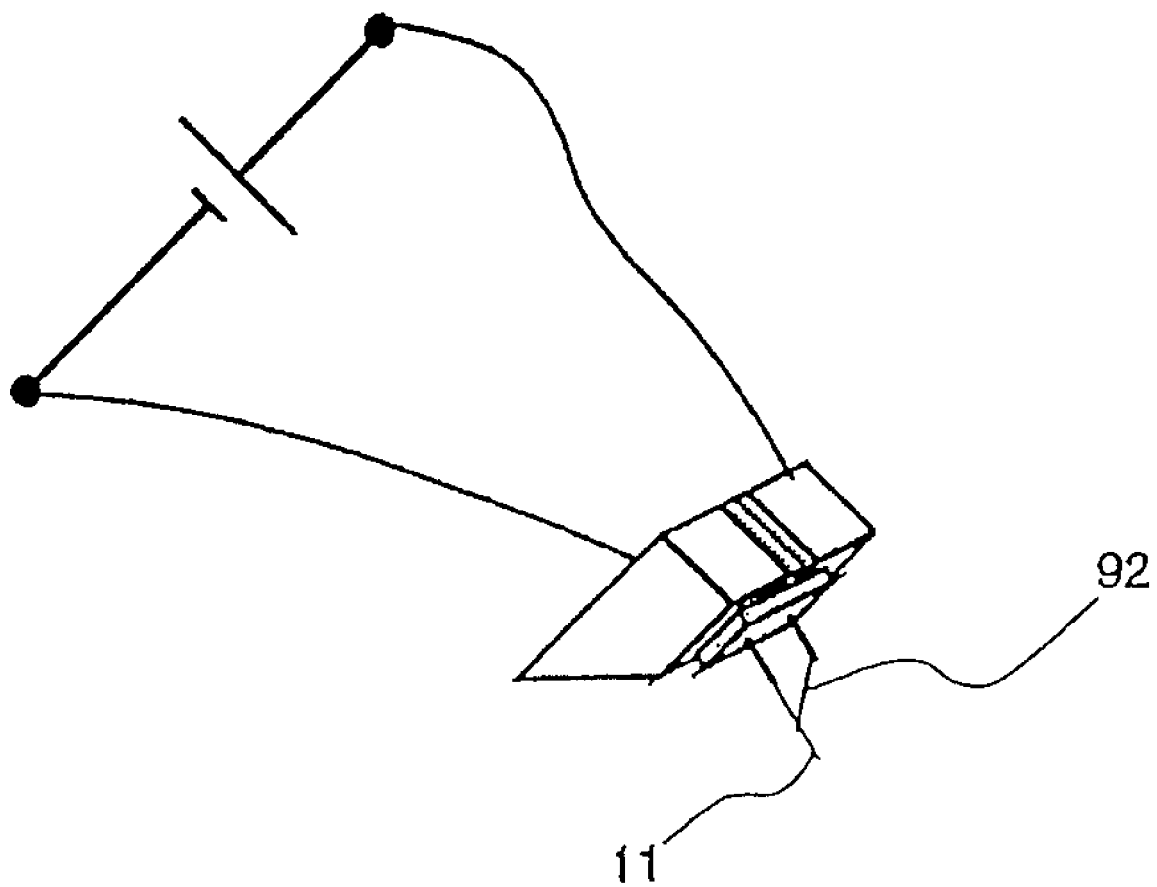
FIG. 12 is a diagram showing an example of a method to heat a probe in the specimen fabrication apparatus provided by the present invention.

As an alternative, the probe 11 is heated by using a Joule's heating method, that is, a method similar to that shown in FIG. 12, or a heating method by local laser irradiation. Then, the tip of the probe 11 is fixed to the micro-specimen formation area 2-1 by fusion caused by a thermal reaction of the tip in contact with the micro-specimen formation area 2-1. However, it is quite within the bounds of possibility that the high-temperature heating of the whole of the micro-specimen formation area 2-1 changes the quality of the micro-specimen 40 itself. It is thus necessary to locally heat the micro-specimen formation area 2-1 in a short period of time.

As is generally known, by merely bringing 2 metals each having a clean surface into contact with each other, a junction can be formed between the two metals. Thus, for example, the tip of a metallic probe 11 made of typically tungsten can be firmly joined to a contact portion of the micro-specimen formation area 2-1 as follows. First of all, their surfaces are each cleaned in a surface sputtering process by irradiation of an ion beam in a vacuum chamber. Then, the tip of the metallic probe 11 is firmly joined to the contact portion of the micro-specimen formation area 2-1 through a metallic junction between them. In addition, a junction can be created by such surface cleaning between 2 pieces of silicon. Thus, in the case of a silicon sample, the tip of the probe 11 can be firmly joined to the micro-specimen formation area 2-1 by the same process provided that the probe 11 is also made of silicon.

1-7 [Means for Fixing a Micro-Specimen to the TEM-Specimen Holder]

Figure 14:
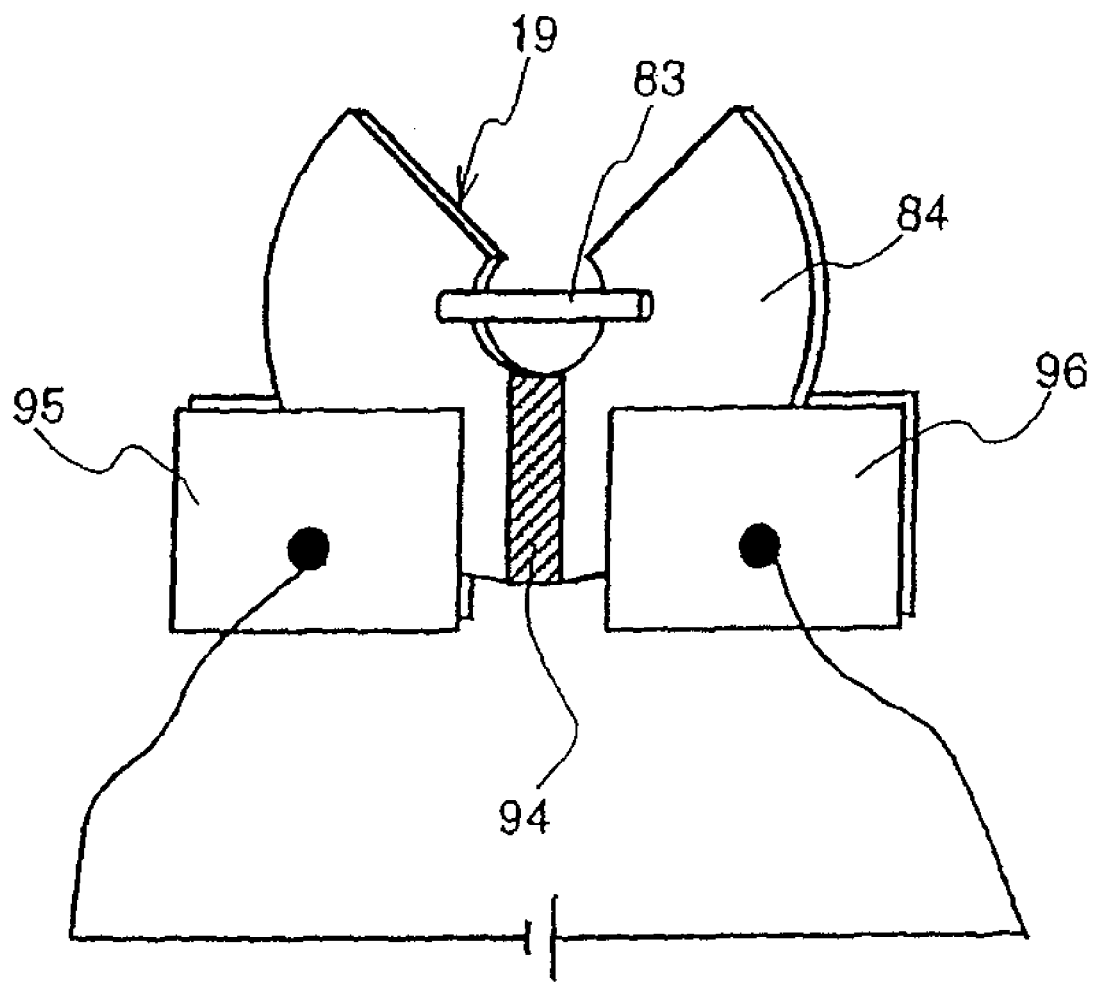
FIG. 14 is a diagram showing an example of a method to heat a TEM-specimen holder in the specimen fabrication apparatus provided by the present invention.

FIG. 14 is a diagram showing another example of a method to fix a micro-specimen 40 to the TEM-specimen holder 19. In this example, a micro-specimen 40 can be firmly joined to the TEM-specimen holder 19 by heating a contact portion between the micro-specimen 40 and the TEM-specimen holder 19. As shown in the figure, the fixed unit 84 of the metallic wire 83 employed in the TEM-specimen holder 19 is divided into 2 portions and an insulator 94 is placed between these 2 portions. By flowing a current between holder support electrodes 95 and 96. Joule's heat is generated to raise the temperature of the metallic wire 83. Then, by bringing a fixed member of the micro-specimen 40 into contact with the heated metallic wire 83, the fixed member of the micro-specimen 40 can be firmly joined to the metallic wire 83 by fusion.

The micro-specimen 40 can also be firmly joined to the TEM-specimen holder 19 by the IBAD method using a deposition film or the IBS method using a redeposition film described earlier. When a micro-specimen 40 is fixed to the TEM-specimen holder 19 by using adhesive, unlike the case in which the tip of the probe 11 is joined to the micro-specimen 40 only temporarily, it is necessary to firmly fix the micro-specimen 40 to the TEM-specimen holder 19 in a stable state which lasts for a long period of time, at least till an observation by using a TEM is completed. It is thus desirable to use adhesive that has a strong sticking power.

As another method of fixing the micro-specimen 40 to the TEM-specimen holder 19, the surfaces of a contact portion between the micro-specimen 40 and the TEM-specimen holder 19 on both sides is cleaned to create a junction between the micro-specimen 40 and the TEM-specimen holder 19 by bringing the surfaces into contact with each other. The surfaces can be cleaned by using typically an ion-sputter method.

1-8 [Extraction of a Micro-Specimen by Ion-Beam Fabrication]

In order to separate a micro-specimen 40 from a specimen substrate 2, the bottom-dividing process technology described earlier is required.

In a first method, an ion beam (PJIB) generated by a PJIB irradiating optical system is used as a fabrication beam as shown in FIG. 1. The sample stage 3 is inclined so that the PJIB is irradiated to the surface of the specimen substrate 2 in a slanting direction with respect to the surface in order to carry out a desired bottom-dividing fabrication. This first method is the same as the method explained earlier by referring to FIG. 4 or the method explained thereafter by referring to FIG. 17.

In a second method, an ion beam (FIB) is used as a fabrication beam as shown in FIG. 5C. Much like the first method, the sample stage 3 is inclined so that the FIB is irradiated to (strictly speaking, driven in a scanning operation to sweep over) the surface of the specimen substrate 2 in a slanting direction with respect to the surface in order to carry out a bottom-dividing fabrication to extract a micro-specimen 40.

Figure 15:
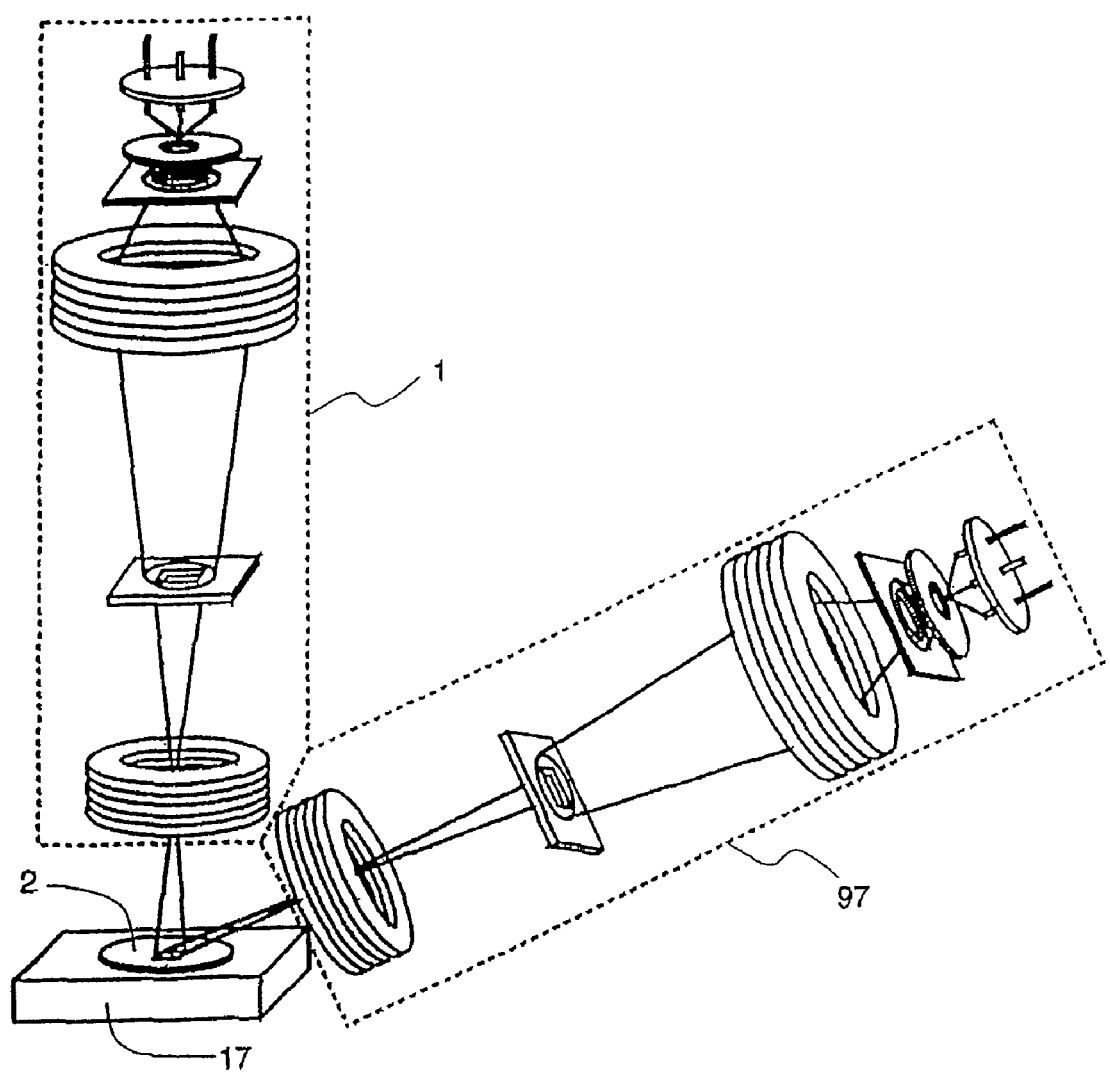
FIG. 15 is a diagram showing another example of the configuration of the specimen fabrication apparatus provided by the present invention.

According to a third method, there are provided a first PJIB irradiating optical system 1 (column I) for making a trench with perpendicular side walls on the surface of the specimen substrate 2 and a second PJIB irradiating optical system 97 (column II) which is oriented in a slanting direction and used for performing the bottom-dividing fabrication described above as shown in FIG. 15. To be more specific, column II is used for carrying out a desired bottom-dividing fabrication. As column II oriented in a slanting direction, an FIB irradiating optical system can be employed in place of a PJIB irradiating optical system.

Figure 16:
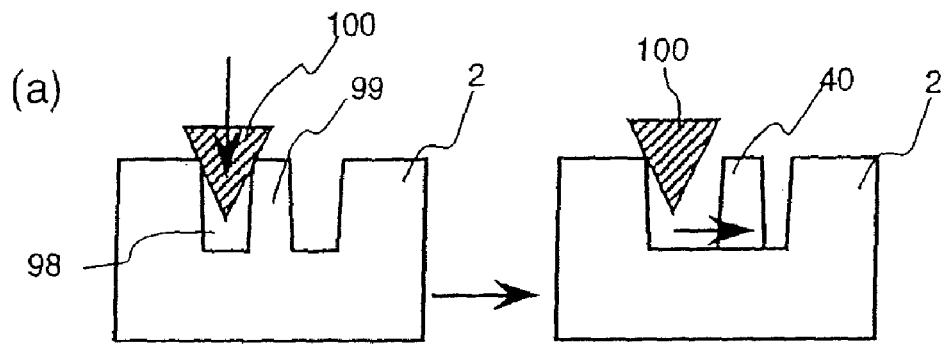
FIG. 16 is diagrams showing typical methods to separate a micro-specimen in another example of the configuration of the specimen fabrication apparatus provided by the present invention.
Figure 16:
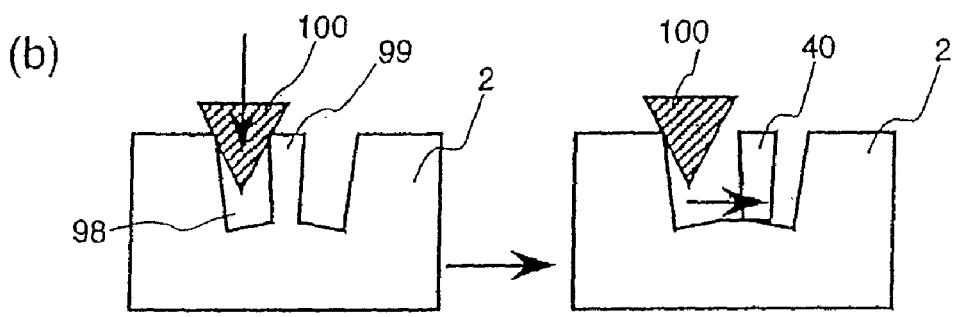
Figure 16:
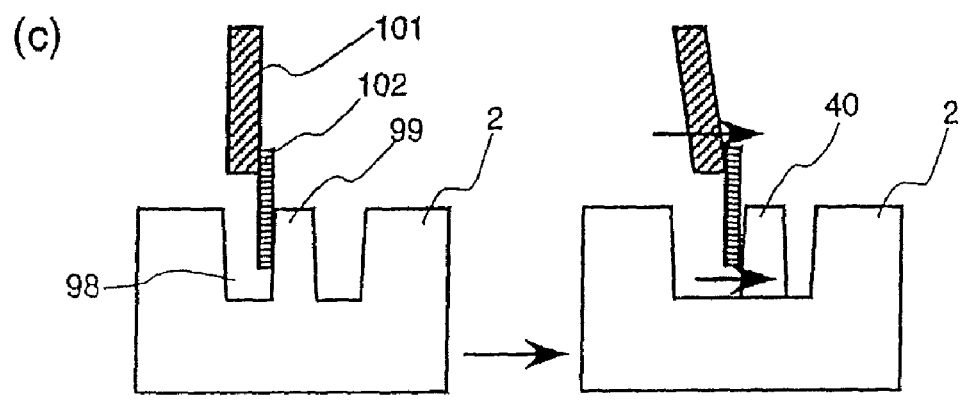

A fourth method shown in FIG. 16 is a bottom-dividing method that does not use an ion beam. As shown in FIG. 16/(a), first of all, trenches 98 are created around a desired observation area on the surface of the specimen substrate 2 by ion-beam fabrication to form a protruding micro-specimen formation portion 99. Then, a wedge 100 is inserted into the trench 98 on one side of the micro-specimen formation portion 99 to separate a micro-specimen 40 by a shearing force. In comparison with the bottom-dividing fabrication methods using an ion beam as described above, the fourth method has a merit that the bottom-dividing fabrication can be completed in a short period of time. In order to make the separation by a shearing force easy to accomplish, the trenches 98 are created around a micro-specimen formation portion 99 in such a slightly slanting direction that the more we look into the inner side of the specimen substrate 2, the thinner the cross section of the micro-specimen formation portion 99 as shown in FIG. 16/(b). As an alternative, an infinitesimal plate 102 attached to a piezoelectric device 101 is inserted into the inside of the trench 98 as shown in FIG. 16/(c). Then, by actuating the piezoelectric device 101, a force is applied to the micro-specimen formation portion 99 in the transversal direction, separating a micro-specimen 40 by shearing.

By carrying out a bottom-dividing fabrication as described above, an infinitesimal micro-specimen 40 with a small depth can be created on the upper portion of the specimen substrate 2. As a result, the fabrication can be completed in a shorter period of time. In particular, by adopting the shearing separation method in the bottom-dividing fabrication, a micro-specimen 40 can be separated and extracted at a high speed.

Second Embodiment

Figure 17:
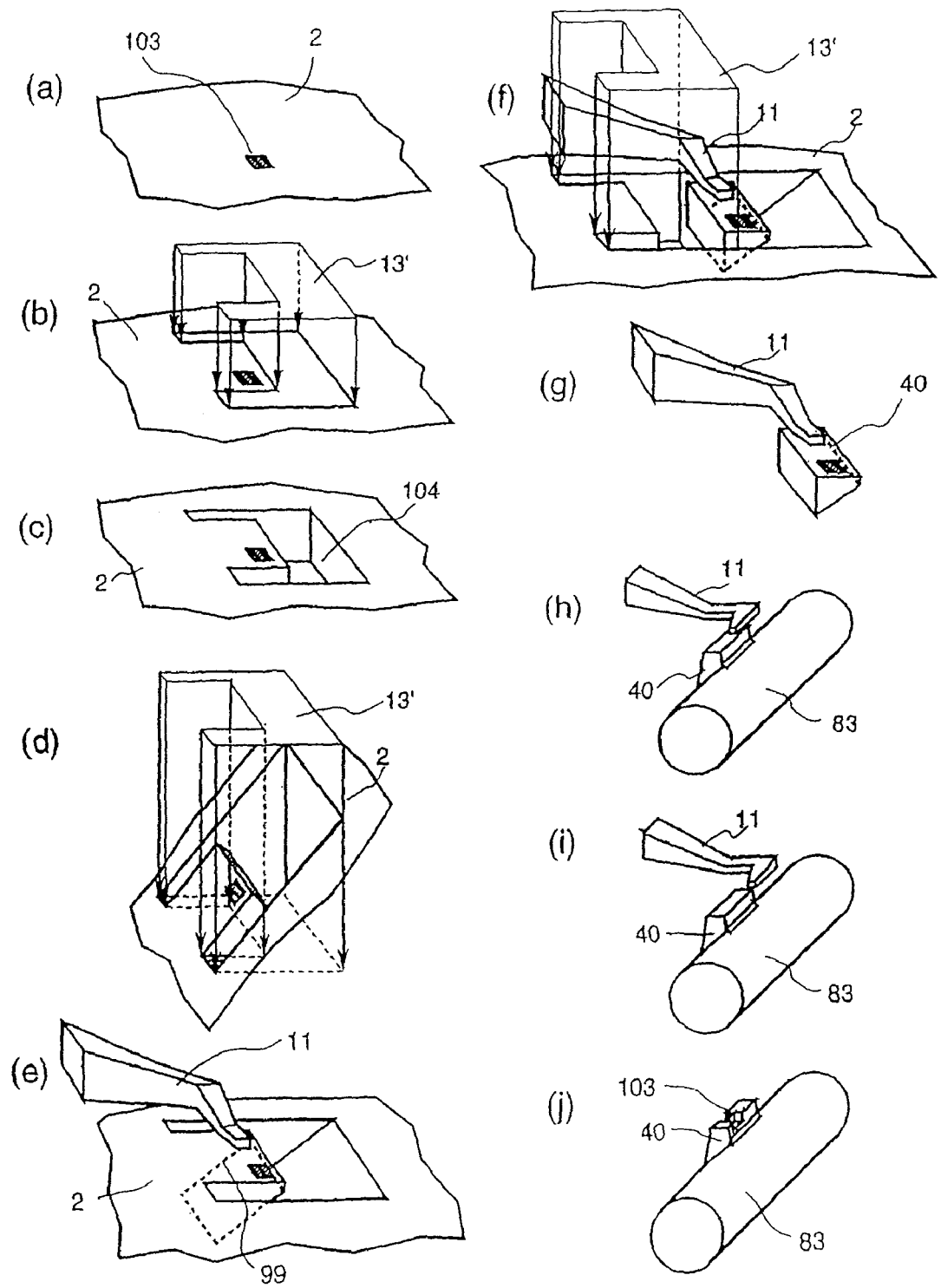
FIG. 17 is process explanatory diagrams showing another embodiment of the present invention for implementing a method for fabrication of a TEM specimen.

FIG. 17 is process explanatory diagrams showing another embodiment of the present invention for implementing a method for fabrication of a TEM specimen. The method is adopted in the specimen fabrication apparatus shown in FIG. 1 and only a PJIB is used as an ion beam for fabrication.

First of all, a PJIB 13' is irradiated to regions surrounding an observation area 103 on the specimen substrate 2 shown in FIG. 17/(a) by using a mask with a shape resembling a symbol ']' as shown in FIG. 17/(b) to form a trench 104 having a bottom with a shape resembling the ']' symbol as shown in FIG. 17/(c). Then, the sample stage 3 shown in FIG. 1 is inclined to carry out a bottom-dividing fabrication by means of the PJIB 13' as shown in FIG. 17/(d). Subsequently, the tip of the probe 11 held by the probe driver 4 is brought into contact with a micro-specimen formation portion 99. The state of contact between the tip of the probe 11 and the micro-specimen formation portion 99 can be verified by detection of, among other phenomena, a variation in contact resistance between the probe 11 and the specimen substrate 2, that is, the micro-specimen formation portion 99, or a variation in voltage contrast on a secondary-electron image. The tip of the probe 11 brought into contact with the micro-specimen formation portion 99 is then firmly joined to the micro-specimen formation portion 99 by using a deposition film created by adoption of the IBAD method as shown in FIG. 17/(e). Then, a micro-specimen 40 is cut out from the specimen substrate 2 by irradiating the ion beam PJIB 13' to the remaining sides of the micro-specimen 40 as shown in FIG. 17/(f). The fact that the probe 11, that is, the micro-specimen 40, has been separated from the specimen substrate 2 is verified by detection of, among other phenomena, an increase in contact resistance between the probe 11 and the specimen substrate 2 or a variation in voltage contrast on a secondary-electron image. The micro-specimen 40 separated from the specimen substrate 2 is then conveyed to the TEM-specimen holder 19 by the probe driver 4 as shown in FIG. 17/(g). Subsequently, the micro-specimen 40 separated from the specimen substrate 2 is brought into contact with the metallic wire 83 of the TEM-specimen holder 19 as shown in FIG. 17/(h). The state of contact between the micro-specimen 40 firmly joined to the probe 11 and the metallic wire 83 of the TEM-specimen holder 19 is verified by detection of a decrease in contact resistance between the probe 11, that is, the micro-specimen 40, and the TEM-specimen holder 19, that is, the metallic wire 83, or a variation in voltage contrast on a secondary-electron image. After the micro-specimen 40 has been brought into contact with the metallic wire 83, the former is firmly joined to the latter by using a deposition film created by adoption of the IBAD method. After the micro-specimen 40 has been firmly joined to the metallic wire 83, a PJIB or an FIB is irradiated to a contact portion between the tip of the probe 11 and the micro-specimen 40 to carry out a sputtering fabrication for separating the tip of the probe 11 from the micro-specimen 40 as shown in FIG. 17/(i). The fact that the tip of the probe 11 has been separated from the micro-specimen 40 is by detection of an increase in contact resistance between the probe 11 and the metallic wire 83 or a variation in voltage contrast on a secondary-electron image. Finally, the PJIB or the FIB is again irradiated to the micro-specimen 40 to carry out a thinning finishing process to thin the observation area 103 to a final thickness of about 100 nm or smaller in order to produce a TEM specimen as shown in FIG. 17/(j).

As described above, this embodiment is exemplified by a method for fabrication of a specimen subjected to an observation using a TEM. It should be noted that, of course, this method can be adopted for fabrication of a specimen for other types of observation, a specimen for analyses and a specimen for measurements. In this case, the finishing process for thinning the area to be observed shown in FIG. 17/(j) is not necessarily required.

Methods for fabrication of a specimen provided by the present invention are not limited to the embodiments described above. It is needless to say that other apparatuses and technological means can be combined. For example, in the process of carrying out a bottom-dividing fabrication shown in FIG. 17/(d), any of the 4 methods described above can be adopted. The method for firmly joining the tip of the probe 11 to a micro-specimen formation portion 99 and the method for separating the tip of the probe 11 from a micro-specimen 40 can be replaced by the other methods described above. In addition, the shape of the PJIB 13' used for formation of a micro-specimen 40 is not limited to the shape resembling the ']' symbol used in the embodiment described above. For example, a combination of a plurality of PJIB projections each having a rectangular pattern can be adopted to produce a similar pattern of fabrication. As an alternative, a PJIB with a rectangular pattern is moved in a scanning operation to sweep the surface of the specimen substrate 2 to produce a desired pattern. In addition, an FIB can be used in place of a PJIB. Furthermore, a PJIB irradiating optical system 1 can be employed in an apparatus for fabrication of a specimen in conjunction with an FIB irradiating optical system 1 so that either of the optical systems can be selected in dependence of the purpose of the fabrication. Last but not least, the ion-beam sputtering fabrication method can be adopted in conjunction with the laser-beam fabrication method to carry out the separation fabrication.

Third Embodiment

Figure 18:
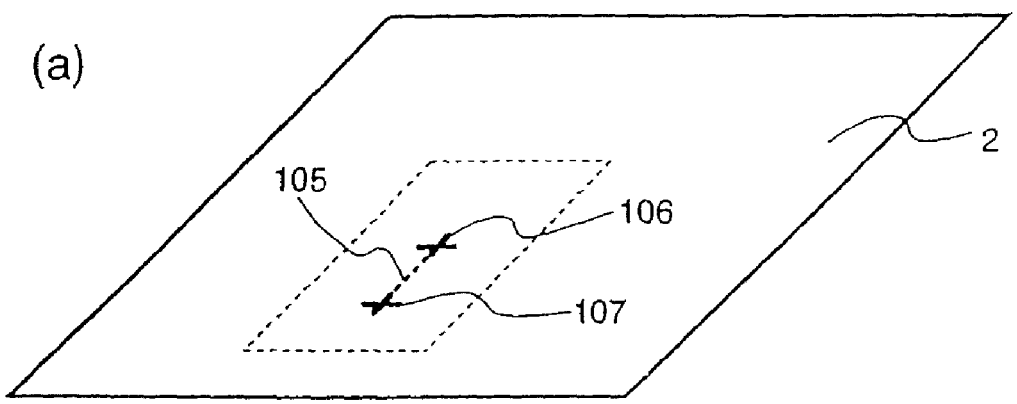
FIG. 18 is process explanatory diagrams showing a further other embodiment of the present invention for implementing a method for fabrication of a TEM specimen.
Figure 18:
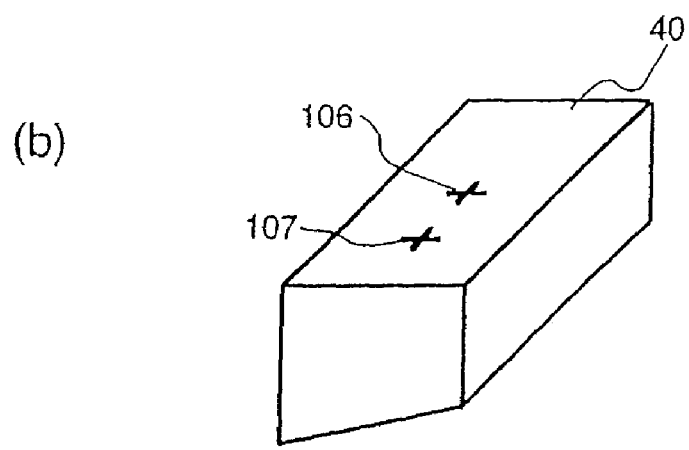
Figure 18:
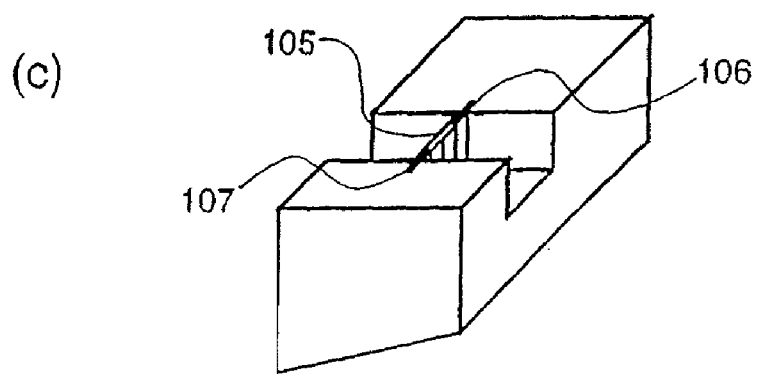

FIG. 18 is process explanatory diagrams showing a further other embodiment of the present invention for implementing a method for fabrication of a TEM specimen. In this embodiment, a marking process for clarifying a specific position 105 on a micro-specimen 40 to be observed or analyzed is added to the methods for fabrication the micro-specimen 40 described earlier. It should be noted that, since the other processes in this third embodiment are virtually the same as those shown in FIG. 17, their explanation with reference to diagrams is not repeated. In this embodiment, in order to avoid the observation location 105 from being no longer unidentifiable after the micro-specimen 40 including a specific location 105 to be observed has been extracted from the specimen substrate 2, a process to put a mark on the observation location 105 is added in order to clearly show the observation location 105. The observation location 105 is a specific location at which a thin wall portion for observations by using a TEM is to be created. When the specimen substrate 2 is still in a wafer or chip state prior to the specimen fabrication, a position on the specimen substrate 2 can be found from information such as CAD data. That is why a mark is put on the observation location (the thin-wall formation location) 105 prior to the fabrication to extract the micro-specimen 40. In the marking process, cross marks 106 and 107 are typically put on both the ends of the observation location 105 by fabrication using an ion beam or the like as shown in FIG. 18/(a). The cross marks 106 and 107 allow the observation location 105 to be recognized clearly as shown in FIG. 18/(b) even after the micro-specimen 40 has been extracted from the specimen substrate 2. Then, a thin wall is formed by leaving a portion coinciding with a straight line connecting the marks 106 and 107 to each other, that is, the observation location 105 as shown in FIG. 18/(c). As a result, a cross section at a desired location can be observed. As described above, by virtue of the additional marking process, a location to be observed can be identified with a high degree of accuracy even after an infinitesimal micro-specimen 40 has been created. It should be noted that, in order to protect the observation location 105, a deposition film is created in advance on the surface of the micro-specimen 40 prior to the marking process.

Fourth Embodiment

Figure 19:
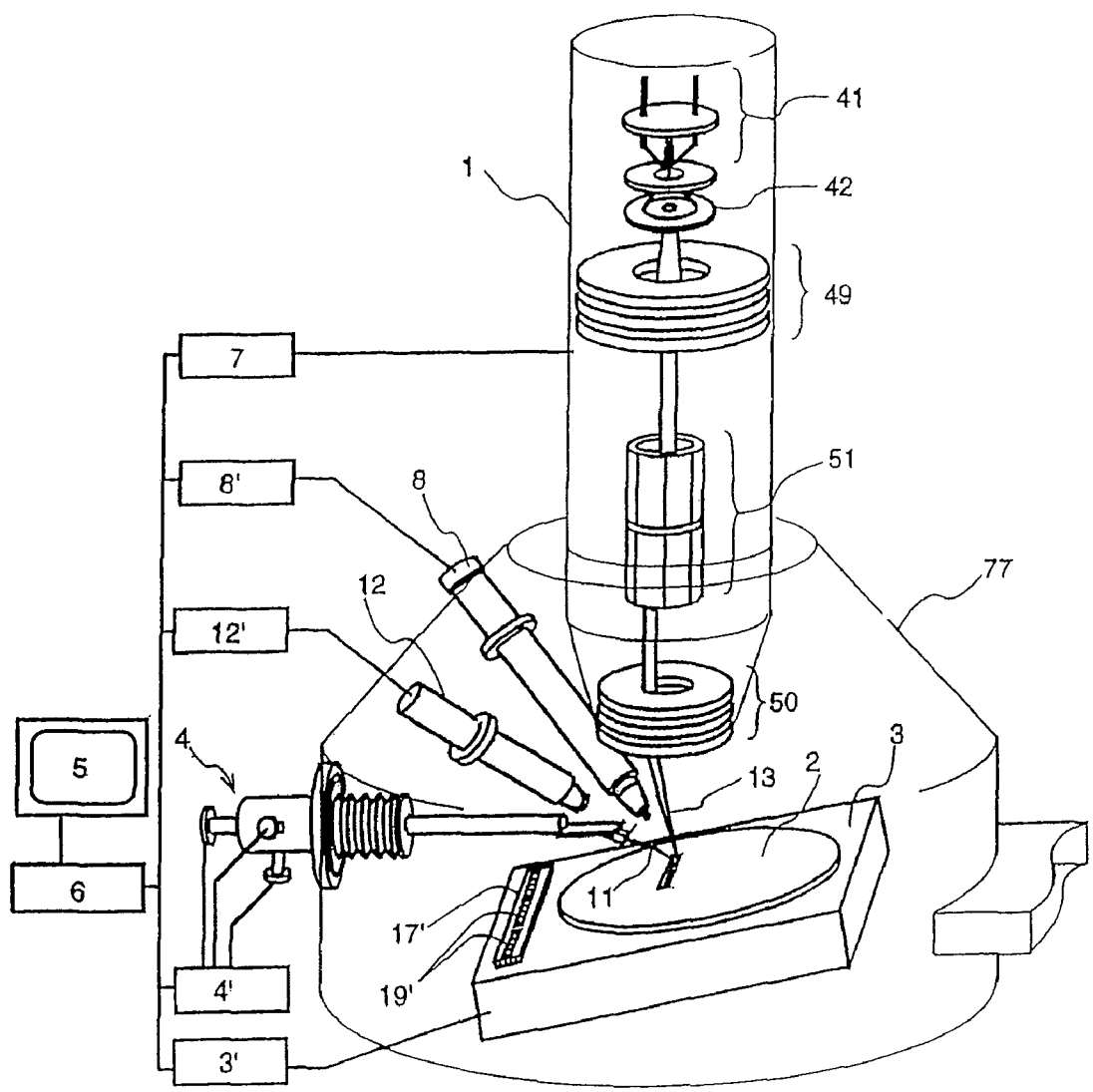
FIG. 19 is a diagram showing the basic configuration of a specimen fabrication apparatus as implemented by another embodiment of the present invention.

FIG. 19 is a diagram showing a configuration of the basic specimen fabrication apparatus as implemented by another embodiment of the present invention in a simple and plain manner. As shown in the figure, the specimen fabrication apparatus implemented by this embodiment comprises at least, a movable sample stage 3 on which a specimen substrate 2 is mounted, an FIB (focused ion beam) irradiating optical system 1 for irradiating a focused ion beam (FIB) 13 to the surface of the specimen substrate 2;

a secondary-particle detector 12 for detecting secondary particles such as secondary electrons and secondary ions emitted by the surface of the specimen substrate 2 due to irradiation of the FIB 13 to the surface;

a deposition-gas supplying source 8 for supplying deposition gas, that is, gas used for formation of a deposition film, to an area on the surface of the specimen substrate 2 to which the FIB 13 is irradiated;

a TEM-specimen holder 19' for firmly holding a micro-specimen 40 extracted from the specimen substrate 2;

a holder cassette 17' for holding the TEM-specimen holder 19'; and a specimen transferring unit 4 for transferring the micro-specimen 40 extracted and separated from the specimen substrate 2 to the TEM-specimen holder 19'.

In addition, the specimen fabrication apparatus also includes:

a sample-stage position controller 3' for controlling the position of the sample stage 3;

a deposition-gas supplying source controller 8' for controlling the deposition-gas supplying source 8;

a specimen transferring unit controller 4' for controlling and driving the specimen transferring unit 4 independently of the sample stage 3;

an image display sub-unit 5 for displaying, among other things, images of the surface of the specimen substrate 2, the surface of the TEM-specimen holder 19' and the tip of a probe 11 held by the specimen transferring unit 4; and an FIB controller 7 for driving and controlling the FIB irradiating optical system 1.

It should be noted that the sample-stage position controller 3', the specimen transferring unit controller 4', the image display sub-unit 5, the FIB controller 7, the deposition-gas supplying source controller 8' and some other components are controlled by a central processing unit (CPU) 6.

As shown in FIG. 19, the FIB irradiating optical system 1 lets an ion beam emitted by a liquid metallic ion source 41 pass through a beam limiting aperture 42, a condenser lens 49 and an objective lens 50 to produce a focused ion beam (FIB) 13 with a diameter in the range several tens of nmφ to about 1 μmφ. The FIB 13 is driven by a deflector 51 in a scanning operation carried to sweep the surface of the specimen substrate 2, allowing fabrication to be carried out on the surface in accordance with the shape of a scanning pattern at a precision in the range 1 micron to a value at a sub-micron level. Here, what are meant by the technical term 'fabrication' include formation of a dent by sputtering, formation of a protrusion by ion-beam assist deposition (IBAD) and a fabricating operation such as modification of the shape of the specimen substrate surface through a combination of the formation of dents and the formation of protrusions. A deposition film (IBAD film) created by irradiation of the FIB 13 is used for firmly joining the tip of the probe 11 held by the specimen transferring unit 4 to the surface of the specimen substrate 2 and a micro-specimen 40 extracted from the specimen substrate 2 to the TEM-specimen holder 19'. The secondary-particle detector 12 is used for detecting secondary particles such as secondary electrons and secondary ions emitted by the surface of the specimen substrate 2 due to irradiation of the FIB 13 to the surface. A detection signal generated by the secondary-particle detector 12 creates an image of a portion to which the FIB 13 is irradiated and, by displaying the image, the portion such as a fabricated area can be observed. The sample stage 3 is placed in the sample chamber 77 and components such as the FIB irradiating optical system 1 are located in a vacuum container. A holder cassette 17' for holding the TEM-specimen holder 19' can be mounted on and removed from the sample stage 3. The sample stage 3 is designed so that the stage 3 can be moved in the three-dimensional directions, namely, the X, Y and Z axial directions, can be tilted and can be rotated. The sample-stage position controller 3' is used for controlling the position of the sample stage 3.

Configurations and functions of elements constituting the specimen fabrication apparatus as implemented by the fourth embodiment of the present invention are described in concrete terms and in more detail as follows.

4-1 [Specimen Transferring Unit and its Place of Installation]

Figure 20A:
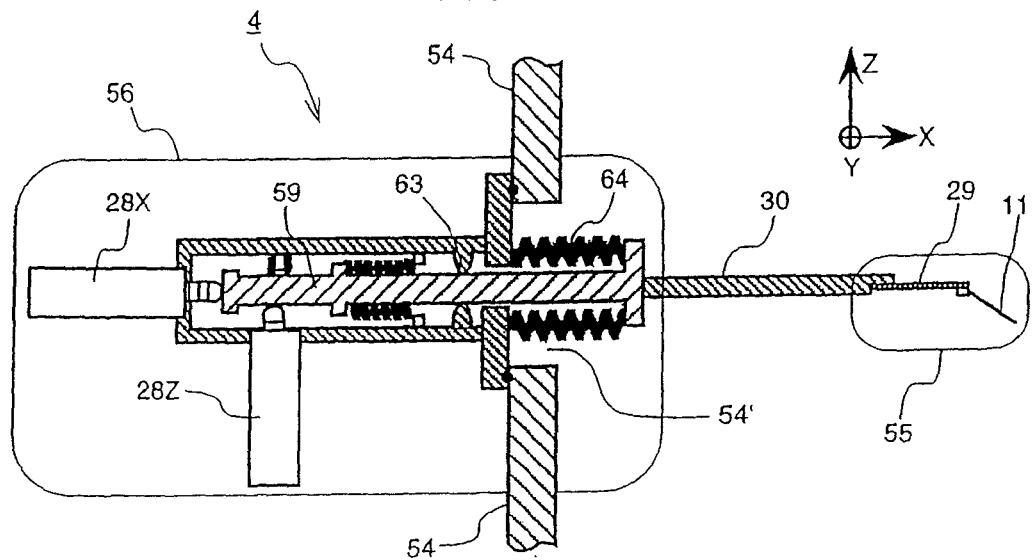
FIGS. 20A, 20B and 20C are diagrams each showing a typical configuration of a specimen transferring unit employed in the specimen fabrication apparatus provided by the present invention.

FIG. 20A is a diagram showing a typical configuration of the specimen transferring unit 4 for transferring a micro-specimen 40 extracted from the specimen substrate 2 to the TEM-specimen holder 19'. As shown in the figure, the specimen transferring unit 4 comprises 2 units, namely, a coarse-movement actuator 56 and a fine-movement actuator 55. Composed of electro-mechanical components such a motor, a gear and a piezoelectric device, an XYZ-direction driving mechanism of the coarse-movement actuator 56 has a movement range (stroke) of at least 3 mm with a movement resolution of the order of several microns. Required of as compact a design as possible, the fine-movement actuator 56 employs a piezoelectric device. Particularly, in the case of this embodiment, a bimorph-type piezoelectric device is selected. The bimorph-type piezoelectric device offers a merit of a relatively long stroke of at least several hundreds of microns in comparison with piezoelectric devices of other types. On the other hand, since the coarse-movement actuator 56 is not required of a high positional precision, the coarse-movement actuator 56 can be manufactured with ease. The coarse-movement actuator 56 employed in this embodiment vibrates at an amplitude in a range of ten plus several microns during a movement, but the vibration is all but negligible in a stationary state. Thus, it is possible to adopt a method whereby the tip of the probe 11 is first taken to a position in close proximity to the surface of the specimen substrate 2 and put at a standstill by using the coarse-movement actuator 56 before the tip of the probe 11 is brought into contact with the surface of the specimen substrate 2 by means of the fine-movement actuator 55. With this method, since a resolution of the order of microns will prove sufficient for positional control of the tip of the probe 11, even the bimorph-type piezoelectric device having a relatively poor resolution in comparison with piezoelectric devices of other types is capable of satisfactorily satisfying the requirement of the positional control. As a result, the fine-movement actuator 55 can be manufactured at a low cost.

As described previously, with the conventional technology disclosed in Japanese Patent Laid-open No. Hei 5-52721 used as prior-art reference 3, a manipulator serving as a unit for conveying a micro-specimen 20 extracted from the specimen substrate 2 has a configuration including 3 bimorph-type piezoelectric devices for movements in the X, Y and Z axial directions respectively. Since this conveying unit is installed on the sample stage 3 on which the specimen substrate 2 is mounted, however, there is raised a fatal problem that, in the case of an area to be observed existing at the center of the specimen substrate (wafer) having a large diameter of 300 mm, the movement stroke of the conveying unit is not sufficient for the tip of the probe 11 to reach the area. In addition, as described above, the conveying means employs 3 bimorph-type piezoelectric devices for movements in the X, Y and Z axial directions respectively wherein each of the bimorph-type piezoelectric devices has one end thereof serving as a fixed supporting point and the other end moving to bend the device. That is, the other end moves along an arc-shaped locus in accordance with an applied voltage. Strictly speaking, in a movement on the XY plane, driven only by a specific bimorph-type piezoelectric device, the tip of the probe does not move in an axial direction corresponding to the specific bimorph-type piezoelectric device along a truly straight line. Thus, with the fine-movement actuator 55 comprising the 3 bimorph-type piezoelectric devices, in order to move the tip of the probe 11 to a desired location with a high degree accuracy, it is necessary to move each of the 3 bimorph-type piezoelectric devices by taking the movements of the others into consideration. As a result, there is raised a problem of complex operations to drive the 3 bimorph-type piezoelectric devices in such a manner that their movements are related to each other. In order to solve this problem, it is necessary to employ 3 axial-direction driving means that are each capable of moving the probe 11 along a straight line with a high degree of accuracy. If the conveying unit is required to be capable of moving the probe 11 by a long stroke of at least 100 mm as well as a resolution of the micron order by utilizing only a fine-movement mechanism, the structure of the mechanism will become complicated and will become big in size. As a result, a problem of contention for installation space with other components surrounding the sample stage 3 such as the secondary-electron detector 12 and the deposition-gas supplying source 8 will remain to be solved.

In order to solve the problems described above, the present invention provides a specimen transferring unit 4 that is capable of carrying out sampling quickly from any arbitrary location even if the specimen substrate 2 is a wafer with a large diameter. In order to realize such a capability, the specimen transferring unit 4 is designed to comprise a coarse-movement actuator 56 having a high movement speed and a large stroke and a fine-movement actuator 55 having a stroke about equal to the movement resolution of the coarse-movement actuator 56 and a high movement resolution. In addition, the whole specimen transferring unit 4 is installed independently of the sample stage 3 and a movement over a long distance to a sampling position is made by partly resorting to a movement by the sample stage 3. Furthermore, the coarse-movement actuator 56 which has a tendency to increase in size is provided at a location very far away from the specimen substrate 2 and the fine-movement actuator 55 is implemented by a fine-movement mechanism for movements in the Z-axial direction only. As a result, interference in space of installation with other components surrounding the sample stage 3 can be avoided. As described above, the specimen transferring unit 4 provided by the present invention is designed by sufficiently taking the size and the place to install into consideration. As a result, the specimen transferring unit 4 solves all the problems effectively.

As shown in the FIG. 20A, in the configuration of the coarse-movement actuator 56, a coarse-movement shaft 59 is moved in the X, Y and Z axial directions by encoders 28X, 28Y and 28Z respectively with an isthmus 63 used as a supporting point. It should be noted that the encoder 28Y is not shown in the figure. While the coarse-movement stroke and the movement resolution are dependent on the performance of each of the encoders 28X, 28Y and 28Z, a stroke of 10 mm and a resolution of 2 microns can be achieved with ease. A force for resisting a pressing force generated by each of the encoders 28X, 28Y and 28Z is provided by a means such as a spring. The generation of such a resisting force is not explained in this description. A driving system of the coarse-movement actuator 56 is provided on the atmosphere side through a side port 54' of a specimen chamber 54. A vacuum state of the specimen chamber 54 is shielded against the atmosphere by a bellows 64. A portion of the coarse-movement shaft 59 on the vacuum-chamber side is linked to the fine-movement actuator 55 through an extension rod 30. The fine-movement actuator 55 is designed to drive the probe 11 only in the Z-axial direction. In a driving system of the fine-coarse actuator 56, a bimorph-type piezoelectric device 29 is employed to provide a movement resolution of the sub-micron order. The end of the bimorph-type piezoelectric device 29 is joined to a probe 11 made of a tungsten wire with a pointed tip having a diameter of 50 $\mu m\phi$. When a driving voltage is applied to the bimorph-type piezoelectric device 29, the tip of the probe 11 makes a fine movement.

Figure 20B:
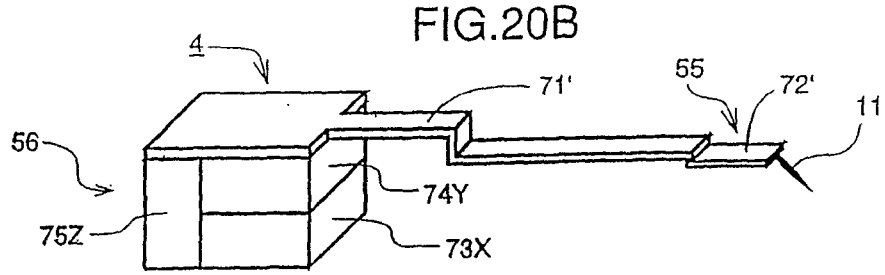

FIG. 20B is a diagram showing another example of the configuration of the specimen transferring unit 4. In this example, the configuration of the coarse-movement actuator 56 comprises a combination of 3 block-shaped piezoelectric devices 73, 74 and 75 for movements in the X, Y and Z axial directions respectively. A block-shaped piezoelectric device has a slightly inferior movement resolution but offers merits such as a long movement stroke and endurance against a heavy load. The coarse-movement actuator 56 is connected to a fine-movement actuator 55 implemented by a bimorph-type piezoelectric device 72' through an extension rod 71'. The fine-movement actuator 55 is used for holding the probe 11.

Figure 20C:
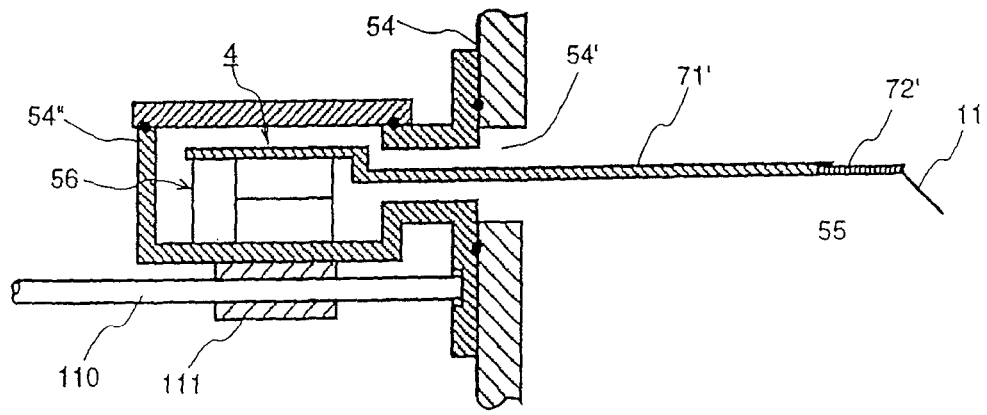

A typical case in which the specimen transferring unit 4 shown in FIG. 20B is installed in the specimen chamber 54 is shown in FIG. 20C. In this example, a small vacuum chamber 54" is provided through the side port 54' of the specimen chamber 54. In the small vacuum chamber 54, the coarse-movement actuator 56 is installed. When the specimen transferring unit 4 is not in use, it can be taken out with ease from the specimen chamber 54 by using a slider 111 which can be sled along a rail 110. In this configuration, the only components placed inside the specimen chamber 54 are the extension rod 71', the bimorph-type piezoelectric 72' attached to the end of the extension rod 71' and the probe 11. Thus, interference with a variety of other components in the specimen chamber 54 can be avoided, allowing the probe 11 to make an access to the surface of the specimen substrate 2.

Figure 21:
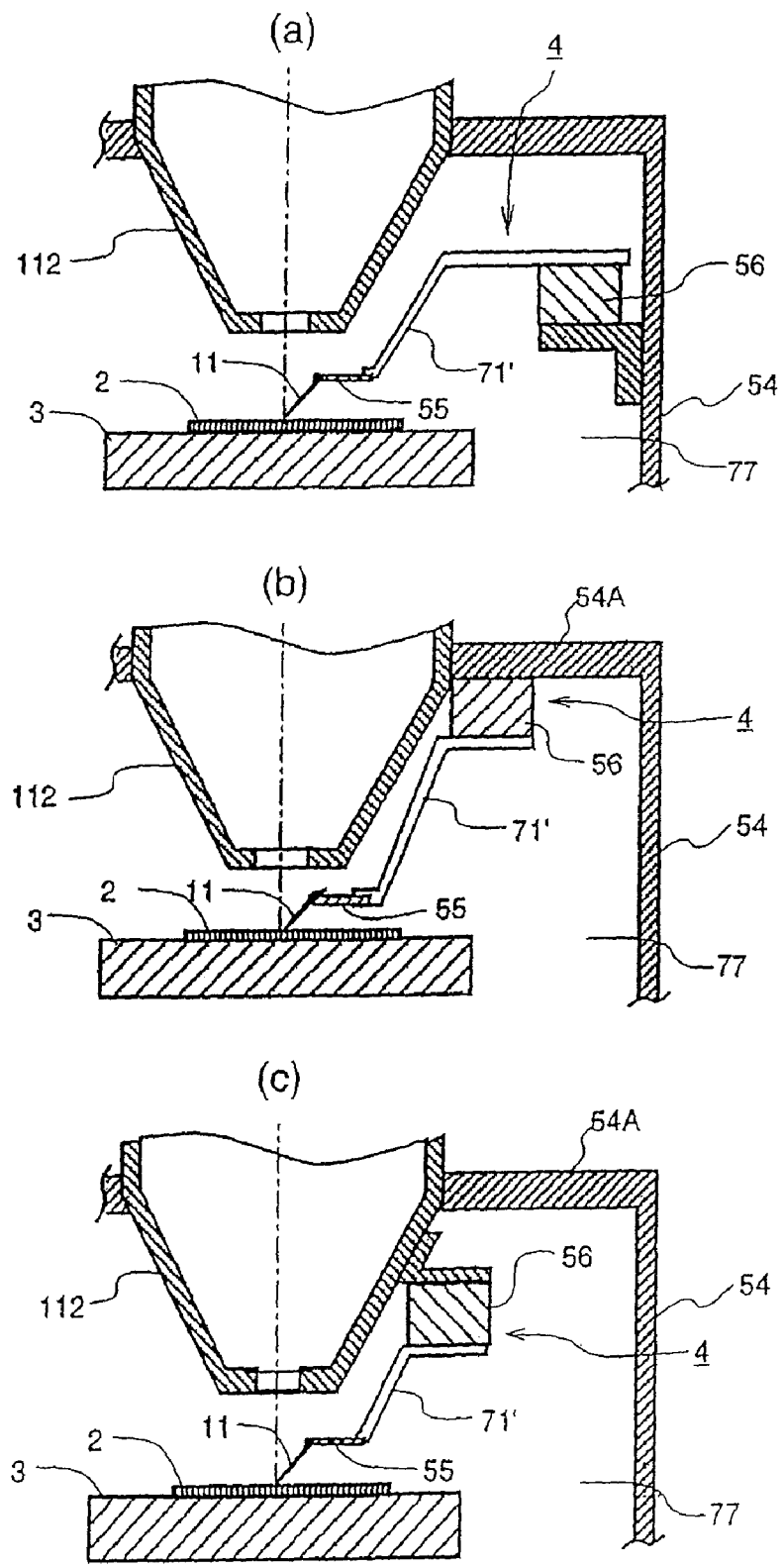
FIG. 21 is explanatory diagrams each showing a location at which the specimen transferring unit employed in the specimen fabrication apparatus provided by the present invention is installed.

FIG. 21 is explanatory diagrams each showing a location at which the specimen transferring unit 4 is installed. To be more specific, FIG. 21/(a) is a diagram showing an example wherein the specimen transferring unit 4 comprising the coarse-movement actuator 56 and the fine-movement actuator 55 is attached to a side wall 54 of the specimen chamber 77 in such a way that the probe 11 is capable of making an access to a position between the surface of the specimen substrate 2 mounted on the sample stage 3 and a final electrode 112 of the FIB irradiating optical system 1 which is installed to face the surface of the specimen substrate 2. On the other hand, FIG. 21/(b) is a diagram showing an example wherein the specimen transferring unit 4 is installed on the ceiling 54A of the specimen chamber 77. Finally, FIG. 21/(c) is a diagram showing an example wherein the specimen transferring unit 4 is installed on a side surface of a final electrode 112 of the FIB irradiating optical system 1. A point common to these examples is the fact that, in the configurations, the specimen transferring unit 4 is not placed on the sample stage 3 and driven as well controlled independently of the sample stage 3. As such, the configurations are designed in such a way that, during a movement of the specimen substrate 2, the specimen transferring unit 4 never comes in contact with the surface of the specimen substrate 2.

In the configuration shown in FIG. 21/(a), the specimen transferring unit 4 is attached to the side wall 54 of the specimen chamber 77 so that the specimen transferring unit 4 is capable of keeping up with an apparatus without a side port provided on the side wall 54 of the specimen chamber 77. In the example shown in FIG. 21/(b), on the other hand, the specimen transferring unit 4 is installed on the ceiling 54A of the specimen chamber 77, offering merits that the space in the specimen chamber 77 can be utilized effectively and the specimen transferring unit 4 is capable of keeping up with apparatuses each having a different configuration. Finally, in the configuration shown in FIG. 21/(c), the specimen transferring unit 4 is installed on a side surface of the final electrode 112 of the FIB irradiating optical system 1, also offering merits that the space in the specimen chamber 77 can be utilized effectively and no excessive components protrude out to the outside of the specimen chamber 77. As a result, the outside of the specimen chamber 77 can be occupied by other components with complicated configurations and the external view of the apparatus can be made look clean.

A variety of other configurations for installing the specimen transferring unit 4 are possible. At any rate, the basic concept embraced in the examples of the configurations shown in FIG. 21 is to install the specimen transferring unit 4 in such a way that the specimen transferring unit 4 can be driven as well controlled independently of the sample stage 3 and, during a movement of sample stage 3, the specimen transferring unit 4 never comes in contact with the surface of the specimen substrate 2. As a result, an access can be made to any micro-specimen 40 to be extracted with ease even if the micro-specimen 40 is located at the center of a wafer having a large diameter.

4-2 [Locations for Installing the TEM-Specimen Holder]

A micro-specimen 40 extracted from the specimen substrate 2 is transferred to the TEM-specimen holder 19' serving as a member to which the micro-specimen 40 is to be fixed. In order to transfer a micro-specimen 40 to the TEM-specimen holder 19', it is necessary to mount the TEM-specimen holder 19' on the sample stage 3 by using the holder cassette 17' for holding the TEM-specimen holder 19' or to mount the TEM-specimen holder 19' on a side-entry-type stage such as a TEM stage which is independent of the sample stage 3. The sample stage 3 can be a general-purpose large-size sample stage allowing a wafer itself to be mounted thereon or a sample stage with a small size enough for mounting a device chip. A place at which the specimen holder 19' is installed greatly affects the workability following an operation to transfer a micro-specimen 40 extracted from the specimen substrate 2 to the TEM-specimen holder 19'. For this reason, a place at which the specimen holder 19' is installed is explained specially as follows.

The following description explains 3 systems to install the TEM-specimen holder 19', namely, a sample-stage system, a wafer-cassette system and a TEM-stage system. In the sample-stage system, the TEM-specimen holder 19' is mounted on the sample stage 3. In the wafer-cassette system, on the other hand, the TEM-specimen holder 19' is mounted on a wafer cassette which accommodates the specimen substrate 2 (that is, the wafer) and can be put in and taken out from the specimen chamber 77. Finally, in the TEM-stage system, the TEM-specimen holder 19' is mounted on a TEM stage (or a stage for both the TEM and the FIB).

4-2-1 [Sample-Stage System]

Figure 22:
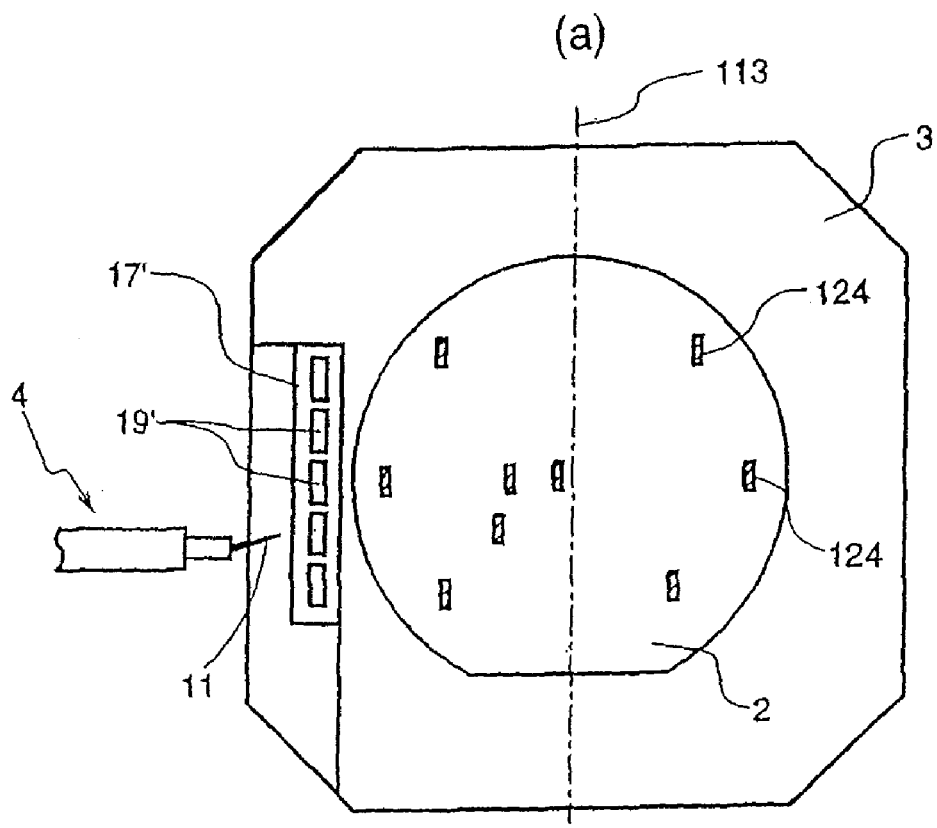
FIG. 22 is diagrams showing an example of a method to install a TEM-specimen holder in the specimen fabrication apparatus provided by the present invention.
Figure 22:
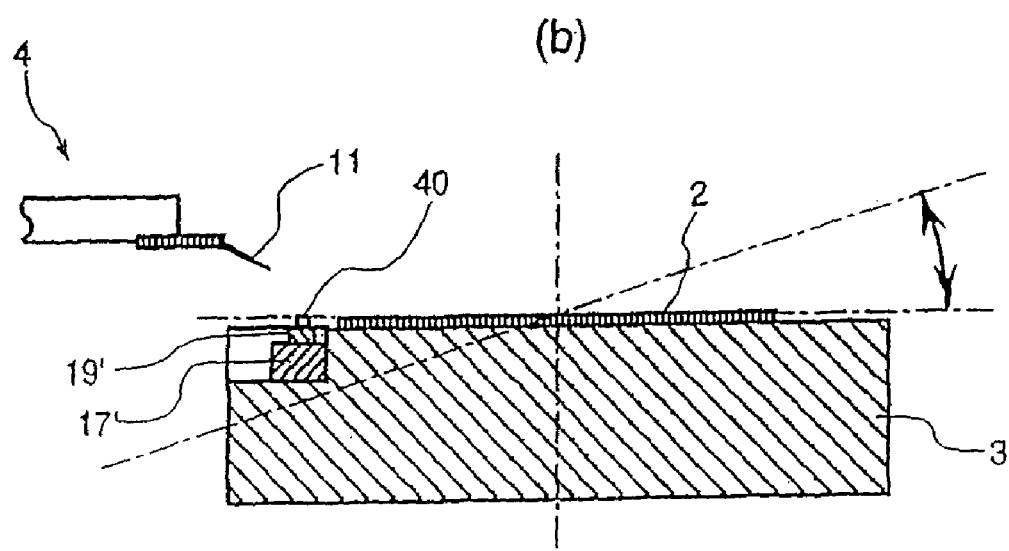

FIG. 22 is explanatory diagrams showing an example of a method to install the TEM-specimen holder 19' in the sample-stage system. To be more specific, FIG. 22/(a) is a diagram showing a top view of the sample stage 3 and FIG. 22/(b) shows a cross section of the center of the sample stage 3. In this system, the TEM-specimen holder 19' is set on the holder cassette 17' which can be mounted on and removed from the sample stage 3 with ease. The number of TEM-specimen holders 19' that can be set on the holder cassette 17' is arbitrary and the number of holder cassettes 17' that can be mounted on the sample stage 3 is also arbitrary. FIG. 22/(a) shows an example in which 1 holder cassette 17' is mounted on the sample stage 3 and 5 TEM-specimen holders 19' are set in the holder cassette 17'. If 3 micro-specimens 40 extracted from the specimen substrate 2 are mounted on each of the TEM-specimen holders 19', 15 TEM specimens can be mounted on the holder cassette 17'.

The holder cassette 17' is mounted on the sample stage 3 in such a way that the upper surface of the TEM-specimen holder 19' is set at about the same level as the surface of the specimen substrate 2. In this way, when a micro-specimen 40 extracted from the specimen substrate 2 is transferred to the TEM-specimen holder 19', the micro-specimen 40 does not come in contact with the TEM-specimen holder 19' and other components. Furthermore, the desired surface on the micro-specimen 40 to be observed is oriented in a direction parallel to the longitudinal direction of the TEM-specimen holder 19' which is set in such a way that the longitudinal direction thereof is parallel to an inclination axis 113 of the sample stage 3. It should be noted that the shape of the TEM-specimen holder 19' will be described later in concrete terms. Such a positional arrangement allows the micro-specimen 40 extracted from the specimen substrate 2 to be mounted on the TEM-specimen holder 19' in a movement in the Z-axial direction only without the need to carry out an operation on the micro-specimen 40 such as a rotation. Then, by mounting the TEM-specimen holder 19' with the extracted micro-specimen 40 mounted thereon on a TEM or SEM stage, the desired observation area can be observed with ease.

The holder cassette 17' can be mounted on or removed from the sample stage 3 by a sliding movement and, by using an operation rod, a load lock chamber and other tools, the holder cassette 17' can be taken out from the specimen chamber 77 without destroying the vacuum state of the specimen chamber 77 in a manner independent of the sample stage 3. By virtue of this system, a large number of TEM micro-specimens 40 can be fabricated continually from a specimen substrate 2 and, when the holder cassette 17' is taken out from the specimen chamber 77, the same number of TEM micro-specimens 40 can be obtained at once. In addition, the TEM micro-specimens 40 mounted on TEM-specimen holders 19' can be temporarily kept in a box for storage for each holder cassette 17' in which the TEM-specimen holders 19' are set. Thus, the work to handle these infinitesimal TEM micro-specimens 40 is not a great strain on the nerves. In addition, the holder cassette 17', on which a large number of micro-specimens 40 just extracted from the specimen substrate 2 as they are and supposed to undergo a thinning fabrication or a wall fabrication are mounted, can be conveyed into a separately provided FIB apparatus serving as an apparatus used specially for carrying out the finishing fabrication (or the thinning fabrication) only A position on the sample stage 3 at which the TEM-specimen holder 19' is mounted is explained by referring to FIG. 22/(b). Supposed to undergo a fabrication such as the thinning fabrication described above, an extracted micro-specimen 40 has to be inclined. Thus, if the sample stage 3 is installed at an inappropriate location, there will be raised a problem of a damage inflicted on the specimen transferring unit 4, making it impossible to fabricate the required micro-specimen 40. Components such as the holder cassette 17' with TEM-specimen holder 19' set therein, the secondary-electron detector 12 and the deposition-gas supplying source 8 are always installed on a side on which the specimen transferring unit 4 is provided. In the example shown in FIG. 22/(b), the components are installed on the left-hand side of the sample stage 3 with respect to the inclination axis 113. The inclination of the sample stage 3 causes the side on which the TEM-specimen holder 19' is set, that is, the left side, to always move from a horizontal posture in a downward direction. As a result, interference with other structures in the specimen chamber 77 described above can be avoided.

Figure 23:
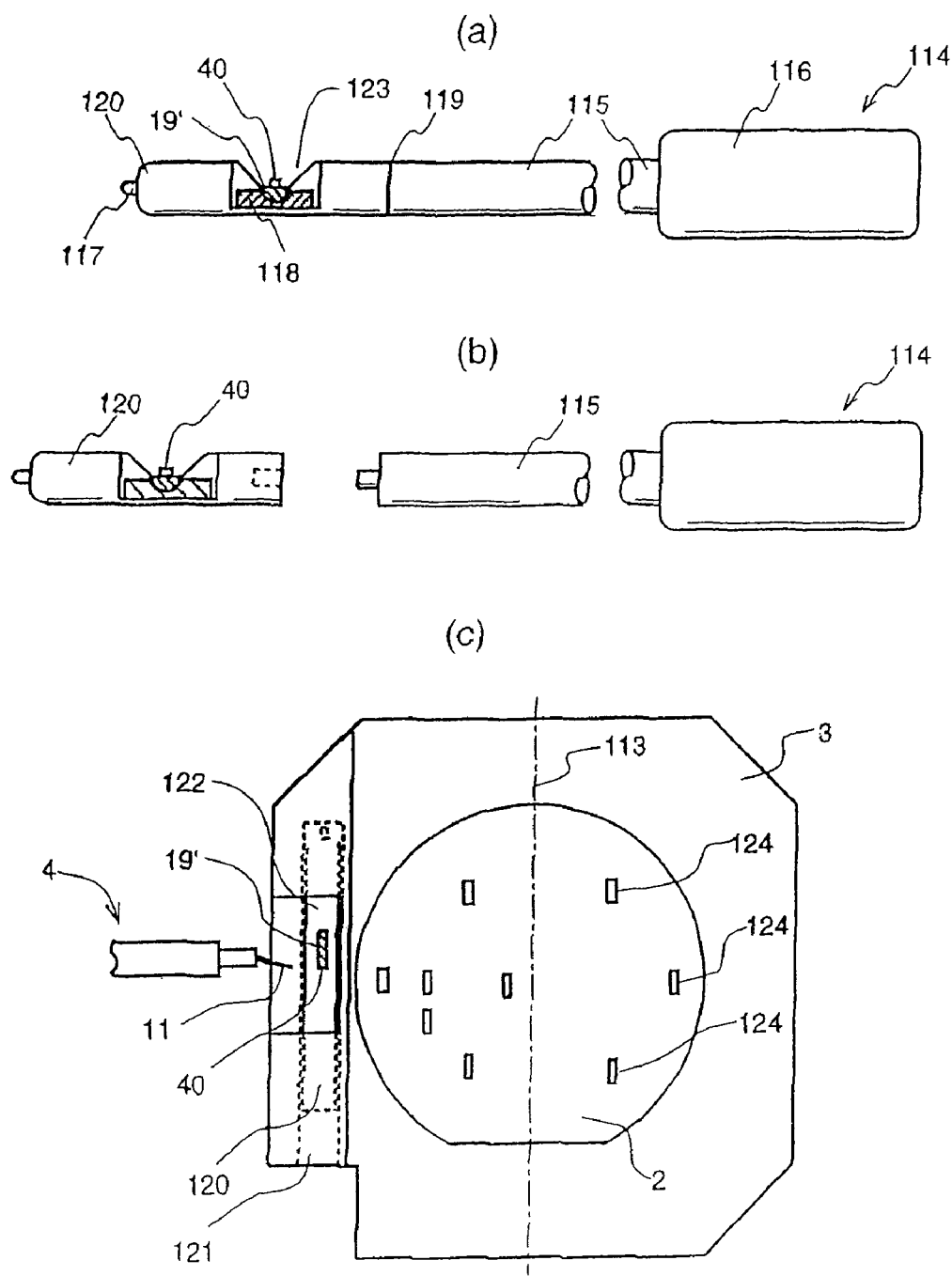
FIG. 23 is diagrams showing another example of a method to install the TEM-specimen holder in the specimen fabrication apparatus provided by the present invention.

As another method regarding a place to install the TEM-specimen holder 19', it is possible to adopt a method whereby the structure of an end 120 of a TEM stage 114 including a fixed portion of the TEM-specimen holder 19' is improved and the TEM stage 114 is mounted on the sample stage 3. The following description begins with an explanation of the TEM stage 114 with a configuration allowing the end 120 thereof to be attached and detached. FIG. 23/(a) is a diagram showing the TEM stage 114 used in this embodiment. As shown in the figure, the TEM stage 114 comprises components such as a shaft 115, a handle 116, a position setting part 117 and a specimen fixing part 118. The TEM-specimen holder 19' is seated on a cut 123 of the shaft 115. The TEM stage 114 is most characterized in that the stage 114 has a configuration that allows an end 120 thereof to be stuck to or detached from the main body of the TEM stage 114 at a separation position 119 as shown in FIG. 23/(b). That is, the end 120 can be detached from the main body and inserted into the sample stage 3. FIG. 23/(c) is a diagram showing a state in which the end 120 of the TEM stage 114 has been inserted into the sample stage 3. To put it in detail, the end 120 of the TEM stage 114 is inserted into an insertion area 121 provided on the sample stage 3 to be held therein. The insertion area 121 has an opening 122 above the TEM-specimen holder 19'. A micro-specimen 40 extracted from an area 124 to be observed on the specimen substrate 2 is held on the tip of the probe 11 of the specimen transferring unit 4 and transferred to the insertion area 121 to be firmly held on the TEM-sample holder 19' through the opening 122.

After the extracted micro-specimen 40 has been firmly held by the TEM-specimen holder 19' the micro-specimen 40 is subjected to a thinning fabrication (or a wall fabrication) by using an FIB with the micro-specimen 40 firmly held by the TEM-specimen holder 19' as it is to be converted into a TEM specimen. During the thinning fabrication, the FIB used for the fabrication is irradiated to the micro-specimen 40 in a direction perpendicular to the sheet of paper showing FIG. 23/(c).

Later on, when the micro-specimen 40 firmly held by the TEM-specimen holder 19' is taken out from the specimen chamber 77, the main body of the TEM stage 114 is inserted into the insertion area 121 to join the main body to the end 120 of the TEM stage 114 in the insertion area 121. Then, the micro-specimen 40 is taken out from the specimen chamber 77 along with the whole TEM stage 114. Held by the TEM stage 114, the micro-specimen 40 is brought into a TEM-specimen chamber to undergo an observation using a TEM. During the observation using a TEM, an electron beam used for the observation is irradiated to the micro-specimen 40 in a direction perpendicular to the sheet of paper showing FIG. 23/(a).

In the method described above by referring to FIG. 23, the end 120 of the TEM stage 114 which can be attached to and detached from the main body of the TEM stage 114 has a size of the cm order. Thus, the work to attach and detach the end 120 from the main body is not a great strain on the nerves. As a result, this method offers a merit that any person can do the work to fabricate a TEM specimen with ease.

Figure 24:
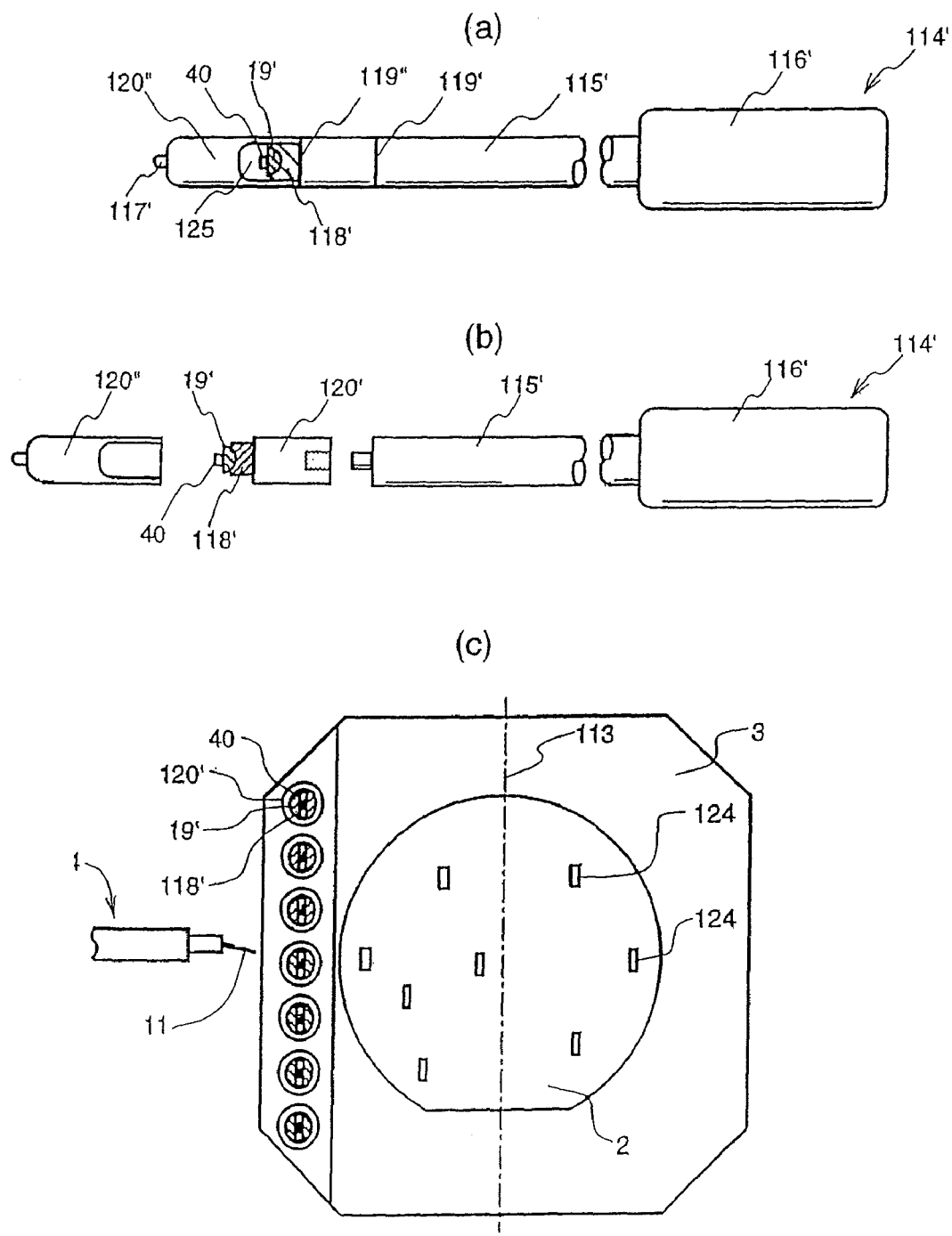
FIG. 24 is diagrams showing a further other example of a method to install the TEM-specimen holder in the specimen fabrication apparatus provided by the present invention.

FIG. 24 is diagrams showing a further other example of a method to install the TEM-specimen holder 19' on a TEM stage 114' having a structure different from the TEM stage 114 described above. As shown FIG. 24/(a), the TEM stage 114' comprises components such as a shaft 115', a handle 116', a position setting part 117' and a specimen fixing part 118'. Unlike the method of installation shown in FIG. 23/(a), however, since no cut 123 is provided on the shaft 115', the observation by using a TEM can not be carried out by using the same TEM stage 114' as the fabrication using an FIB. In order to solve this problem, the TEM stage 114' is designed into a configuration that allows ends 120' and 120" thereof to be stuck to or detached from the main body of the TEM stage 114' at separation positions 119' and 119" respectively as shown in FIG. 24/(b). In FIG. 24, (a) and (b) are diagrams each showing a state in which no TEM micro-specimen 40 is fixed on the specimen fixing part 118'. A plurality of ends 120' each having no micro-specimen 40 attached thereto are fixed to the sample stage 3 perpendicularly to the surface of the sample stage 3, that is, the surface of the wafer for mounting such ends 120', in such a way that, after a TEM micro-specimen 40 is seated on the TEM-specimen holder 19', the TEM-observation surface is set in parallel to the inclination axis 113 of the sample stage 3 as shown in FIG. 24/(c). A micro-specimen 40 extracted from an area 124 on the sample substrate 2 to be observed is held on the tip of the probe 11 employed in the specimen transferring unit 4 and transferred to the TEM-specimen holder 19' on the end 120' of the TEM stage 114 which has been firmly held on the sample stage 3 to be fixed to the TEM-specimen holder 19'. In the example shown in FIG. 24/(c), 7 TEM-specimen holders 19' are mounted on the sample stage 3. If 3 extracted, micro-specimens 40 are fixed on each of the TEM-specimen holders 19', a total of 21 TEM specimens 40 can be fabricated continually in the same specimen chamber.

4-2-2 [Wafer-Cassette System]

Figure 25:
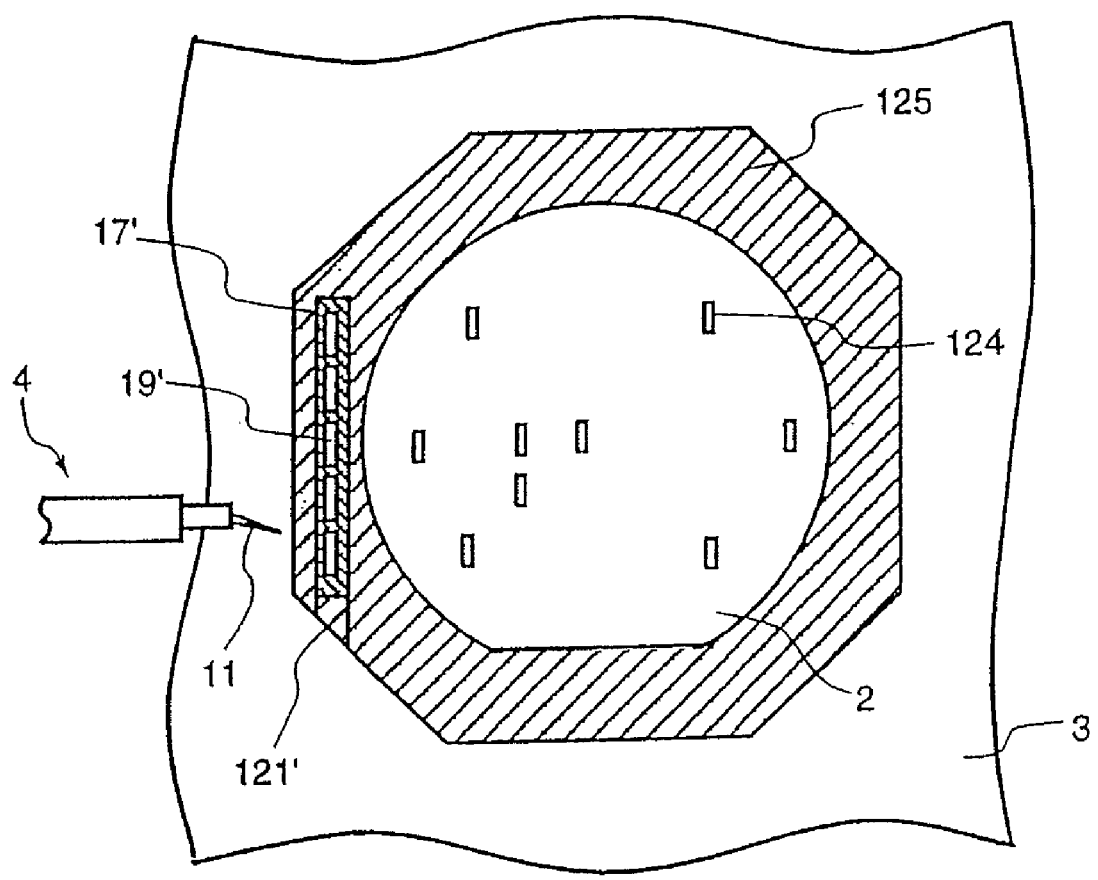
FIG. 25 is a diagram showing a still further other example of a method to install the TEM-specimen holder in the specimen fabrication apparatus provided by the present invention.

FIG. 25 is a diagram showing a typical configuration of an apparatus used in the wafer-cassette system. As shown in the figure, in this system, the holder cassette 17' for holding the TEM-specimen holder 19' is mounted on a wafer cassette 125. Since the wafer cassette 125 is a tray used exclusively for accommodating 1 wafer 2, that is, 1 specimen substrate 2, components of the apparatus and the hands of the operator never come in contact with the wafer 2 accommodated therein. In addition, since the wafer cassette 125 can be put in or taken out from various kinds of process equipment as it is, the cassette 125 can also be used for transferring the wafer 2 from equipment to equipment. As shown in FIG. 25, the holder cassette 17' is designed into such a configuration that the holder cassette 17' can be mounted on and removed from the holder-cassette mounting unit 121' of the wafer cassette 125. Thus, a plurality of TEM-specimen holders 19' each for mounting a plurality of TEM micro-specimens 40 can be obtained at the time the wafer 2 is replaced. A relation between the wafer cassette 125 and the holder cassette 17', relations between the holder cassette 17' and TEM-specimen holders 19' set therein and relations between each of the TEM-specimen holders 19' and extracted micro-specimens 40 fixed thereto are always controlled. As a result, it is easy to obtain information such as a relation between a position on the wafer 2 from which a TEM micro-specimen 40 has been extracted and information obtained as a result of an analysis, a measurement or an observation using a TEM.

4-2-3 [TEM-Stage System]

In this system, a TEM-specimen holder 19' is mounted on a stage which operates independently of the sample stage 3. By independently operating stage, a TEM stage of the side-entry side type is typically implied. In this example, the side-entry-type TEM stage is designed into a configuration that can be put in or taken out from the specimen chamber 77. In this case, the side-entry-type TEM stage is set so that an axis of rotation thereof is parallel to the inclination axis 113 of the sample stage 3. Note that it is desirable to place a desired area to be observed as an extracted micro-specimen 40 on the rotation axis of the side-entry-type TEM stage. Since the extracted micro-specimen 40 to be mounted on the TEM-specimen holder 19' has an infinitesimal size in the range several microns to 30 microns, however, in actuality, it is sufficient to place the desired area at such a location that the specimen fixing surface of the TEM-specimen holder 19' comes to a position close to the rotation axis of the side-entry-type TEM stage. In this configuration, a micro-specimen 40 extracted from the specimen substrate 2 can be mounted on a TEM-specimen holder 19' by only a movement in the Z-axial direction without the need to carry out an operation such as a rotation. Thus, it is no longer necessary to add a complex mechanism such as a tilting mechanism or a rotating mechanism to the specimen transferring unit 4, giving rise to a merit of a simple configuration of the specimen transferring unit 4. In addition, in the case of this system, once an extracted micro-specimen 40 has been fixed to a TEM-specimen holder 19', the TEM stage 114 can be taken out from the specimen chamber 77 and mounted on a TEM apparatus as it is. Thus, a lengthy manual work requiring a skill of a well trained person is not needed till an observation using a TEM. As a result, the length of time it takes to fabricate a micro-specimen 40 can be reduced considerably, resulting in an effect of substantial reduction of a strain on the nerves caused by the work to fabricate the micro-specimen 40. In addition, in case an observation using a TEM is difficult to carry out due to, among other reasons, the fact that a portion of the wafer 2 to be observed, that is, the wall portion, is excessively thick, the method offers a convenience that the TEM stage 114 is simply brought again as it is into the specimen chamber 77 of the apparatus for fabricating the micro-specimen 40, allowing a re-fabrication by irradiation of an FIB to be performed right away.

4-3 [Embodiment of the TEM-Specimen Holder]

Figure 7:
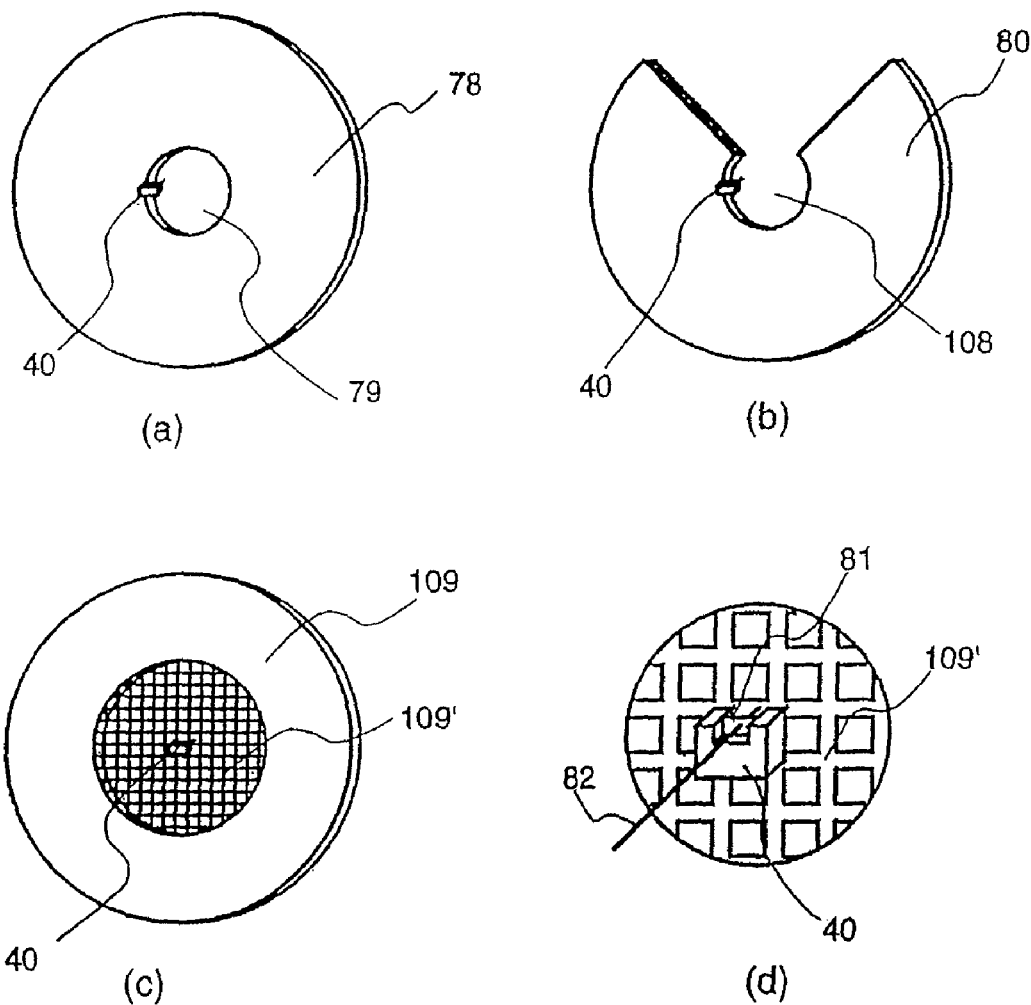
FIG. 7 is diagrams each showing a typical configuration of the conventional TEM-specimen holder.

As a conventional TEM-specimen holder, among other types, a single-hole type shown in FIG. 7/(a) and a mesh-type shown in FIG. 7/(b) are known. A single-hole-type holder 78 has a hole 79 with a diameter of 1 mm$\phi$ provided at the center of a thin metallic circular disc. When a single-hole-type holder 78 is used, it is necessary to position a micro-specimen 79 on the inner surface wall of the hole 79 with a high degree of accuracy and install the specimen 79 thereon. Since a micro-specimen 40 obtained by adopting the method for fabrication of a specimen provided by the present invention has a small size in the range 10 to 20 microns, the work to position the micro-specimen 40 is very difficult to do. On the other hand, a mesh-type holder 109 has a metallic mesh 109' stretched over an opening at the center of a thin metallic circular disc. Thus, by using a metallic mesh 109' with a gap between mesh nodes adjusted to the size of the micro-specimen 40, the position at which the micro-specimen 40 is to be installed can be selected arbitrarily to a certain degree. With the mesh-type holder 109, however, the path of an electron beam passing through the micro-electron 40 is shielded by a mesh structure member, making an observation using a TEM impossible in some cases.

Figure 26:
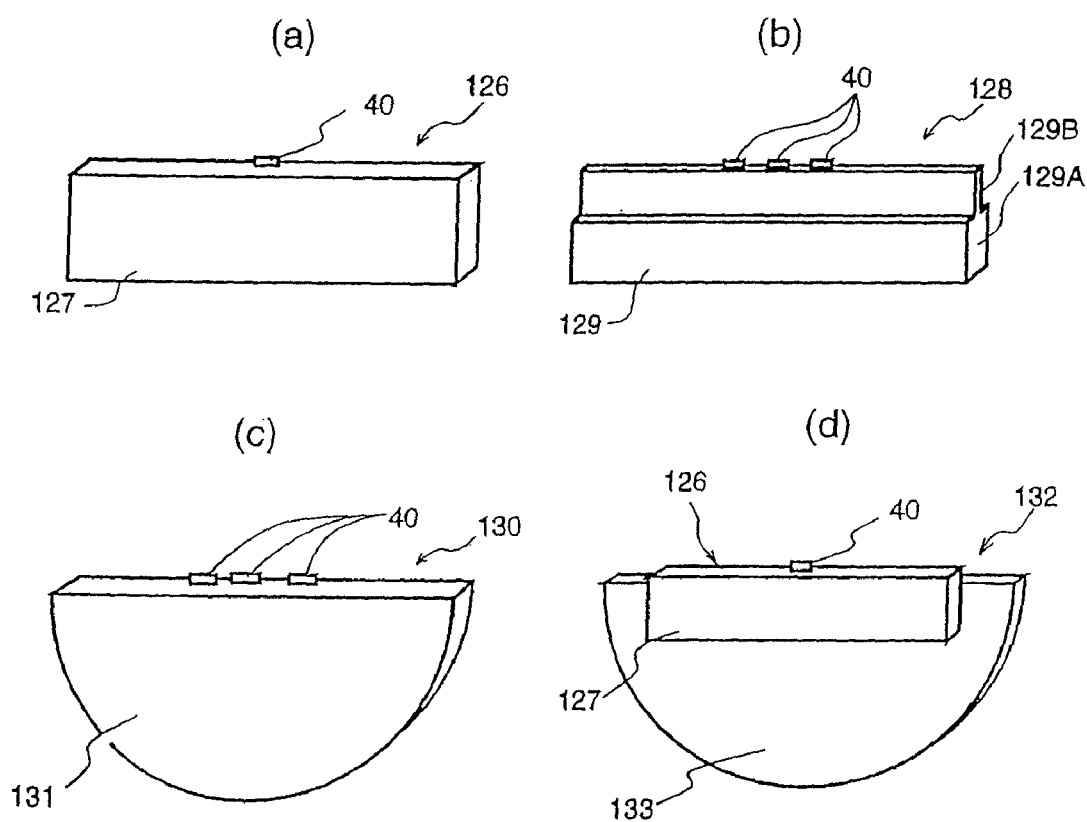
FIG. 26 is explanatory diagrams each showing an embodiment implementing the TEM-specimen holder in the specimen fabrication apparatus provided by the present invention.

As described above, an extracted micro-specimen 40 obtained by adopting the method for fabrication of a specimen provided by the present invention has a small size, strictly speaking, a height, in the range 10 to 20 microns. Thus, if a dent with depth of at least 20 microns is provided on the specimen fixing area of the holder, the extracted micro-specimen 40 will be embedded in the dent, causing an electron beam for observation to be shielded during an observation using a TEM. As a result, it is impossible to perform an observation using a TEM on the micro-specimen 40 which was extracted from the specimen substrate 2 with much trouble. In order to solve this problem, in this embodiment, a specimen holder shown in FIG. 26 is employed. The specimen holder is designed into such a structure that the direction of irradiation of an FIB during a fabrication using the FIB is perpendicular to the incidence direction of an observation electron beam used during an observation utilizing a TEM so that both the FIB and the electron beam are not shielded. In addition, the flatness of a specimen fixing surface is improved in particular in order to make the electron beam for observation easy to irradiate.

In a holder 126 shown in FIG. 26/(a), an extracted micro-specimen 40 is held on a sliver of silicon 127 cut out from a silicon wafer by using a cleaving tool or a dicing saw. In this example, the holder 126 is cut out from a silicon wafer to have a size with a length of 2.5 mm, a width of 50 microns and a height of 0.5 mm, that is, the thickness of the silicon wafer. By using the ground surface of the silicon wafer as a surface for fixing the extracted micro-specimen 40, the amount of unevenness of the fixing surface can be reduced. Thus, irradiation of the electron beam for observation is not obstructed during an observation using a TEM. It should be noted that the dimensions and shape of the holder 126 are not limited to those shown in the embodiment. In a word, it is necessary to use the ground surface of the silicon wafer as a surface for fixing an extracted micro-specimen 40 and to make the width of the holder 126 as small as possible.

A holder 128 shown in FIG. 26/(b) is an example of a modified version of the holder 126 shown in FIG. 26/(a). In the case of the holder 126, it is desirable to make the width of the holder 126 as small as possible so as to prevent irradiation of an electron beam for observation from being obstructed due to a slight inclination of the holder 126 during an observation using a TEM. If the width of the holder 126 is made extremely small, however, the mechanical strength of the holder 126 deteriorates, raising a problem such as a handling damage inflicted on the holder 126. In order to solve this problem, in the case of the holder 128 shown in FIG. 26/(b), the holder 128 is designed into a structure that provides a sufficient mechanical strength and no hindrance to irradiation of an electron beam. To put it in detail, a sliver of silicon 129 is cut out from a silicon wafer with a wide bottom 129A and a narrow top 1298. That is, the cross section of the piece of silicon 129 has a convex shape which consists of two rectangles that are contacted at the sides. An extracted micro-specimen 40 is mounted on the surface of the narrow top 128B, that is, the ground surface of the original silicon wafer. In the example shown in FIG. 26/(b), a plurality of micro-specimens 40, to be more specific, 3 micro-specimens 40, are mounted on the holder 128.

A holder 130 shown in FIG. 26/(c) is created as a silicon plate 131 having a semi-circular shape by applying a cleaving or wet-etching technology to a silicon wafer. The holder 130 has a diameter of about 3 mm and a thickness of about 50 microns. The surface for fixing an extracted micro-specimen 40 is the cleaved surface of the original silicon wafer which has enough smoothness. Since this holder 130 has a semi-circular shape, by using a ring-shape washer, the holder 130 can be mounted on a TEM stage 114 with ease.

A holder 132 shown in FIG. 26/(d) has a structure wherein the holder 126 shown in FIG. 26/(a) is attached to a metallic board 133 having a semi-circular shape. The metallic board 133 having a semi-circular shape is a thin plate having a thickness of 50 microns and a diameter of 3 mm. The holder 126 attached to the metallic board 133 is a sliver of silicon 127 having a length of about 2 mm, a width of about 50 microns and a height of about 0.5 mm. While electro-conductive adhesive is used for sticking the silicon holder 126 to the metallic board 133 in this example, another kind of adhesive is also usable. It should be noted that the silicon holder 126 is stuck to the metallic board 133 in such a way that the upper surface of the sliver of silicon 127 is placed at a level higher than the upper surface of the metallic board 133 in order to prevent an electron beam for TEM observation from being shielded by the metallic board 133. In the case of the holder 126, the surface for fixing an extracted micro-specimen 40 is the ground surface of the original silicon wafer which is adequately smooth. Since an extracted micro-specimen 40 is not fixed to the upper surface of the metallic board 133, on the other hand, the surface may be uneven to a certain degree, providing no obstacle to an observation using a TEM at all. Thus, since the work to fabricate the metallic board 133 is hardly a great strain on the nerves, the metallic board 133 can be fabricated with ease and at a low cost by adopting typically a punching method, a wet-etching method or electric-discharge machining method. As described above, in the example shown in FIG. 26/(d), the holder 126 shown in FIG. 26/(a) is attached to the metallic board 133. It should be noted, however, that the holder 128 shown in FIG. 26/(b) can be used in place of the holder 126 shown in FIG. 26/(a) to give entirely the same effect.

4 embodiments implementing specimen holders having different shapes for use in observations using a TEM have been explained. The basic concept embraced by the 4 embodiments is to make the surface for fixing an extracted micro-specimen extremely smooth and the width of the surface as small as possible. It is needless to say that a variety of versions based on this concept can be implemented.

Fifth Embodiment

In order to separate an infinitesimal micro-specimen 40 from a specimen substrate 2, a process to separate the bottom of the micro-specimen 40 to be extracted from the substrate 2 is indispensable. The process to separate the bottom of the micro-specimen 40 to be extracted from the specimen substrate 2 is referred to as a bottom-dividing process. In the conventional bottom-dividing fabrication method using an FIB explained earlier by referring to FIG. 4 and disclosed in prior-art reference 3, the FIB is irradiated in a direction slanting with respect to the surface of the specimen substrate 2 in order carry out the bottom-dividing fabrication. Thus, a slope is generated on the bottom of the extracted specimen surface 2. The slope is determined by the fabrication aspect ratio and the incidence angle of the FIB irradiated during the bottom-dividing fabrication. In the conventional method described above, the bottom-dividing fabrication is performed, that is, a trench 34 for separation is created. Thus, a large slope of about 70 degrees is resulted in on the specimen substrate 2. If the distance between the objective lens 50 and the specimen substrate 2 required by the focusability of the FIB is taken into consideration, in order to keep the performance of the normally used FIB apparatus, the inclination angle of the specimen substrate 2 should not exceed 60 degrees. In addition, inclination of the sample stage 3 for mounting a wafer 2 having a large diameter of 300 mm by an angle of 70 degrees is very difficult to implement from the mechanical point of view. Even if a large inclination angle of 70 degrees is possible, when the extracted micro-specimen 40 is mounted on the horizontal holding surface of the TEM-specimen holder, the surface of the micro-specimen 40 will form an angle of 20 degrees with the horizontal holding surface of the TEM-specimen holder because the bottom of the extracted micro-specimen 40 has an inclination of 20 degrees. As a result, it is difficult to create a trench and a wall on the micro-specimen 40 perpendicularly to the surface of the micro-specimen 40. In order to create a trench and a wall on the micro-specimen 40 perpendicularly to the surface of the micro-specimen 40, it is necessary to reduce the inclination of the bottom of the micro-specimen 40 and to make the bottom approximately parallel to the top surface of micro-specimen 40. To make the bottom approximately parallel to the top surface of micro-specimen 40, however, the inclination angle of the specimen substrate 2 during the bottom-dividing fabrication needs to be further increased, giving rise to more difficulties due to existing restrictions imposed on the configuration of the apparatus described above. For this reason, in order to mount an extracted micro-specimen 40, at which the present invention is aimed, on another member (that is, a TEM-specimen holder) and to introduce them into an apparatus for observation or analysis, a bottom-dividing method capable of creating a horizontal bottom or a vertical side surface needs to be studied. It should be noted that, in the method described in prior-art reference 3, the extracted micro-specimen is observed with the micro-specimen firmly held on the tip of a probe as it is without the need to mount the micro-specimen on a TEM-specimen holder. Thus, the observation is not affected by the shape of the bottom of the micro-specimen whatsoever.

In order to solve the problems described above, there has been studied an embodiment for implementing a method capable of extracting an infinitesimal micro-specimen 40 by bottom-dividing fabrication without the need to incline the sample stage 3 at an extremely large angle.

The procedure of the method for fabrication of a specimen provided by the present invention is explained below in concrete terms. In the explanation, the method for fabrication of a specimen is exemplified by a technique of fabricating a specimen for an observation using a TEM, starting with a process to mark an area to undergo an observation using a TEM and ending with a final thinning fabrication which all use an FIB. In order to clarify the procedure, the procedure is divided into some processes which are explained by referring to FIG. 27.

5-1 [Marking Process]

Figure 27:
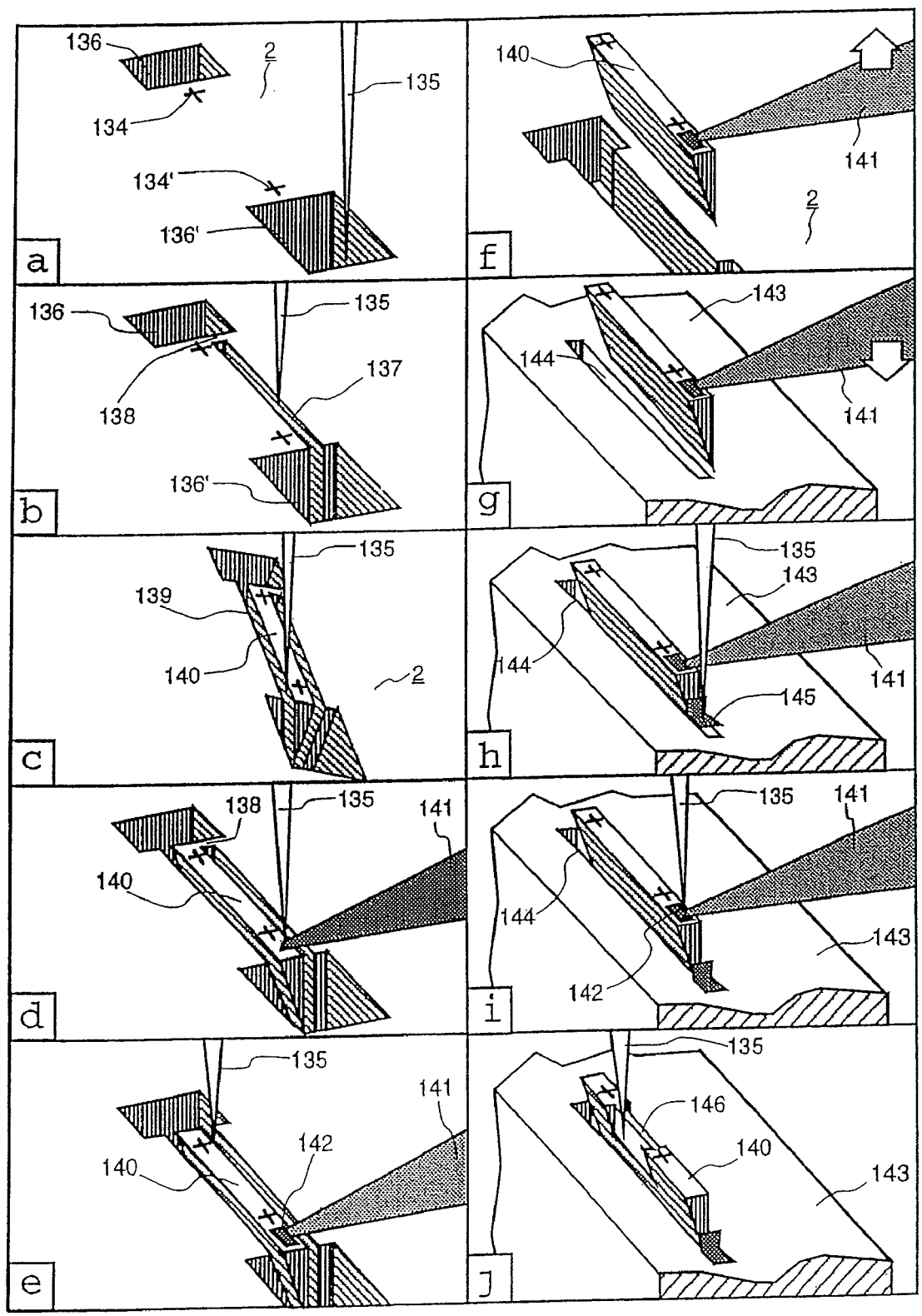
FIG. 27 is process explanatory diagrams showing a method for fabrication of a specimen as implemented by another embodiment of the present invention.

In the method for fabrication of a specimen, it is assumed that an infinitesimal micro-specimen including an area to undergo an observation using a TEM is separated and extracted from a specimen substrate. For this reason, it is feared that the position of the area to undergo an observation using a TEM can no longer be identified during a process of thinning the area to undergo an observation using a TEM on the micro-specimen separated and extracted from the specimen substrate (or a wall forming process). In order to solve this problem, it is necessary to put marks for identifying an area to undergo an observation using a TEM. With the specimen substrate still in a wafer or chip state, a position on the specimen substrate can be verified by computation of a position from CAD data or by means of an optical-microscope image or a scanning ion microscope (SIM). First of all, marks are put on an area to be observed (or a wall formation area). In this marking process, marks are put typically at both ends of the wall formation area by FIB or laser fabrication. In this embodiment, 2 cross marks 134 and 134' are put to sandwich the area to be observed, being separated away from each other by a distance of 10 microns. The posture of the sample stage 3 is adjusted in advance so that a straight line connecting the marks 134 and 134' to each other is oriented in parallel to the inclination axis of the sample stage 3. In order to protect a wall 146 during the marking process, a deposition film not shown in the figure may be created as shown in FIG. 27/*a*.

5-2 [Rectangular-Hole Fabrication Process]

On the extension lines on both ends of the straight line connecting the marks 134 and 134' to each other, 2 rectangular holes 136 and 136' are bored on the outer sides of the marks 134 and 134' by irradiation of an FIB 135. Each of the rectangular holes 136 and 136' has the following typical opening dimensions: an area of 10 microns×7 microns and a depth of about 15 microns. The rectangular holes 136 and 136' are separated from each other by a distance of 30 microns. It should be noted that, in order to carry out the fabrication of the rectangular holes 136 and 136' in a short period of time, a large FIB with a beam diameter of about 0.15 microns and a beam current of about 10 nA is used. As a result, the fabrication of the rectangular holes 136 and 136' can be completed in 7 minutes. Refer to FIG. 27/*a*.

5-3 [Vertical-Trench Fabrication Process]

Then, a thin long vertical trench 137 with a width of about 2 microns, a length of about 28 microns and a depth of about 15 microns is created by FIB scanning. The trench 137 is parallel to the straight line connecting the marks 134 and 134' and separated away from the line by a distance of about 2 microns. One end of the trench 137 reaches the rectangular hole 136' while the other end barely reaches the other rectangular hole 136. The direction of the FIB scanning is determined in such a way that sputter particles generated by irradiation of an FIB 135 do not fill up the vertical trench 137 and the rectangular holes 136 and 136' which have been created at great pains. A residual area 138 left between the rectangular hole 136 and the vertical trench 137 with a width of about 2 microns serves as a support area for temporarily supporting a micro-specimen 40 including an area to be observed when the micro-specimen 40 is separated from the specimen substrate 2. Refer to FIG. 27/*b*.

5-4 [Diagonal-Trench Fabrication Process]

The surface of the specimen substrate 2 which has been held horizontally level in processes 5-1 and 5-2 is slightly inclined typically by 20 degrees in this embodiment. Then, an inclined trench 139 is created in parallel to the straight line connecting the marks 134 and 134' on the side opposite to the vertical trench 137 by FIB scanning. The trench 139 is separated away from the line connecting the marks 134 and 134' by a distance of about 2 microns. Since the straight line connecting the marks 134 and 134' is set in parallel to the inclination axis of the sample stage 3 which is not shown in the figure, the surface of the specimen substrate 2 is inclined so that the inclined trench 139 is put at a level higher than the vertical trench 137. Created to connect the rectangular holes 136 and 136', the inclined trench 139 has a width of about 2 microns, a length of about 30 microns and a depth of about 18 microns. Also in this case, care must be exercised so that sputter particles generated by irradiation of an FIB 135 do not fill up the vertical trench 137, the inclined trench 139, the rectangular hole 136 and the rectangular hole 136' which have been created at great pains. The bottom of the inclined trench 139 is merged with the bottom of the vertical trench 137. As a result, a micro-sample 140 with a right-angled-triangular cross section having a wedge like shape with a bottom vertex of 20 degrees is separated from the specimen substrate 2 with the residual area 138 left between the rectangular hole 136 and the vertical trench 137 serving as a support area. The separated micro-specimen 140 is supported by the support area 138. Refer to FIG. 27/*c*.

5-5 [Deposition Process for Probe Fixation]

Then, after the surface of the specimen surface 2 is restored to the horizontal level, the tip of the probe 141 employed in the specimen transferring unit 4 is brought into contact with the end of the micro-specimen 140 on the side opposite to the support area 138. The contact state can be sensed by detecting a change in electrical conduction and a change in capacity between the micro-specimen 140 and the probe 141. In order to prevent a damage from being inflicted upon the probe 141 and the micro-specimen 140 due to careless pressing of the former against the latter, there is provided a function for halting the driving in the downward direction, that is, the pressing down, of the probe 141 as soon as the tip of the probe 141 comes in contact with the micro-specimen 140. Then, the tip of the probe 141 is firmly joined to the micro-specimen 140 by a deposition film 142 created on an area to which the FIB 135 is irradiated, strictly speaking, over which the FIB 135 sweeps in a scanning operation, while gas for deposition is being supplied to an area with an angle of about 2 microns including the tip of the probe 141. That is, the tip of the probe 141 is firmly joined to the micro-specimen 140 through the deposition film 142. Refer to FIG. 27/*d* and *e*.

5-6 [Micro-Specimen Extraction Process]

In order to extract the micro-specimen 140 from the specimen substrate 2, the FIB 135 is irradiated to the support area 138 holding the micro-specimen 140. The irradiation of the FIB eliminates the support area 138, releasing the micro-specimen 140 from the temporary held state. The support area 138 has an area of 2 square microns and a depth of about 15 microns which require an FIB irradiation (or scanning) of about 2 to 3 minutes to remove the support area 138. After the support area 138 has been removed, the micro element 140 is in a state of being completely separated and extracted from the specimen substrate 2. Refer to FIGS. 27/e and f.

5-7 [Micro-Specimen Transfer (Sample Stage Shifting) Process]

Then, the micro-specimen 140 separated and extracted from the specimen substrate 2 is moved to a TEM-specimen holder 143 with the micro-specimen 140 firmly attached to the tip of the probe 141 as it is. In actuality, it is the sample stage 3 that is shifted so that the TEM-specimen holder 143 mounted on the sample stage 3 is moved into the scanning range of the FIB 135. At that time, in order to avoid an unexpected accident, the micro-specimen 140 is saved at a position by a movement in the upward direction along with the probe 141 as shown by an arrow. As described earlier, there are a variety of methods for mounting the TEM-specimen holder 143 on the sample stage 3. In this example, it is assumed that the TEM-specimen holder 143 has been mounted on a TEM stage of the side-entry type. Refer to FIGS. 27/f and g.

5-8 [Micro-Specimen Fixation Process]

As the TEM-specimen holder 143 enters the scanning range of the FIB 135 due to a shift of the sample stage 3, the shift of the sample stage 3 is discontinued on the spot. Then, the probe 141 is moved downward to bring the micro-specimen 140 into contact with the TEM-specimen holder 143. Refer to FIG. 27/g.

As the tip of the micro-specimen 140 comes in contact with the upper surface of the TEM-specimen holder 143, a deposition film 145 is created at the contact location by irradiating the FIB 135 to the contact members while supplying gas for deposition to the contact members. In this way, the tip of the micro-specimen 140 is firmly joined to the upper surface of the TEM-specimen holder 143. In this embodiment, the deposition film 145 is created on a longitudinal-direction end surface of the micro-specimen 140. At that time, the area of a portion to which the FIB 135 is irradiated is about 3 square microns. Part of the created deposition film 145 is stuck on the TEM-specimen holder 143 whereas the rest is attached to a side surface of the micro-specimen 140 so that the film 145 firmly joins the holder 143 to the specimen 140. It should be noted that, as an alternative technique, in order to fix the micro-specimen 140 to the TEM-specimen holder 143 with an even higher degree of reliability, a thin long trench 144 with a width of about 2 microns, a length of about 32 microns and a depth of about 3 microns is created in advance on the specimen fixing surface of the TEM-specimen holder 143 by fabrication using an FIB. Then, after the bottom of the micro-specimen 140 is inserted into the thin long trench 144, a deposition film 145 is created on a longitudinal-direction end surface of the micro-specimen 140. As a matter of fact, FIG. 17/(g) and (h) are diagrams showing this alternative technique.

It is desirable to place the area on the micro-specimen 140 to be observed on the rotational-center axis of the TEM stage of the side-entry type. Since the micro-specimen 140 to be firmly joined to the TEM-specimen holder 143 has an infinitesimal size in the range several microns to several tens of microns, however, in actuality, it will be sufficient to bring the specimen fixing surface of the TEM-specimen holder 143 to the rotational-center axis of the TEM stage of the side-entry type. By doing so, the area on the micro-specimen 140 to be observed can be brought into the observation visual field of a TEM when the TEM stage is set in the TEM.

In addition, if at that time, the rotational-center axis of the TEM stage of the side-entry type is oriented in a direction parallel to the inclination axis of the sample stage 3, it will be no longer necessary to rotate the direction of the extracted micro-specimen 140. Thus, it is not necessary to install a complex rotating mechanism in the specimen transferring unit 4. In addition, there is exhibited an effect that, by employing a TEM stage of the side-entry type, the micro-specimen 140 can be introduced into the TEM right after its fabrication. Another effect is that, when an additional fabrication is required, the micro-specimen 140 can be returned to the FIB apparatus to undergo the additional fabrication.

5-9 [Probe Separating Process]

After the operation to supply deposition gas has been halted, an FIB 135 is irradiated to the deposition film 145 that firmly binds the tip of the probe 141 and the micro-specimen 140 together to eliminate the deposition film 145 by a sputtering process. As the deposition film 145 is eliminated, the probe 141 is detached from the micro-specimen 140. In this way, the micro-specimen 140 is firmly held by the TEM-specimen holder 143 and is put in a state completely independent of the probe 141. Refer to FIG. 27/i.

5-10 [Thinning Process]

Finally, the desired area on the micro-specimen 140 to be observed is subjected to a thinning finishing process to produce a wall 146 with a thickness not exceeding a value of about 100 nm. This thinning process is the last one of the sequence of processes to fabricate a TEM specimen. Since one of the longitudinal-direction side surfaces of the micro-specimen 140 is a vertical surface, an area subjected to radiation of an FIB for this thinning process is determined by taking this vertical surface as a reference. Thus, it is possible to create a wall 156 that is all but perpendicular to the surface of the original specimen substrate 2. In addition, in order to fabricate the surface of the wall 146 into a flatter level, an FIB deposition film can be created on the surface of the micro-specimen 140 including the wall formation area prior to the irradiation of the FIB. As a result of the thinning process described above, it is possible to form a wall with a horizontal width of about 15 microns and a depth of about 10 microns, allowing a specimen for use in an observation utilizing a TEM to be produced. Refer to FIG. 27/j.

All the processes described above, from the marking process to the thinning process, take about 1 hour and 30 minutes to complete, showing a reduction to a fraction of the length of time it takes to finish the processes according to the conventional methods for fabrication of a TEM specimen 5-11 [TEM-Observation Process]

After the thinning process described above has been completed, the TEM stage of the side-entry type is pulled out from the specimen chamber 77 of the FIB apparatus for fabricating a TEM specimen and brought into a TEM-specimen chamber. At that time, the TEM stage is rotated so that the path of an electron beam for observation crosses the wall surface perpendicularly before being brought into the TEM-specimen chamber. Generally known, the technology of the observation using a TEM carried out thereafter is not explained.

As described above, the procedure for fabricating a specimen as implemented by the embodiment applies to a specimen for observation using a TEM. It should be noted, however, that applications of the procedure are not limited to such a specimen. For example, the method can also used as a variety of other observation, analysis and measurement methods.

It is worth noting that the method for fabrication of a specimen provided by this embodiment is much different from the specimen fabrication method disclosed in prior-art reference 3 in that:

(1) The method for radiation of a beam during extraction and separation of a specimen is completely different. In the case of the present embodiment, in order to thin an extracted micro-specimen as much as possible and to simplify the separation (the bottom-dividing process) of the bottom of the micro-specimen from the specimen substrate, an inclination process of a specimen longitudinal-direction side surface is carried out. By the longitudinal direction, a direction parallel to the TEM observation surface is implied.

(2) In the case of this embodiment, an extracted micro-specimen is firmly held by a TEM-specimen holder, a member completely different from the probe of the specimen transferring unit.

As described above, according to the method for fabrication of a specimen provided by this embodiment, after marks are put on an area to be observed or analyzed on a specimen substrate such as a wafer or a device chip, a specimen for observations using a TEM, analyses, measurements or other kinds of observation can be fabricated from the specimen substrate immediately without manual work and without taking the specimen substrate from the vacuum specimen chamber of a specimen fabrication apparatus to a place outside the chamber. In addition, by using the specimen fabrication apparatus provided by the present embodiment, all the specimen-fabrication processes, from the marking process to the thinning process, can be carried out in a uniform manner by using only the sample-fabrication apparatus. As a result, it is possible to carry out a variety of operations, from extraction of a micro-specimen from mainly a semiconductor wafer and a semiconductor chip in addition to other materials and components to mounting of the micro-specimen on a TEM-specimen holder, without lengthy manual work requiring much training and skills such as grinding and the mounting of the micro-specimen on the TEM-specimen holder and with reduced possibility of risks such as dropping of a specimen during a transfer of the specimen from equipment to equipment. In particular, the length of time it takes to fabricate a TEM specimen can be reduced substantially.

Sixth Embodiment

When a probe is brought into contact with the surface of a specimen substrate by a specimen transferring unit in order to extract a micro-specimen from the specimen substrate, it is necessary to exercise care so as to prevent a damage or an injury from being inflicted upon the specimen substrate. This embodiment implements a specimen transferring method and a specimen transferring unit taking prevention of infliction of an injury on a specimen substrate into consideration.

Figure 28:
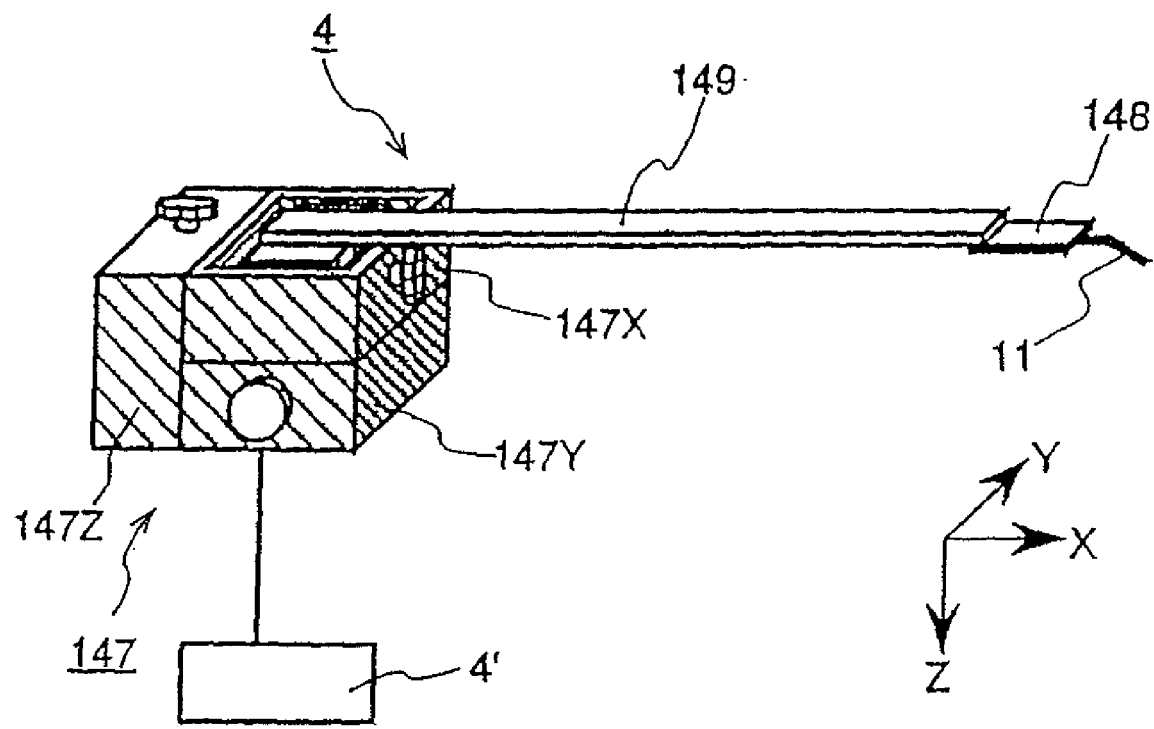
FIG. 28 is a diagram showing another typical configuration of a specimen transferring unit employed in the specimen fabrication apparatus provided by the present invention.

FIG. 28 is a diagram showing the configuration of a specimen transferring unit (or a manipulator) as implemented by this embodiment in a simple and plain manner. As shown in the figure, the specimen transferring unit 4 comprises a probe 11 for holding an extracted micro-specimen, a coarse-movement actuator 147 for moving the probe 11 in the 3 directions of the X, Y and Z axes at a low movement resolution and a fine-movement actuator 148 for moving the probe 11 in the Z-axial direction at a high movement resolution. The coarse-movement actuator 147 is installed at a location sufficiently separated away from a sample stage which is not shown in the figure. In order to allow the probe 11 attached to the fine-movement actuator 158 to make accesses to a wide range of locations on the sample stage, the fine-movement actuator 148 is connected to the coarse-movement actuator 147 through a long extension rod 149.

The coarse-movement actuator 147 comprises an X-axial-direction sub-actuator 147X, a Y-axial-direction sub-actuator 147Y and a Z-axial-direction sub-sub-actuator 147Z. The movement stroke is about 3 mm and the movement resolution is about 0.5 microns in each of the 3 axial directions. The fine-movement actuator 148 is implemented by a bimorph-type piezoelectric device with a movement stroke of about 200 microns and a movement resolution of about 0.05 microns.

As described above, the fine-movement actuator 148 is connected to the coarse-movement actuator 147 through the long extension rod 149 for a reason described as follows. In a space between an ion-beam irradiating optical system and a final-stage lens electrode employed in the specimen fabrication apparatus provided by the present invention and in the surrounding spaces, a variety of components coexist. In order to avoid contention for space with the variety of components, it is desirable to install the coarse-movement actuator 147, the main body of the specimen transferring unit 4 provided by the present invention, at a location as separated away as possible from the sample stage. In this embodiment, by using the extension rod 149, the coarse-movement actuator 147 can be installed at a location separated away from the sample stage.

Figure 29:
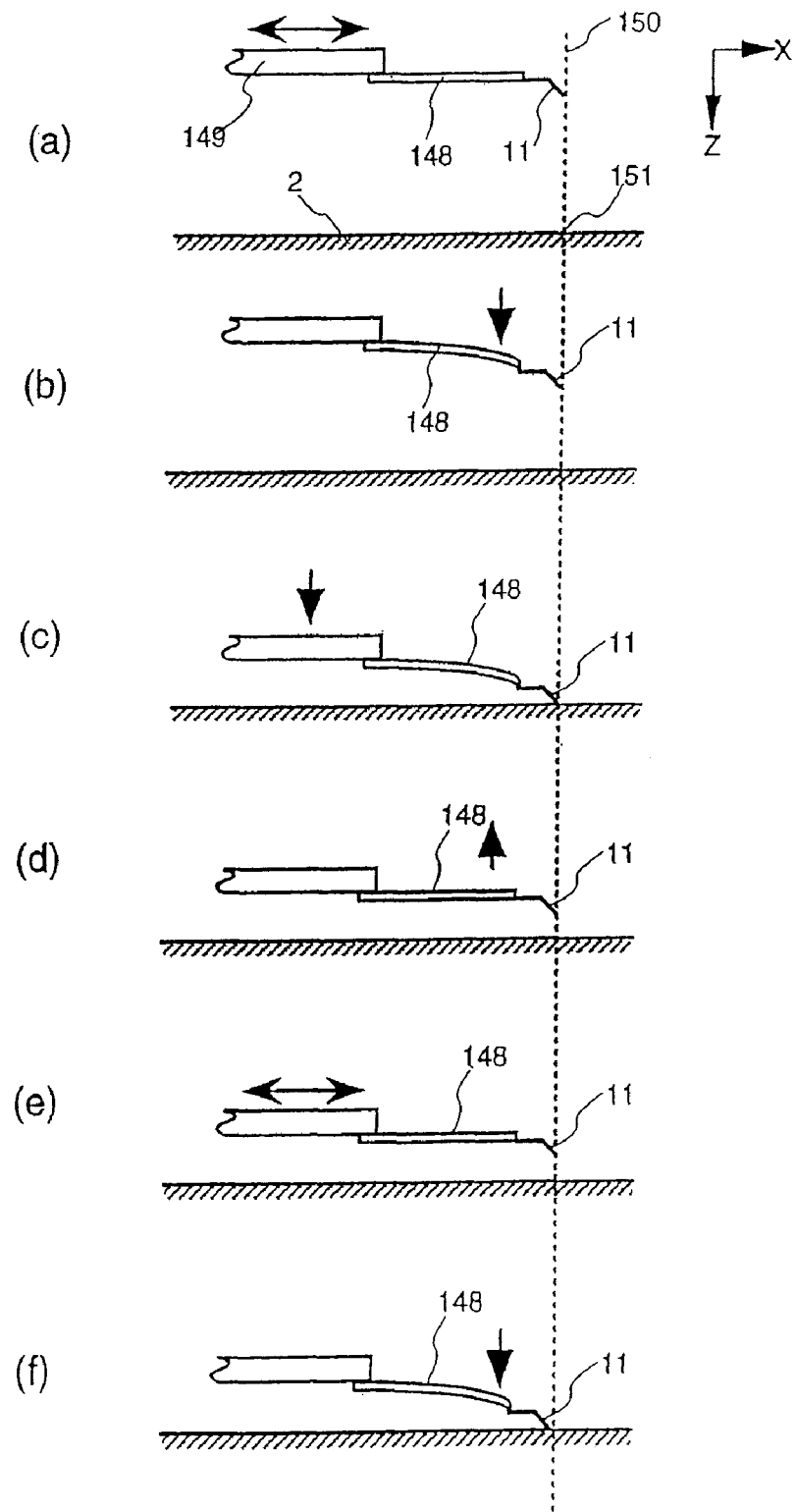
FIG. 29 is diagrams showing a procedure for bringing the tip of a probe into contact with the surface of a specimen substrate by using the specimen transferring unit shown in FIG. 28.

A procedure for bringing the tip of the probe 11 into contact with the surface of a specimen substrate 2 is explained by referring to FIG. 29. In FIG. 29, a point 151, an intersection of a dotted line 150 and the surface of the specimen substrate 2, is the target contact position of the probe 11.

Figure 30:
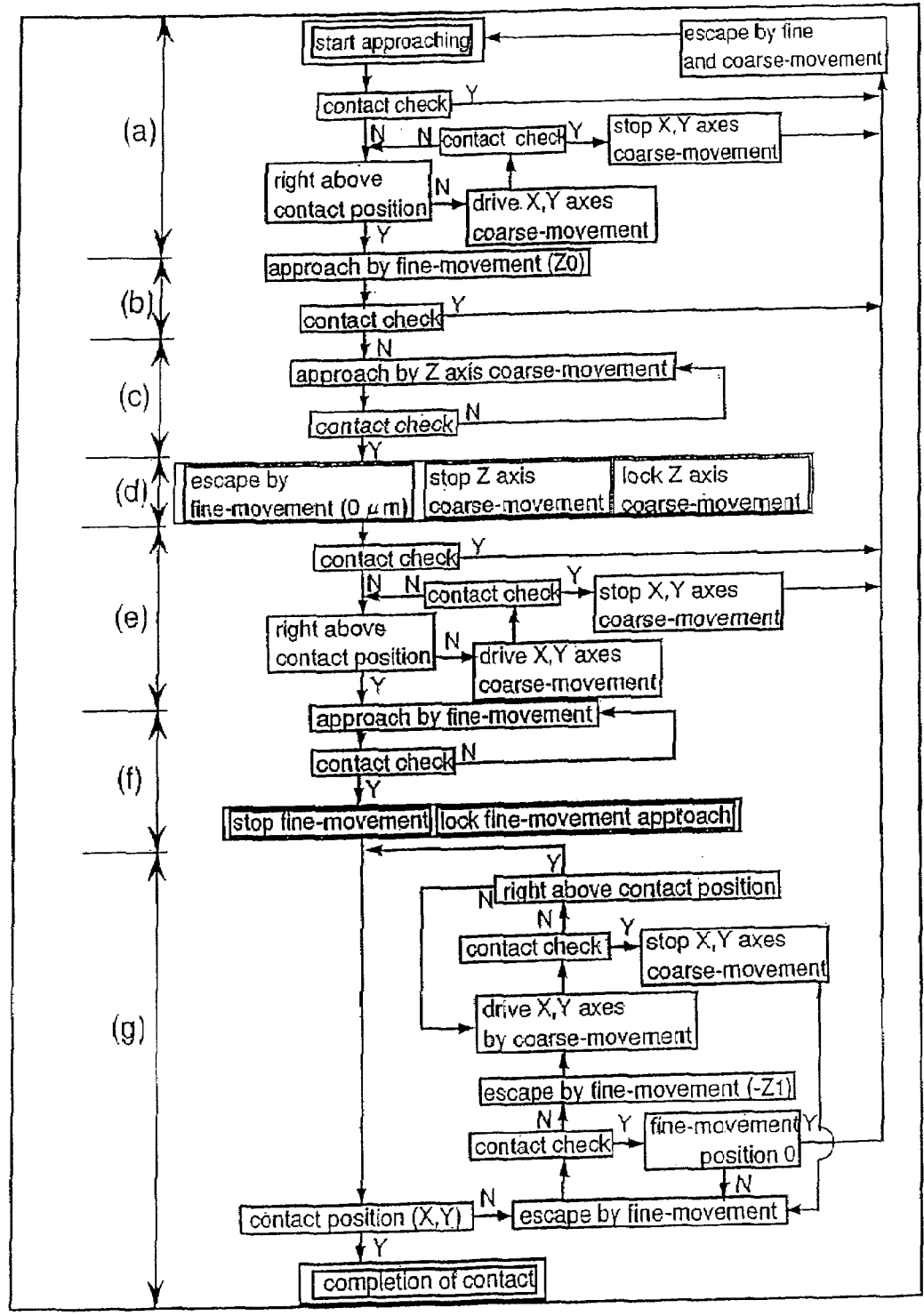
FIG. 30 is a flowchart used for explaining the procedure for bringing the tip of a probe into contact with the surface of a specimen substrate shown in FIG. 29.

FIG. 30 is a flowchart used for explaining the procedure comprising procedural steps shown in FIG. 29 /(a)-(f) for bringing the tip of the probe 11 into contact with the surface of the specimen substrate 2 shown in FIG. 29. It should be noted that, in the flowchart shown in FIG. 30, the symbol 'Y' appended to an arrow indicates the occurrence of an event. For example, if the event is contact check, the symbol 'Y' indicates that the contact check has been carried out. On the other hand, the symbol 'N' appended to an arrow indicates the non-occurrence of an event. For example, if the event is contact check, the symbol 'N' indicates that the contact check has not been carried out. Unless otherwise stated differently, the word 'contact' used in the flowchart shown in FIG. 30 means contact between the tip of the probe 11 and the surface of the specimen substrate 2. It should be noted that, in actuality, the state of contact between the tip of the probe 11 and the surface of the specimen substrate 2 is always monitored, that is, the work to check the contact is done all the time. Thus, when there is contact, an operation indicated by an arrow appended by the symbol 'Y' is carried out. In the following description, the phrase 'contact check' appears a number of times. Thus, in order to avoid redundant explanation, the detailed description of the contact-check event is omitted except for special cases.

First of all, after confirming that the tip of the probe 11 is not in contact with the surface of the specimen substrate 2, the X-axial-direction sub-actuator 147X and the Y-axial-direction sub-actuator 147Y are driven to move the tip of the probe 11 to a position right above the target contact position 151 as shown in FIG. 29/(a). Then, with the tip of the probe 11 located at a position separated away from the surface of the specimen substrate 2 by a distance of at least equal to the total stroke of the fine-movement actuator 148, the fine-movement actuator 148 is driven to bring the tip of the probe 11 closer to the surface of the substrate 2 from the origin of the fine-movement actuator 148 by a distance Z0 as shown in FIG.

29/(*b*). Typically, the distance Z0 is about 50% of the total stroke of the fine-movement actuator 148. Thus, in this embodiment, assuming that the total stroke is 200 microns, Z0 is about 100 microns. Then, the Z-axial-direction coarse-movement sub-actuator 147Z is driven to make the fine-movement actuator 148 approach the surface of the specimen substrate 2 till the tip of the probe 11 comes in contact with the surface of the specimen substrate 2 as shown in FIG. 29/(*c*). The contact between the tip of the probe 11 and the surface of the specimen substrate 2 can be confirmed typically by monitoring changes in electrical resistance between the tip of the probe 11 and the surface of the specimen substrate 2. As an alternative, the contact between the probe 11 and the surface of the specimen substrate 2 can be confirmed by applying a voltage to the probe 11 in advance and then monitoring changes in voltage contrast on a secondary-electron image of the surface of the specimen surface 2. As the contact between the probe 11 and the surface of the specimen substrate 2 is confirmed in this way, the movement of the Z-axial-direction coarse-movement actuator 147Z is halted at once and the fine-movement actuator 148 is driven again to let the tip of the probe 11 escape to the origin (a 0-micron position), that is, to swing upward to the 0-micron position. By letting the fine-movement actuator 148 escape from the surface of the specimen substrate 2, the tip of the probe 11 is restored to a position sufficiently separated from the surface of the specimen substrate 2, that is, a position separated from the surface of the specimen substrate 2 by an escape distance of about 100 microns, so that, no injury is inflicted upon both the tip of the probe 11 and the surface of the specimen substrate 2 even if the tip of the probe 11 has been brought into excessive approach with the surface of the specimen substrate 2 to a certain degree due to causes such as a drift or a lag of stopping of the Z-axial-direction coarse-movement actuator 147Z. Thus, the stroke of the fine-movement actuator 148 has to be sufficiently greater than a distance of the excessive approach due to causes such as a drift or a lag of stopping of the Z-axial-direction coarse-movement sub-actuator 147Z. In the case of the specimen transferring unit (the probe driving mechanism) 4 provided by the present invention, for example, the distance of the excessive approach of the Z-axial-direction coarse-movement sub-actuator 147Z is smaller than 1 micron and the stroke of the fine-movement actuator 148 is 200 microns as described above. Thus, since the escape distance of the fine-coarse actuator 148 is 100 microns which is 50% of the stroke, the escape distance can therefore sufficiently prevent an injury from being inflicted upon both the tip of the probe 11 and the surface of the specimen substrate 2. For the sake of more safety, the operation of the Z-axial-direction coarse-movement sub-actuator 147Z is looked and the Z-axial-direction coarse-movement sub-actuator 147Z can not thus be driven again as long as nothing is done to deliberately release the Z-axial-direction coarse-movement sub-actuator 147Z from the locked state. Refer to FIG. 29/(*d*). In this state, the X-axial-direction sub-actuator 147X and the Y-axial-direction sub-actuator 147Y are driven to finally adjust the position of the tip of the probe 11 to a location right above the target contact position 151 as shown in FIG. 29/(*e*). Finally, only the fine-movement actuator 148 is driven to bring the tip of the probe 11 into contact with the surface of the specimen substrate 2 softly as shown in FIG. 29/(*f*). Since the final contact can be established by only the fine-movement actuator 148 in this way, it is possible to prevent an injury from being inflicted upon both the tip of the probe 11 and the surface of the specimen substrate 2.

FIG. 30/(*g*) is a flowchart showing a method of adjustment which is adopted in case there is a positional shift after contact has been established. However, FIG. 29 does not include a diagram showing this adjustment procedure. As shown in the flowchart of FIG. 30/(*g*), if the actual contact position is shifted from the target contact position, the fine-movement actuator 148 is driven to escape in the upward direction so that the tip of the probe 11 is released from the contact state with the surface of the specimen substrate 2. If the tip of the probe 11 is till in contact with the surface of the specimen substrate 2 even after the fine-movement actuator 148 has been restored to the origin, that is, the 0-micron position, the Z-axial-direction sub-actuator 147Z is released from the locked state and the probe 11 is driven into a coarse movement in the Z-axis direction to let the tip thereof further escape. Then, the operation to move the tip of the probe 11 is resumed from an approaching operation by a coarse movement in the Z-axial direction. Even if the escaping fine movement by the fine-movement actuator 148 releases the tip of the probe 11 from the contact state with the surface of the specimen substrate 2, for caution's sake, the probe 11 is further driven upward by the fine-movement actuator 148 to let the tip thereof escape farther by a distance Z1. The value of Z1 is determined by the distances of movements by the tip of the probe 11 on the XY plane and the amount of the unevenness of the surface of the specimen substrate 2. Then, the X-axial-direction sub-actuator 147X and the Y-axial-direction sub-actuator 147Y are driven to take the tip of the probe 11 to a location right above the target contact position 151 as shown in FIG. 29/(*e*). Finally, only the fine-movement actuator 148 is driven to let the tip of the probe 11 approach the surface of the specimen substrate 2 and to bring the former into contact with the latter.

If a distance causing excessive approach caused by a creep or a lag of coarse-movement stopping described above can be estimated in advance, the escaping fine movement shown in FIG. 29/(*d*) is not necessarily made over a long distance of 100 microns from the Z0 position (or the 100-micron position) to the origin (or the 0-micron position). For example, if a distance causing excessive approach is estimated to be 5 microns or shorter, the distance of the escaping fine movement can be set at about 10 microns, or a distance from the 100-micron position to the 90-micron position. As an alternative, the fine-movement actuator 148 can be driven to once restore the tip of the probe 11 to the origin (the 0-micron position). Then, the probe 11 is driven to approach the surface of the specimen substrate 2 till the 90-micron position at a relatively high speed. Thereafter, the driving of the probe 11 is continued at a sufficiently low speed till the vicinity of the 100-micron position is reached. In this way, the tip of the probe 11 is brought into contact with the surface of the specimen substrate 2 by adopting the so-called variable-speed approaching technique. In this case, since the approaching speed of the probe 11 prior to a contact state is low, the probability of infliction of a damage on the specimen substrate 2 decreases and the length of the total time to drive the fine-movement actuator 148 can also be reduced as well.

If driving the probe 11 at a high movement resolution by the fine-movement actuator 148 causes a small displacement in the KY plane, procedural step (*e*) for driving the X-axial-direction sub-actuator 147X and the Y-axial-direction sub-actuator 147Y to finally adjust the position of the tip of the probe 11 to a location right above the target contact position 11 after procedural step (*d*) for driving the probe 11 at a high movement resolution to escape from the surface of the specimen substrate 2 is not meaningful any more. Thus, in this case, after procedural step (*b*) for driving the probe 11 at a high movement resolution to approach the Z0 position, the tip of the probe 11 is driven in the X and Y axial directions at a low movement resolution to a position right above the target contact position 151. Then, procedural steps (c) and (d) are executed to be followed by procedural steps (f) and (g) skipping procedural step (e) as described above to give a higher efficiency.

The method of bringing the tip of the probe 11 into contact with the surface of the specimen substrate 2 has been described above. It should be noted that the method can also be adopted to bring a micro-specimen 40 into contact with the TEM-specimen holder 19 after the micro-specimen 40 has been extracted from the specimen substrate 2. The description of the method of bringing the tip of the probe 11 into contact with the surface of the specimen substrate 2 holds true of the method to bring a micro-specimen 40 into contact with the TEM-specimen holder 19 if the micro-specimen 40 fixed on the probe 11 is substituted for the probe 11 in the description and the surface of the TEM-specimen holder 19 is substituted for the surface of the specimen substrate 2 in the description. Also in this case, it is needless to say that injuries can be effectively prevented from being inflicted upon the micro-specimen 40 and the TEM-specimen holder 19.

By adopting the method to bring a member into contact with another member described above, injuries can be effectively prevented from being inflicted upon the probe, the specimen substrate and the TEM-specimen holder.

A variety of embodiments of the present invention have been described above. It should be noted, however, that the scope of the present invention is not limited to the embodiments. In the description, the embodiments are mainly exemplified by fabrication of specimens for observations using a TEM. It is obvious, however, that the present invention can also be applied to fabrication of specimens for observations using other observation apparatuses such as an SEM and fabrication of specimens subjected to analyses and measurements.

As described above, according to the present invention, it is possible to fabricate specimens for an observation apparatus such as a TEM or other types of apparatus such as an analysis/measurement apparatus directly from a specimen substrate such as an integrated-circuit chip or a semiconductor wafer without requiring manual work. In addition, since a micro-specimen extracted from the substrate can be held in a cartridge, the micro-specimen can be controlled and maintained with ease. Moreover, the number of undesirable effects such as mechanical vibration generated by an external source during an observation or an analysis of the micro-specimen can be reduced.

POTENTIAL INDUSTRIAL APPLICATIONS

The method and apparatus for fabrication of specimens provided by the present invention can be utilized in fabrication of infinitesimal specimens subjected to observations, analyses and measurements of a small area on a substrate such as a semiconductor wafer or a semiconductor device chip. In particular, the method and apparatus are effective for fabrication of specimens subjected to observation using a TEM. The method and apparatus contribute to facilitation of clarification of causes of failures occurring during a process of manufacturing VLSI semiconductor devices.

What is claimed is:
1. A system for analyzing a semiconductor device, comprising:
a first ion beam apparatus including:
a sample stage to mount a sample substrate;
a vacuum chamber in which the sample stage is placed;
an ion beam irradiating optical system to irradiate the sample substrate;
a specimen holder that accommodates a plurality of specimens separated from the sample substrate by the irradiation of the ion beam; and
a probe to extract the separated specimen from the sample substrate, and to transfer the separated specimen to the specimen holder;
a second ion beam apparatus that carries out a finishing process to the specimen; and
an analyzer to analyze the finished specimen,
wherein the first ion beam apparatus separates the specimen and the probe in a vacuum condition.

2. A system for analyzing a semiconductor device, according to claim 1,
wherein the first ion beam apparatus conveys the specimen outside the vacuum chamber without breaking the vacuum condition.

3. A system for analyzing a semiconductor device, according to claim 1,
wherein the first ion beam apparatus comprises:
a deposition-gas supplying source to supply a deposition-gas to connect the probe and the specimen,
wherein separation of the probe and the specimen is carried out by irradiation of the ion beam.

4. A system for analyzing a semiconductor device, according to claim 1,
wherein the specimen holder accommodates a plurality of specimens.

5. A system for analyzing a semiconductor device, according to claim 1,
wherein the sample substrate is a semiconductor wafer.

6. A system for analyzing a semiconductor device, comprising:
a first ion beam apparatus including:
a sample stage to mount a sample substrate;
a vacuum chamber in which the sample stage is placed;
an ion beam irradiating optical system to irradiate the sample substrate;
a specimen holder that accommodates a plurality of specimens separated from the sample substrate by the irradiation of the ion beam;
a probe to extract the separated specimen from the sample substrate, and to transfer the separated specimen to the specimen holder;
a second ion beam apparatus that carries out a finishing process to the specimen; and
an analyzer to analyze the finished specimen,
wherein the first ion beam apparatus separates the specimen and the probe in the vacuum chamber.

7. A system for analyzing a semiconductor device, according to claim 6,
wherein the first ion beam apparatus conveys the specimen outside the vacuum chamber without breaking a vacuum condition.

8. A system for analyzing a semiconductor device, according to claim 6,
wherein the first ion beam apparatus comprises:
a deposition-gas supplying source to supply a deposition-gas to connect the probe and the specimen,
wherein separation of the probe and the specimen is carried out by irradiation of the ion beam.

9. A system for analyzing a semiconductor device, according to claim 6,
wherein the specimen holder accommodates a plurality of specimens.

10. A system for analyzing a semiconductor device, according to claim 6,
wherein the sample substrate is a semiconductor wafer.

11. A system for analyzing a semiconductor device, comprising:
a first ion beam apparatus including:
a sample stage to mount a sample substrate;
a vacuum chamber in which the sample stage is placed;
an ion beam irradiating optical system to irradiate the sample substrate;
a specimen holder that accommodates a plurality of specimens separated from the sample substrate by the irradiation of the ion beam;
a probe to extract the separated specimen from the sample substrate, and to transfer the separated specimen to the specimen holder;
a deposition-gas supplying source to supply a deposition-gas to connect the probe and the specimen;
a second ion beam apparatus that carries out a finishing process to the specimen; and
an analyzer to analyze the finished specimen,
wherein the specimen and the probe are separated by irradiation of the ion beam in the vacuum chamber.

12. A system for analyzing a semiconductor device, according to claim 11,
wherein the first ion beam apparatus conveys the specimen outside the vacuum chamber without breaking a vacuum condition.

13. A system for analyzing a semiconductor device, according to claim 11,
wherein the specimen holder accommodates a plurality of specimens.

14. A system for analyzing a semiconductor device, according to claim 11,
wherein the sample substrate is a semiconductor wafer.

* * * * *